US006977162B2

(12) United States Patent
Dhallan

(10) Patent No.: US 6,977,162 B2
(45) Date of Patent: Dec. 20, 2005

(54) RAPID ANALYSIS OF VARIATIONS IN A GENOME

(75) Inventor: Ravinder S. Dhallan, Bethesda, MD (US)

(73) Assignee: Ravgen, Inc., Columbia, MD (US)

( * ) Notice: Subject to any disclaimer, the term of this patent is extended or adjusted under 35 U.S.C. 154(b) by 365 days.

(21) Appl. No.: 10/093,618

(22) Filed: Mar. 11, 2002

(65) Prior Publication Data

US 2003/0186239 A1 Oct. 2, 2003

Related U.S. Application Data

(60) Provisional application No. 60/360,232, filed on Mar. 1, 2002.

(51) Int. Cl.⁷ .......................... C12P 19/34; C12Q 1/68; C07H 21/04
(52) U.S. Cl. ........................ 435/91.2; 435/6; 435/91.1; 536/24.3; 536/24.33
(58) Field of Search .................. 435/6, 91.1, 91.2; 536/24.3, 24.33

(56) References Cited

U.S. PATENT DOCUMENTS

| | | | |
|---|---|---|---|
| 4,521,509 A | * | 6/1985 | Benkovic et al. ............... 435/6 |
| 4,683,195 A | | 7/1987 | Mullis et al. |
| 4,683,202 A | | 7/1987 | Mullis |
| 4,800,159 A | | 1/1989 | Mullis et al. |
| 4,889,818 A | | 12/1989 | Gelfand et al. |
| 4,965,188 A | | 10/1990 | Mullis et al. |
| 5,023,171 A | | 6/1991 | Ho et al. |
| 5,066,584 A | | 11/1991 | Gyllensten et al. |
| 5,075,216 A | | 12/1991 | Innis et al. |
| 5,079,352 A | | 1/1992 | Gelfand et al. |
| 5,091,310 A | | 2/1992 | Innis |
| 5,104,792 A | | 4/1992 | Silver et al. |
| 5,432,054 A | | 7/1995 | Saunders et al. |
| 5,538,848 A | | 7/1996 | Livak et al. |
| 5,545,552 A | * | 8/1996 | Mathur .................... 435/252.3 |
| 5,565,339 A | | 10/1996 | Bloch et al. |
| 5,618,664 A | | 4/1997 | Kiessling |
| 5,631,147 A | * | 5/1997 | Lohman et al. ............ 435/91.2 |
| 5,641,628 A | | 6/1997 | Bianchi |
| 5,648,222 A | | 7/1997 | Tse et al. |
| 5,723,591 A | | 3/1998 | Livak et al. |
| 5,744,301 A | | 4/1998 | Birkenbach et al. |
| 5,831,065 A | | 11/1998 | Brenner |
| 5,858,671 A | * | 1/1999 | Jones ........................... 435/6 |
| 5,965,363 A | * | 10/1999 | Monforte et al. ............... 435/6 |
| 5,998,141 A | | 12/1999 | Acton |
| 6,090,553 A | | 7/2000 | Matson |
| 6,110,709 A | * | 8/2000 | Ausubel et al. ............ 435/91.2 |
| 6,124,120 A | | 9/2000 | Lizardi |
| 6,180,372 B1 | | 1/2001 | Franzen |
| 6,203,989 B1 | | 3/2001 | Goldberg et al. |
| 6,225,061 B1 | | 5/2001 | Becker et al. |
| 6,251,639 B1 | | 6/2001 | Kurn |
| 6,258,540 B1 | | 7/2001 | Lo et al. |
| 6,387,621 B1 | | 5/2002 | Wittwer |
| 6,475,736 B1 | | 11/2002 | Stanton, Jr. |
| 6,506,561 B1 | * | 1/2003 | Cheval et al. ................ 435/6 |
| 6,613,517 B2 | * | 9/2003 | Michelotti .................... 435/6 |
| 2001/0051341 A1 | | 12/2001 | Lo et al. |
| 2002/0045176 A1 | | 4/2002 | Lo et al. |
| 2003/0044388 A1 | | 3/2003 | Dennis et al. |
| 2003/0054386 A1 | | 3/2003 | Antonarakis et al. |
| 2003/0082576 A1 | | 5/2003 | Jones et al. |
| 2003/0099964 A1 | * | 5/2003 | Pattil et al. .................. 435/6 |
| 2003/0232348 A1 | | 12/2003 | Jones et al. |
| 2004/0106102 A1 | | 6/2004 | Dhallan |
| 2004/0137470 A1 | | 7/2004 | Dhallon |

FOREIGN PATENT DOCUMENTS

| | | |
|---|---|---|
| EP | 0 994 963 | 4/2000 |
| GB | 2 299 166 | 9/1996 |
| WO | WO 91/08304 | 6/1991 |
| WO | WO 95/06137 | 3/1995 |
| WO | WO 98/39474 | 9/1998 |
| WO | WO 02/04672 | 1/2002 |
| WO | WO 02/083839 | 10/2002 |
| WO | WO 03/074723 | 9/2003 |
| WO | WO 03/074740 | 9/2003 |
| WO | WO 03/106642 | 12/2003 |

OTHER PUBLICATIONS

Written Opinion mailed on Mar. 10, 2005 for PCT patent application No. PCT/US03/06376 filed on Feb. 28, 2003. 3 pages.
Brown, E. L. et al. (1979). "Chemical Synthesis and Cloning of a Tyrosine tRNA Gene," *Methods in Enzymology* 68:109–151.
Center for Medical Genetics. (1998–2003). Human Insertion/Deletion Polymorphisms http://research.marshfield-clinicorg/genetics/. Last visited on Apr. 14, 2003. 3 pages.
Cooper, D. N. and Krawczak, M. eds.(1993). "Human Gene Mutation," *In Duchenne Muscular Dystrophy, Alzheimer's Disease, Cystic Fibrosis, and Huntington's Disease*. BIOS Scientific Publishers Limited. (Table of Contents only).
Erlich, H. A. ed. (1989). *PCR Technology: Principals and Applications of DNA Amplification*, Stockton Press. pp. ix–x. (Table of Contents only).
Huber, M. et al. (2001). "Detection of Single Base Alterations in Genomic DNA by Solid Phase Polymerase Chain Reaction on Oligonucleotide Microarrays," *Analytical Biochemistry* 299:24–30.

(Continued)

*Primary Examiner*—Kenneth R. Horlick
*Assistant Examiner*—Young J. Kim
(74) *Attorney, Agent, or Firm*—Morrison & Foerester LLP

(57) ABSTRACT

The invention provides a method useful for determining the sequence of large numbers of loci of interest on a single or multiple chromosomes. The method utilizes an oligonucleotide primer that contains a recognition site for a restriction enzyme such that digestion with the restriction enzyme generates a 5' overhang containing the locus of interest. The 5' overhang is used as a template to incorporate nucleotides, which can be detected. The method is especially amenable to the analysis of large numbers of sequences, such as single nucleotide polymorphisms, from one sample of nucleic acid.

54 Claims, 22 Drawing Sheets

OTHER PUBLICATIONS

Innis, M. A. ed., (1990). *PCR Protocols: A Guide to Methods and Applications.* Academic Press, Inc. pp. v–x. (Table of Contents only).

Kaneoka, H. et al. (1991). "Solid–Phase Direct DNA Sequencing of Allele–Specific Polymerase Chain Reaction–Amplified HLA–DR Genes," *Biotechniques* 10(1):30, 32 and 34 only.

McPherson, M. J. et al. eds., (1991). *PCR: A Practical Approach,* IRL Press at Oxford University Press. Total pp. 6. (Table of Contents).

Narang, S. A. et al. (1979). "Improved Phosphotriester Method for the Synthesis of Gene Fragments," *Methods in Enzymology* 68:90–98.

Poch, M. T. et al. (1997). "Sth132I, A Novel Class–IIS Restriction Endonuclease of *Streptococcus thermophilus* ST132," *Gene* 195:201–206.

Riordan, J. R. et al. (1989). "Identification of the Cystic Fibrosis Gene: Cloning and Characterization of Complementary DNA," *Science* 245(4922):1066–1073.

Rommens, J. M. et al. (1989). "Identification of the Cystic Fibrosis Gene: Chromosome Walking and Jumping," *Science* 245:1059–1065.

Sambrook, J. and Russell, D. W. eds., (2001). *Molecular Cloning Laboratory Manual.* vol. 2 Third Edition, Cold Spring Harbor Laboratory Press. pp. v–xx. (Table of Contents only).

Sanger, F. et al. (1977). "DNA Sequencing with Chain–Terminating Inhibitors," *PNAS USA* 74(12):5463–5467.

Shah, J. S. et al. (1995). "Q–Beta Replicase–Amplified Assay for Detection of *Mycobacterium tuberculosis* Directly from Clinical Specimens," *Journal of Clinical Microbiology.* 33(6):1435–1441.

Shapero, M. H. et al. (2001). "SNP Genotyping by Multiplexed Solid–Phase Amplification and Fluorescent Minisequencing," *Genome Research* 11:1926–1934.

SNP Report for TSC0087315. (Aug. 2000). http://snp.cshl.org/snpsearch.shtml. Last visited on Apr. 14, 2003. 2 pages.

SNP Report for TSC0095512. (Aug. 2000). http://snp.cshl.org/snpsearch.shtml. Last visited on Apr. 14, 2003. 2 pages.

SNP Report for TSC0264580. (Aug. 2000). http://snp.cshl.org/snpsearch.shtml. Last visited on Apr. 14, 2003. 2 pages.

SNP Report for TSC0413944. (Aug. 2000). http://snp.cshl.org/snpsearch.shtml. Last visited on Apr. 14, 2003. 2 pages.

Wallace, R.W. (1997). "DNA on a Chip: Serving Up the Genome for Diagnostics and Research," *Molecular Medicine Today* 3:384–389.

Wang, D. G. et al. (1998). "Large–Scale Identification, Mapping, and Genotyping of Single–Nucleotide Polymorphisms in the Human Genome," *Science* 280:1077–1082.

Waterston, R.H. and McPherson, J.D. (2001). "A Map of Human Genome Sequence Variation Containing 1.42 Million Single Nucleotide Polymorphisms," *Nature* 409:928–933.

Blanchard, A. P. and Hood, L. (1996). "Sequence to Array: Probing the Genome's Secrets," *Nature Biotechnology* 14:1649.

Brenner, S. et al. (2000). "Gene Expression Analysis by Massively Parallel Signature Sequencing (MPSS) on Microbead Arrays," *Nature Biotechnology* 18:630–634.

Broude, N. et al. (2001). "High–Level Multiplex DNA Amplification," *Antisense & Nucleic Acid Drug Development* 11:327–332.

Chen, J. et al. (2000). "A Microsphere–Based Assay for Multiplexed Single Nucleotide Polymorphism Analysis Using Single Base Chain Extension," *Genome Research* 10:549–557.

Chicurel, M. (2001). "Faster, Better, Cheaper Genotyping," *Nature* 412:580–582.

Collins, F. S. and Mansoura, M. K. (2001). "The Human Genome Project: Revealing the Shared Inheritance of All Humankind," $7^{th}$ *Biennial Symposium on Minorities, the Medically Underserved and Cancer* 91(1):221–225.

Cutler, D. J. et al. (2001). "High–Throughput Variation Detection and Genotyping Using Microarrays," *Genome Research* 11:1913–1925.

Drábek, J. (2001). "A Commented Dictionary of Techniques for Genotyping," *Electrophoresis* 22:1024–1045.

Egholm, M. et al. (1992). "Peptide Nucleic Acids (PNA), Oligonucleotide Analogues with an Achiral Peptide Backbone," *Journal of the American Chemical Society* 114(5):1895–1897.

Gerhold, D. et al. (1999). "DNA Chips: Promising Toys have Become Powerful Tools," *TIBS* 24:168–173.

Green, A. et al. (1990). "Direct Single Stranded Sequencing from Agarose of Polymerase Chain Reaction Products," *Nucleic Acids Research* 18(20):6163–6164.

Grösch, S. et al. (2001). "A Rapid Screening Method for a Single Nucleotide Polymorphism (SNP) in the Human MOR Gene," *Br. J. Clin Pharmacol* 52:711–714.

Hogervorst, F. B. L. et al. (1995). "Rapid Detection of BRCA1 Mutations by the Protein Truncation Test," *Nature Genetics* 10:208–212.

Hsu, T. M. et al. (2001). "Genotyping Single–Nucleotide Polymorphisms by the Invader Assay with Dual–Color Fluorescence Polarization Detection," *Clinical Chemistry* 47(8):1373–1377.

James, P. et al. (1994). "Protein Identification in DNA Databases by Peptide Mass Fingerprinting," *Protein Science* 3:1347–1350.

Kandpal, R. P. et al. (1990). "Selective Enrichment of a Large Size Genomic DNA Fragment by Affinity Capture: An Approach for Genome Mapping," *Nucleic Acids Research* 18(7):1789–1795.

Kwok, P–Y. (2001). "Methods for Genotyping Single Nucleotide Polymorphisms," *Annual Review of Genomics and Human. Genetics* 2:235–258.

Lander, E. S. et al. (2001). "Initial Sequencing and Analysis of the Human Genome," *Nature* 409:860–921.

Li, J. et al. (1999). "Single Nucleotide Polymorphism Determination using Primer Extension and Time–of–Flight Mass Spectrometry," *Electrophoresis* 20:1258–1265.

Lockhart, D. J. and Winzeler, E. A. (2000). "Genomics, Gene Expression and DNA Arrays," *Nature* 405:827–836.

Maxam, A. M. and Gilbert, W. (1977). "A New Method for Sequencing DNA," *Proc. Natl. Acad. Sci.* 74(2):560–564.

Nielsen, P. E. et al. (1991). "Sequence–Selective Recognition of DNA by Strand Displacement with a Thymine–Substituted Polyamide," *Science* 254:1497–1500.

Orban, T. et al. (2000). "Sequence Alterations Can Mask Eash Other's Presence during Screening with SSCP or Heteroduplex Analysis: BRCA Genes as Examples," *BioTechniques* 29(1):94–98.

Roest, P. A. M. et al. (1993). "Protein Truncation Test (PTT) for Rapid Detection of Translation–Terminating Mutations," *Human Molecular Genetics* 2(10):1719–1721.

Shi, M. M. (2001). "Enabling Large–Scale Pharmacogenic Studies by High–Throughput Mutation Detection and Genotyping Technologies," *Clinical Chemistry* 47(2):164–172.

Sibson, D. R. et al. (2001). "Molecular Indexing of Human Genomic DNA," *Nucleic Acids Research* 29(19):1–10.

Subramanian, G. et al. (2001) "Implications of the Human Genome for Understanding Human Biology and Medicine," *JAMA* 286(18):2296–2307.

Syvänen, A–C. (1999). "From Gels to Chips: "Minisequencing" Primer Extension for Analysis of Point Mutations and Single Nucleotide Polymorphisms," *Human Mutation* 13:1–10.

Szybalski, W. et al. (1991). "Class–IIS Restriction Enzymes—A Review," *Gene* 100:13–26.

Taton, T. A. et al. (2000). "Scanometric DNA Array Detection with Nanoparticles Probes," *Science* 289:1757–1760.

Tsongalis, G. J. et al. (2001). "READIT: A Novel Technology Used in the Interrogation of Nucleic Acid Sequences for Single–Nucleotide Polymorphisms," *Experimental and Molecular Pathology* 71:222–225.

Welsh K. and Bunce, M. (1999). "Molecular Typing for the MHC with PCR–SSR," *Reviews in Immunogenetics* 1:157–176.

Westin, L. et al. (200). "Anchored Multiplex Amplification on a Microelectronic Chip Array," *Nature Biotechnology* 18:199–204.

Van Der Luijt, R. et al. (1994). "Rapid Detection of Translation–Terminating Mutations at the Adenomatous Polyposis Coli (APC) Gene by Direct Protein Truncation Test," *Genomics* 20:1–4.

Venter, J. C. et al. (2001). "The Sequence of the Human Genome," *Science* 291:1304–1351. (Erratum attached, 1 page Jun. 2001).

Zhou, G–H. et al. (2001). "Quantitative Detection of Single Nucleotide Polymorphisms for a Pooled Sample by a Bioluminometric Assay Coupled with Modified Primer Extension Reactions (BAMPER)," *Nucleic Acids Research* 29(19):1–11.

Ahlquist, D.A. et al. (2000). "Colorectal Cancer Screening by Detection of Altered Human DNA in Stool: Feasibility of a Multitarget Assay Panel," *Gastroenterology* 119:1219–1227.

Amicucci, P. et al. (2000). "Prenatal Diagnosis of Myotonic Dystrophy Using Fetal DNA Obtained from Maternal Plasma," *Clinical Chemistry* 46(2):301–302.

Anker, P. et al. eds. (Apr. 2000). "Circulating Nucleic Acids in Plasma or Serum," Table of Contents from the *First International Symposium on Circulating Nucleic Acids in Plasma/Serum: Implication in Cancer Diagnosis, Prognosis, or Follow–up and in Prenatal Diagnosis*, Apr. 18–20, 1999 in Menthon Saint–Bernard, France, located at <http://www.unige.ch/LABPV/symposium/cnaps/cnaps_book.html> last visited on Mar. 27, 2001, four pages.

Anonymous (Dec. 16, 1996). "Birth Defects: Maternal Blood Gets Put to the Test," *Physician's Weekly Clinical Updates* located at: <http://www.physweekly.com/archive/96/12_16_19/cu4.html> last visited on Mar. 27, 2001, one page.

Anonymous (Dec. 17, 1998). "Strategies for the Rapid Prenatal Detection of Down's Syndrome," *CMGS* located at <http://www.ich.ucl/ac/uk/cmgs/downs98.html> last visited on Mar. 27, 2001, four pages.

Anonymous (2001). "Methods of Ultrasensitive Bioanalysis: DNA Sequencing and Indexing" *Union Bay Ultrasensitive Bioanalysis Team* located at <http://faculty.washington.edu/dovichi/research/application/DNA/DNASequencing.html> last visited Apr. 16, 2001, four pages.

Anonymous (2001). "Molecular Indexing (MI) Home Page," *Helix Research Institute* located at <http://www.hri.co.jp/MI> last visited Apr. 16, 2001, four pages.

Barnett, E.V. (Jun. 1968). "Detection of Nuclear Antigens (DNA) in Normal and Pathologic Human Fluids by Quantitative Complement Fixation," *Arthritis and Rheumatism* 11(3):407–417.

Bauer, M. et al. (Jan. 2002). "Detection of Maternal Deoxyribonucleic Acid in Umbilical Cord Plasma by Using Fluorescent Polymerase Chain Reaction Amplification of Short Tandem Repeat Sequences," *Am. J. Obstet. Gynecol.* 186:117–120.

Beer, A.E. et al. (Sep. 7, 1994). "The Biological Basis of Passage of Fetal Cellular Material into the Maternal Circulation," *Annals New York Academy of Sciences* 731:21–35.

Bennett, P.R. et al. (Aug. 26, 1993). "Prenatal Determination of Fetal RhD Type by DNA Amplification," *The New England Journal of Medicine* 329(9):607–610.

Bianchi, D.W. (Dec. 1995). "Prenatal Diagnosis by Analysis of Fetal Cells in Maternal Blood," *The Journal of Pediatrics* 127(6):847–856.

Bianchi, D.W. (1998). "Current Knowledge About Fetal Blood Cells in the Maternal Circulation," *J. Perinat. Med.* 26:175–185.

Bianchi, D.W. (1998). "Fetal DNA in Maternal Plasma: The Plot Thickens and the Placental Barrier Thins," *Am. J. Hum. Genet.* 62:763–764.

Bianchi, D.W. (2000). "A Guest Editorial: State of Fetal Cells in Maternal Blood: Diagnosis or Dilemma," *Obstetrical and Gynecological Survey* 55(11):665–667.

Bianchi, D.W. (Sep. 2000). "Fetal Cells in the Mother: From Genetic Diagnosis to Diseases Associated with Fetal Cell Microchimerism," *European Journal of Obstetrics & Gynecology and Reproductive Biology* 92:103–108.

Bianchi, D.W. et al. (1990). "Isolation of Fetal DNA From Nucleated Erythrocytes in Maternal Blood," *Proc. Natl. Acad. Sci USA* 87:3279–3283.

Bianchi, D.W. et al. (1996). "Male Fetal Progenitor Cells Persist in Maternal Blood for as Long as 27 Years Postpartum," *Proc. Natl. Acad. Sci. USA* 93:705–708.

Bianchi, D.W. et al. (1997). "PCR Quantitation of Fetal Cells in Maternal Blood in Normal and Aneuploid Pregnanices," *Am. J. Hum. Genet.* 61:822–829.

Bianchi, D.W. et al. (Mar. 27, 2001). "Longitudinal Fetal DNA Quantitation Studies in Maternal Cells and Plasma over a 24 Hour Period," Program Nr: 2377 located at <http://www.faseb.org/genetics/ashg00/f2377.html> last visited on Mar. 27, 2001, one page.

Bianchi, D.W. et al. (2001). "Thoughts on the Origin of Fetal DNA in the Pregnant Woman," Abstract 3.4 In Chapter 3 "Clinical Applications of Fetal DNA in Maternal Plasma," *In Abstracts, 12th Fetal Cell Workshop, Fetal Diagn. Ther.*, 16:450.

Brambati, B. (Sep. 7, 1994). "Prenatal Diagnosis by Isolating and Analyzing Fetal Nucleated Red Cells: Dream or Reality?" *Annals New York Academy of Sciences* 731:248–252.

Bruch, J. F. et al. (1991). "Trophoblast–Like Cells Sorted From Peripheral Maternal Blood Using Flow Cytometry: A Multiparametric Study Involving Transmission Electron Microsopy and Fetal DNA Amplification," *Prenatal Diagnosis* 11:787–798.

Cairns, P. et al. (Sep. 2001). "Molecular Detection of Prostate Cancer in Urine by GSTP1 Hypermethylation," *Clin. Can. Res.* 7:2727–2730.

Camaschella, C. et al. (Jun. 1, 1990). "Prenatal Diagnosis of Fetal Hemoglobin Lepore–Boston Disease on Maternal Peripheral Blood," *Blood* 75(11):2102–2106.

Chen, X.Q. et al. (Sep. 1996). "Microsatellite Alterations in Plasma DNA of Small Cell Lung Cancer Patients," *Nature Medicine* 2(9):1033–1035.

Cox, R.A. et al. (Feb. 1977). "DNA Concentrations in Serum and Plasma," *Clinical Chemistry* 23(2):297.

Cunningham, J. et al. (Oct. 1999). "Non–Invasive RNA–Based Determination of Fetal Rhesus D Type: A Prospective Study Based on 96 Pregnancies," *British J. of Ob–Gyn* 106:1023–1028.

Davis, G.L. et al. (Jan.–Feb., 1973). "Detection of Circulating DNA by Counterimmuno–electrophoresis (CIE)," *Athritis and Rheumatism* 16(1):52–58.

Douglas, G.W. et al. (Nov. 1959). "Trophoblast in the Circulating Blood During Pregnancy," *American Journal of Obstetrics and Gynecology* 78(5):960–973.

Durant, J. et al. (Jun. 26, 1999). "Drug–Resistance Genotyping in HIV–1 Therapy: The VIRADAPT Randomised Controlled Trial," *The Lancet* 353:2195–2199.

Durant, J. et al. (Sep. 25, 1999). "Drug–Resistant Genotyping in HIV–1 Therapy," *The Lancet* 354:1120–1122.

El–Naggar, A.K. et al. (Nov. 2001). "Genetic Heterogeneity in Saliva from Patients with Oral Squamous Carcinomas: Implications in Molecular Diagnosis and Screening," *J. Mol. Diag.* 3(4):164–170.

Emanuel, S.L. et al. (1993). "Amplification of Specific Gene Products from Human Serum," *GATA* 10(6):144–146.

Farina, A. et al. (1998). "Fetal Cells in Maternal Blood as a Second Non–Invasive Step for Fetal Down Syndrome Screening," *Prenat. Diagn.* 18:979–986.

Field, J.K. et al. (Jun. 1, 1999). "Genetic Alterations in Bronchial Lavage as a Potential Marker for Individuals with a High Risk of Developing Lung Cancer," *Cancer Research* 59:2690–2695.

Fournié, G.J et al. (1993). "Plasma DNA as Cell Death Marker in Elderly Patients," *Gerontology* 39:215–221.

Fowke, K.R. et al. (1995). "Genetic Analysis of Human DNA Recovered From Minute Amounts of Serum or Plasma," *Journal of Immunological Methods* 180:45–51.

Gänshirt–Ahlert, D. et al. (May 1992). "Magnetic Cell Sorting and the Transferrin Receptor as Potential Means of Prenatal Diagnosis from Maternal Blood," *Am. J. Obstet. Gynecol.* 166:1350–1355.

Hahn, S. et al. (2001). "An Examination of Fetal Cells, Free Fetal DNA and Fetal Cell Culture: The Basel Experience," Abstract 3.2 In Chapter 3 "Clinical Applications of Fetal DNA in Maternal Plasma," *In Abstracts, 12th Fetal Cell Workshop, Fetal Diagn. Ther.*, 16:449.

Hedenfalk, I. et al. (Feb. 22, 2001). "Gene–Expression Profiles in Hereditary Breast Cancer," *New Engl. Jnl. Med.* 344(8):539–548.

Heinemann, J.A. et al. (Apr. 2000). "New Hypotheses on the Material Nature of Horizontally Mobile Genes," *Annals New York Academy of Sciences* 906:169–186.

Herzenberg, L.A. et al. (1979). "Fetal Cells in the Blood of Pregnant Women: Detection and Enrichment by Fluorescence–Activated Cell Sorting," *Proc. Natl. Acad. Sci. USA* 76(3):1453–1455.

Holzgreve, W. et al. (2000). "Fetal Cells in Cervical Mucus and Maternal Blood," *Baillière's Clinical Obstetrics and Gynaecology* 14(4):709–722.

Holzgreve, W. et al. (Jun. 2001). "Prenatal Diagnosis Using Fetal Cells and Free Fetal DNA in Maternal Blood," *Clinics in Perinatology* 28(2):353–365.

Human Gene Mutation Database (HGMD). (Date Unknown). Located at <http:archive.uwcm.ac.uk/uwcm/mg/hgmd0.html> last visited on Sep. 20, 2004, 3 pages total.

International Search Report mailed on Jul. 17, 2003, for PCT Patent Application No. PCT/US03/06376 (filed on Feb. 28, 2003, 4 pages. (3.40).

International Search Report mailed on Jul. 20, 2004 for PCT patent application No. PCT/US03/27308 filed Aug. 29, 2003, 8 pages. (4.41).

International Search Report mailed on Sep. 02, 2003, for PCT patent application No. PCT/US03/06198 filed on Feb. 28, 2003, 9 pages. (4.40).

Kamm, R.C. et al. (1972). "Nucleic Acid Concentrations in Normal Human Plasma," *Clinical Chemistry* 18(6):519–522.

Kamm, R.C. et al. (1975). "Plasma Deoxyribonucleic Acid Concentrations of Women in Labor and Umbilical Cords," *American Journal of Obstetrics and Gynecology* 121(1):29–31.

Kang, A. et al. (1999). "Fetal Cells in Maternal Blood: Their Role in Non–Invasive Prenatal Diagnosis and in Disease," ("Fetale Zellen im mütterlichen Blut—ihre Bedeutung für eine nicht–invasive pränatale Diagnostik und bei der Ätiologie bestimmter Erkrankungen,") *Schweiz Med. Wochenschr* 129:1470–1743. English Translation and original language article.

Kinzler, K.W. et al. (Aug. 9, 1991). "Identification of FAP Locus Genes from Chromosome 5q21," *Science* 253:661–665.

Kuo, P–L. (1999). "Fetal Cell Isolation From Maternal Blood—Clinical and Biological Implications," *Adv. Obstet. Perinatol.* 10(1):15–24.

Kwak, J.Y.H. et al. (Sep. 7, 1994). "Biological Basis of Fetoplacental Antigenic Determinants in the Induction of the Antiphospholipid Antibody Syndrome and Recurrent Pregnancy Loss," *Annals New York Academy of Sciences* 731:242–245.

Lagona, F. et al. (Apr. 2000), "Fetal DNA Analysis from Maternal Plasma and Nucleated Blood Cells," *Annals New York Academy of Sciences* 906:156–160.

Leon, S.A. et al. (1977). "Free DNA in the Serum of Rheumatoid Arthritis Patients," *Journal of Rheumatology* 4(2):139–143.

Liloglou, T. et al. (Feb. 15, 2001). "Cancer–Specific Genomic Instability in Bronchial Lavage: A Molecular Tool for Lung Cancer Detection," *Cancer Research* 61:1624–1628.

Lo, Y.M. (Sep. 7, 1994). "An Improved PCR–Based System for Prenatal Sex Determination from Maternal Peripheral Blood," *Annals New York Academy of Sciences* 731:214–216.

Lo, Y.M. et al. (Sep. 7, 1994). "Strategies for the Detection of Autosomal Fetal DNA Sequence from Maternal Peripheral Blood," *Annals New York Academy of Sciences* 731:204–213.

Lo, Y.M.D. (Sep. 7, 1994). "Prenatal Determination of Fetal Rhesus D Status by DNA Amplification of Peripheral Blood of Rhesus–Negative Mothers," *Annals New York Academy of Sciences*, 731:229–236.

Lo, Y.M.D. (Dec. 1994). "Non–Invasive Prenatal Diagnosis Using Fetal Cells in Maternal Blood," *Journal of Clinical Pathology* 47(12):1060–1065.

Lo, Y.M.D. (1999). "Fetal RhD Genotyping From Maternal Plasma," *Annals of Medicine* 31(5):308–312.

Lo, Y.M.D. (1999). "Rapid Clearance of Fetal DNA from Maternal Plasma," *Am. J. Hum. Genet.* 64:218–224.

Lo, Y.M.D. (Apr. 2000). "Fetal DNA in Maternal Plasma," *Annals of New York Academy of Sciences* 906:141–147.

Lo, Y.M.D. (Dec. 2000). "Fetal DNA in Maternal Plasma: Biology and Diagnostic Applications," *Clinical Chemistry* 46(12):1903–1906.

Lo, Y.M.D. (2001). "Fetal DNA in Maternal Plasma," Abstract 3.1 In Chapter 3 "Clinical Applications of Fetal DNA in Maternal Plasma," *In Abstracts, 12th Fetal Cell Workshop, Fetal Diagn. Ther.*, 16:448–449.

Lo, Y.M.D. (Jun. 2001). "Fetal DNA in Maternal Plasma: Application to Non–Invasive Blood Group Genotyping of the Fetus," *Transfus. Clin. Biol.* 8(3):306–310.

Lo, Y.M.D. et al. (Dec. 9, 1989). "Prenatal Sex Determination by DNA Amplification From Maternal Peripheral Blood," *The Lancet* 2:1363–1365.

Lo, Y.M.D. et al. (Jun. 16, 1990). "Detection of Single–Copy Fetal DNA Sequence From Maternal Blood," *Lancet* 335:1463–1464.

Lo, Y.M.D. et al. (1994). "Detection of Fetal RhD Sequence From Peripheral Blood of Sensitized RhD–Negative Pregnant Women," *British Journal of Hematology* 87:658–660.

Lo, Y.M.D. et al. (Dec. 1, 1996). "Two–Way Cell Traffic Between Mother and Fetus: Biologic and Clinical Implications," *Blood* 88(3):4390–4395.

Lo, Y.M.D. et al. (Aug. 16, 1997). "Presence of Fetal DNA in Maternal Plasma and Serum," *The Lancet* 350:485–487.

Lo, Y.M.D. et al. (1998). "Quantitative Anaylysis of Fetal DNA in Maternal Plasma and Serum: Implications for Noninvasive Prenatal Diagnosis," *Am. J. Hum. Genet.* 62:768–775.

Lo, Y.M.D. et al. (1999). "Increased Fetal DNA Concentrations in the Plasma of Pregnant Women Carrying Fetuses with Trisomy 21," *Clinical Chemistry* 45(10):1747–1751.

Longo, M.C. et al. (1990). "Use of Uracil DNA Glycosylase to Control Carry–Over Contamination in Polymerase Chain Reactions," *Gene* 93:125–128.

Mao, L. et al. (Feb. 2, 1996). "Molecular Detection of Primary Bladder Cancer by Microsatellite Analysis," *Science* 271:659–662.

Martin, M. et al. (Feb. 1992). "A Method for Using Serum of Plasma as a Source of DNA for HLA Typing," *Human Immunology* 33(2):108–113.

Miller, D. ed. (Aug. 16, 1996). "Notes on Fifth Fetal Cell Workshop," Amsterdam, May 3, 1996, published and located at <http://iubio.bio.indiana.edu> last visited on Mar. 27, 2001, four pages.

Mueller, U.W. et al. (Jul. 28, 1990). "Isolation of Fetal Trophoblast Cells From Peripheral Blood of Pregnant Women," *The Lancet* 336:197–200.

Mulcahy, H.E. et al. (Sep. 7, 1996). "Cancer and Mutant DNA in Blood Plasma," *The Lancet* 348:628.

Muller, F. et al. (Mar. 2000). "Parental Origin of the Extra Chromosome in Prenatally Diagnosed Fetal Trisomy 21," *Hum. Genet.* 106:340–344.

Nawroz, H. et al. (Sep. 1996). "Microsatelite Alterations in Serum DNA of Head and Neck Cancer Patients," *Nature Medicine* 2(9):1035–1037.

Pertl, B. et al. (May 14, 1994). "Rapid Molecular Method for Prenatal Detection of Down's Syndrome," *The Lancet* 343:1197–1198.

Pertl, B. et al. (Jan. 6, 2000). "Detection of Male and Female Fetal DNA in Maternal Plasma by Multiplex Fluorescent Polymerase Chain Reaction Amplification of Short Tandem Repeats," *Hum. Genet.* 106:45–49.

Pertl, B. et al. (Mar. 27, 2001). "Detection of Male and Female Fetal DNA in Maternal Plasma by Multiplex Fluorescent Polymerase Chain Reaction Amplification of Short Tandem Repeats," located at <http://link.springer.de/link/service/journals/00439/contents/99/00166/s004399900166ch002.html> last visited on Mar. 27, 2001, one page.

Pertl, B. et al. (Oct. 1999). "First Trimester Prenatal Diagnosis: Fetal Cells in the Maternal Circulation," *Seminars in Perinatology* 23(5):393–402.

Pertl, B. et al. (Mar. 27, 2001). "Detection of Male and Femal Fetal DNA in Maternal Plasma by Multiples Fluorescent Polymerase Chain Reaction Amplification of Short Tandem Repeats (STRs)," Program Nr: 410 located at <http://www.faseb.org/genetics/ashg99/f410.html> last visited Mar. 27, 2001, one page.

Pertl, B. et al. (Sep. 2001). "Fetal DNA in Maternal Plasma: Emerging Clinical Applications," *Obstetrics and Gynecology* 98(3):483:490.

Poon, L.L.M. (2000). "Presence of Fetal RNA in Maternal Plasma," *Clin. Chem.* 46(11):1832–1834.

Poon, L.L.M. et al. (Nov. 25, 2000). "Prenatal Detection of Fetal Down's Syndrome from Maternal Plasma," *The Lancet* 356:1819–1820.

Poon, L.L.M. et al. (Nov. 2001). "Circulating Fetal DNA in Maternal Plasma," *Clinica Chimmica Acta* 313:151–155.

Promega, Inc. (Dec. 1999). "Wizard® DNA Clean–Up System," *Promega Corp. Technical Bulletin* TB141:1–4.

Ramster, B. (Jul. 2, 2001). "IVF Screening for Down's Syndrome Flawed, Say Experts," *BioMedNet* located at <http://news.bmn,com/news/story?day=010703&story> last visited Jul. 3, 2001, one page.

Raptis, L. et al. (Dec. 1980). "Quantitation and Characterization of Plasma DNA in Normals and Patients with Systemic Lupus Erythematosus," *Journal of Clinical Investigation* 66:1391–1399.

Samura, O. et al. (Jul. 2000). "Female Fetal Cells in Maternal Blood: Use of DNA Polymorphisms to Prove Origin," *Hum. Genet.* 107:28–32.

Samura, O. et al. (Sep. 2001). "Diagnosis of Trisomy 21 in Fetal Nucleated Erythrocytes from Maternal Blood by Use of Short Tandem Repeat Sequences," *Clinical Chemistry* 47(9):1622–1626.

Shapiro, B. et al. (1983). "Determination of Circulating DNA Levels in Patients with Benign or Malignant Gastrointestinal Disease," *Cancer* 51:2116–2120.

Sidransky, D. (Apr. 2000). "Circulating DNA: What We Know and What We Need to Learn," In Circulating Nucleic Acids in Plasma or Serum, *Annals New York Academy of Sciences* 906:1–4.

Simpson, J.L. et al. (1994). "Isolating Fetal Cells in Maternal Circulation for Prenatal Diagnosis," *Prenatal Diagnosis* 14:1229–1242.

Simpson, J.L. et al. (Sep. 7, 1994). "Fetal Cells in Maternal Blood. Overview and Historical Perspective," *Annals New York Academy of Sciences* 731:1–8.

Smid, M. et al. (1999). "Evaluation of Different Approaches for Fetal DNA Analysis from Maternal Plasma and Nucleated Blood Cells," *Clinical Chemistry* 45(8):1570–1572.

Smid, M. et al. (2001). "Quantitative Analysis of Fetal DNA in Maternal Plasma in Pregnancies Affected by Insulin-Dependent Diabetes mellitus (IDDM)," Abstract 3.3 In Chapter 3 "Clinical Applications of Fetal DNA in Maternal Plasma," *In Abstracts, 12th Fetal Cell Workshop, Fetal Diagn. Ther.*, 16:449–450.

SNP Entry Report for HC21S00007. (Date Unknown). located at <http//:csnp.unige.ch/cgi–bin/csnp_fetch?entry=HC21S0007> last visited on Sep. 27, 2004, one page.

SNP Entry Report for HC21S0027. (Date Unknown). located at <http//:csnp.unige.ch/cgi–bin/csnp_fetch?db+csnp&format=html&entryxHC21S00027> last visited on Sep. 27, 2004, one page.

SNP Entry Report for HC21S00131. (Date Unknown). located at <http//:csnp.unige.ch/cgi–bin/csnp_fetch?db+csnp&format=html&entry=HC21S00131> last visited on Sep. 27, 2004, one page.

SNP Entry Report for HC21S00340. (Date Unknown). located at <http//:csnp.unige.ch/cgo–bin/csnp_fetch?entry=HC21S00340> last visited on Sep. 27, 2004, 2 pages.

SNP Report for TSC 0214366. (Oct. 2000). located at <http://snp.cshl.org/snpsearch.shtml> Last visited on Dec. 30, 2003, 2 pages.

Spafford, M. F. et al. (Mar. 2001). "Detection of Head and Neck Squamous Cell Carcinoma Among Exfoliated Oral Mucosal Cells by Microsatellite Analysis," *Clinical Cancer Research* 7:607–612.

Steele, C.D. et al. (Dec. 1996). "Prenatal Diagnosis Using Fetal Cells Isolated From Maternal Peripheral Blood: A Review," *Clinical Obstetrics and Gynecology* 39(4):801–813.

Strickland, S. et al. (Oct. 30, 1992). "Invasion of the Trophoblasts," *Cell* 71:355–357.

Stroun, M. et al. (Apr. 2000). "The Origin and Mechanism of Circulating DNA," *Annals New York Academy of Sciences* 906:161–168.

Tan, E.M. et al. (1966). "Deoxyribonucleic Acid (DNA) and Antibodies to DNA in the Serum of Patients with Systemic Lupis Erythematosus," *Journal of Clinical Investigation* 45(11):1732–1740.

Tang, N.L.S. et al. (1999). "Detection of Fetal–Derived Paternally Inherited X–Chromosome Polymorphisms in Maternal Plasma," *Clinical Chemistry* 45(11):2033–2035.

Thomas, M.R. et al. (Sep. 7, 1994). "The Time of Appearance, and Quantitation, of Fetal DNA in the Maternal Circulation," *Annals New York Academy of Sciences* 731:217–225.

Tockman, M. (Jan.–Feb. 2000). "Advances in Sputum Analysis for Screening and Early Detection of Lung Cancer," *Cancer Control* 7(1):19–24.

Traverso, G. et al. (Jan. 31, 2002). "Detection of APC Mutations in Fecal DNA from Patients With Colorectal Tumors," *New England Journal of Medicine* 346(5):311–320.

Tsao, J. et al. (Sep. 1994). "Further Evidence That One of the Earliest Alterations in Colorectal Carcinogenesis Involves APC," *Am. J. Pathol.* 145(3):531–534.

Ugozzoli, L. et al. (1992). "Detection of Specific Alleles by Using Allele–Specific Primer Extension Followed by Capture on Solid Support," *GATA* 9(4):107–112.

Utting, M. et al. (Jan. 2002). "Microsatellite Analysis of Free Tumor DNA in Urine, Serum, and Plasma of Patients: A Minimally Invasive Method for the Detection of Bladder Cancer," *Clinical Cancer Res.* 8:35–40.

van Wijk, I.J. et al. (2000). "Detection of Apoptotic Fetal Cells in Plasma of Pregnant Women," *Clinical Chemistry* 46(5):729–731.

Velculescu, V.E. et al. (Oct. 2000). "Analysing Uncharted Transcriptomes with SAGE," *TIG* 16(10): 423–425.

Verma, L. et al. (Jul. 4, 1998). "Rapid and Simple Prenatal DNA Diagnosis of Down's Syndrome," *The Lancet* 352:9–11.

Wallknowska, J. et al. (Jun. 7, 1969). "Practical and Theoretical Implications of Fetal/Maternal Lymphocyte Transfer," *The Lancet* 1:1119–1122.

Xie, D. et al. (Mar. 1, 2000). "Population–Based, Case–Control Study of HER2 Genetic Polymorphism and Breast Cancer Risk," *J. Natl. Cancer Institute* 92(5):412–417.

Yamamoto, T. et al. (Mar. 1994). "Anti–ssDNA and dsDNA Antibodies in Preeclampsia," *Asia Oceania J. Obstet. Gynaecol.* 20(1):93–99.

Zhang, L. et al. (Jul. 1992). "Whole Genome Amplification From a Single Cell: Implications for Genetic Analysis," *Proc. Natl. Acad. Sci.* 89:5847–5851.

Zhen, D.K. et al. (1998). "Poly–Fish: A Technique of Repeated Hybridizations That Improves Cytogenetic Analysis of Fetal Cells in Maternal Blood," *Prenat. Diagn.* 18:1181–1185.

Zhong, X.Y. et al. (2000). "Fetal DNA in Maternal Plasma is Elevated in Pregnancies with Aneuploid Fetuses," *Prenatal Diagnosis* 20:795–798.

\* cited by examiner

FIG. 1C
First Primer
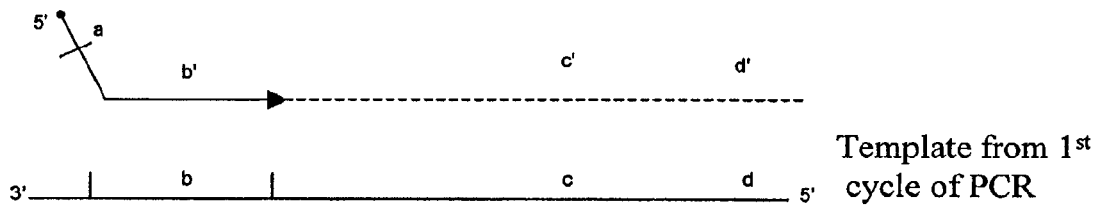
Template from 1st cycle of PCR
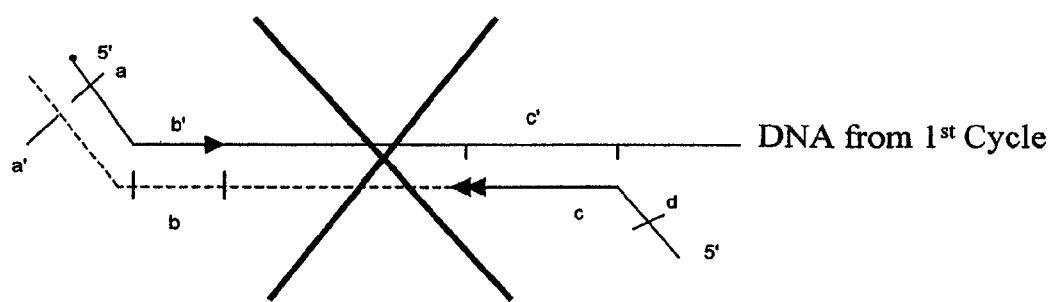
DNA from 1st Cycle

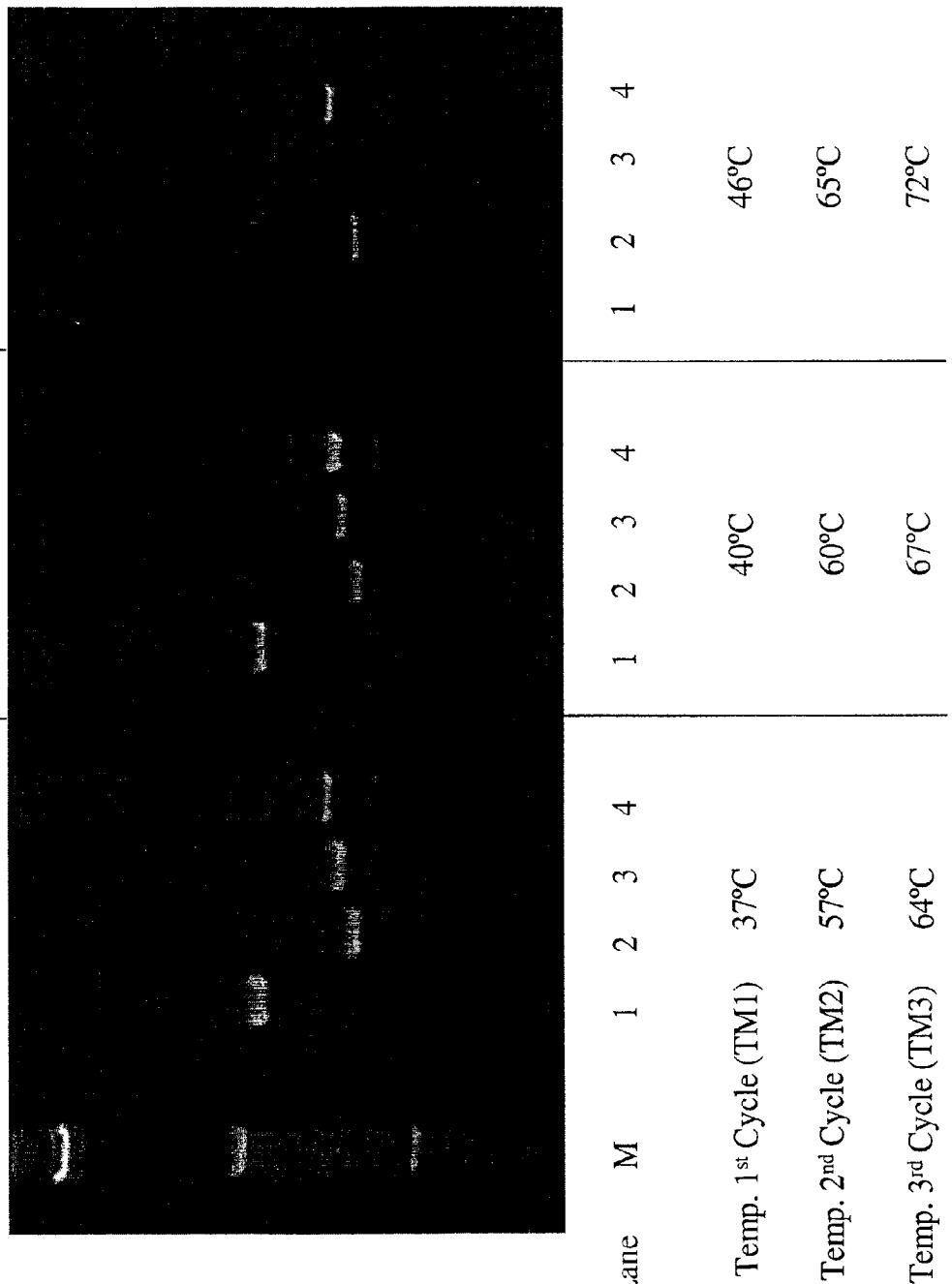

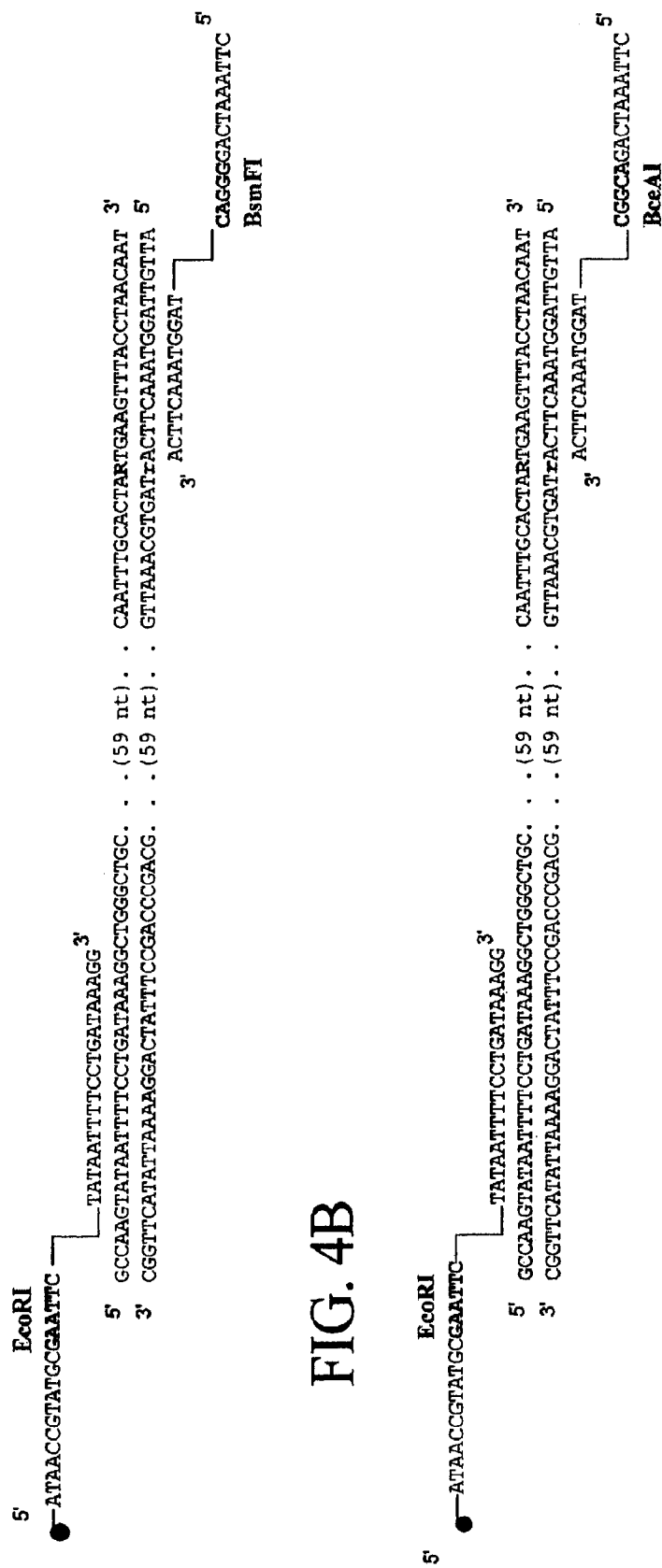

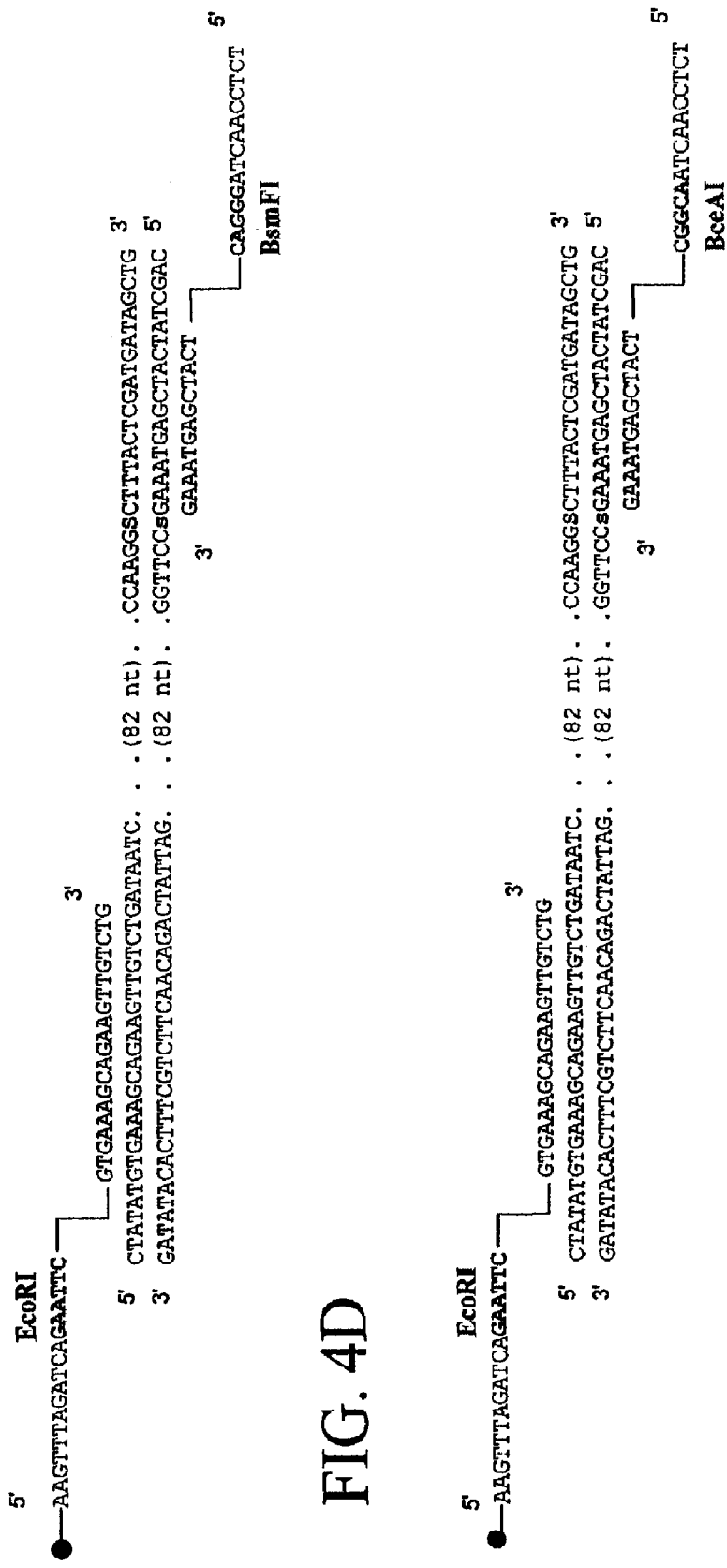

FIG. 6C

```
       EcoRI
5'—AAGTTTAGATCAGAATTCGTGAAAGCAGAAGTTGTCTGATAATC...(82 nt)...CCAAGG              3'
3'   TTCAAATCTAGTCTTAAGCACTTTCGTCTTCAACAGACTATTAG...(82 nt)...GGTTCCsGAA         5'

5' SCTTTACTCGATGAGTCCCTTATCGTGAT 3'
                                                       3' ATGAGCTACTCAGGGAATAGCACTA     5'
                                                                      BsmFI
```

FIG. 6D

```
       EcoRI
5'—AAGTTTAGATCAGAATTCGTGAAAGCAGAAGTTGTCTGATAATC...(82 nt)...CCAAGG              3'
3'   TTCAAATCTAGTCTTAAGCACTTTCGTCTTCAACAGACTATTAG...(82 nt)...GGTTCCsG           5'

5' SCTTTACTCGATGAGCCGTTATCCGTGAT 3'
                                                       3' AAATGAGCTACTCGGCAATAGCACTA    5'
                                                                      BceAI
```

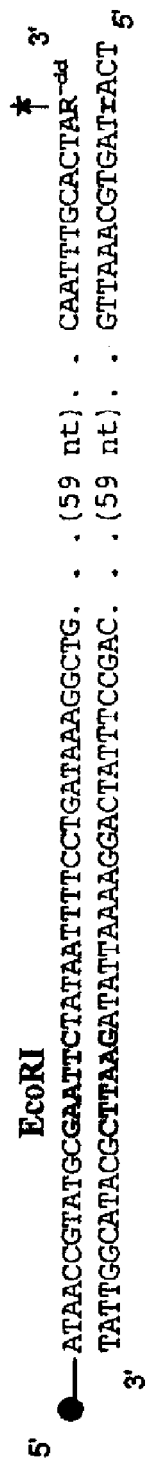
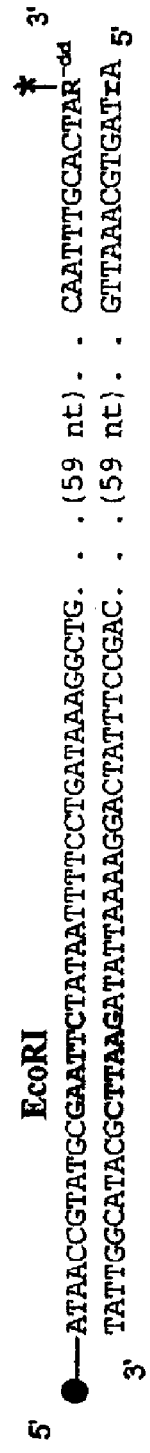
FIG. 7A
FIG. 7B

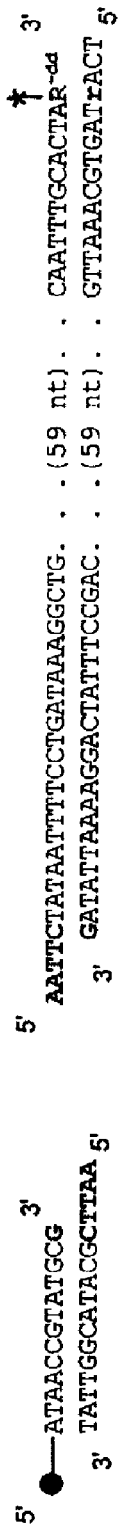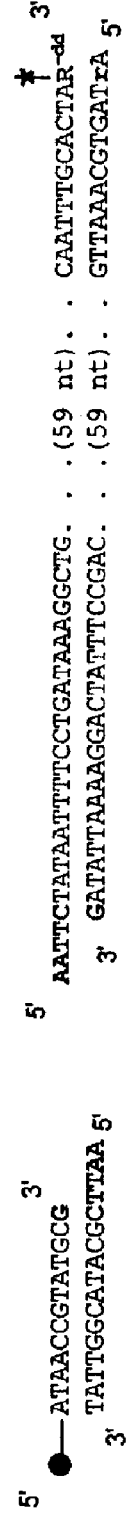
FIG. 8A
FIG. 8B

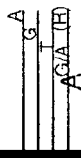
| Nucleotides | FIG. 9A | FIG. 9B | | FIG. 9C | FIG. 9D |
|---|---|---|---|---|---|
| SNP | HC21S00027 | TSC0095512 | TSC0095512 | TSC0264580 | HC21S00027 |
| Restriction enzyme site on second primer | BceA I | BceA I | BsmF I | BsmF I | BsmF I |
| 5' Overhang | 3'A T r A 5' | 3' G C s G 5' | 3' G C s GAA 5' | 3'T  10/14 cut A r CCC 5'<br>3'A  11/15 cut T A r CC 5' | 3'A  10/14 cut T r ACT 5'<br>3'T  11/15 cut AT r AC 5' |
| R | G/A | G/C | G/C | A/G | G/A |
| S | | | | | |

RAPID ANALYSIS OF VARIATIONS IN A GENOME

This appln claims benefit of 60/360,232 Mar. 1, 2002.

BACKGROUND OF THE INVENTION

1. Field of the Invention

The present invention is directed to a rapid method for determining the sequence of nucleic acid. The method is especially useful for genotyping, and for the detection of one to tens to hundreds to thousands of single nucleotide polymorphisms (SNPs) or mutations on single or on multiple chromosomes, and for the detection of chromosomal abnormalities, such as truncations, transversions, trisomies, and monosomies.

2. Background Art

Sequence variation among individuals comprises a continuum from deleterious disease mutations to neutral polymorphisms. There are more than three thousand genetic diseases currently known including Duchenne Muscular Dystrophy, Alzheimer's Disease, Cystic Fibrosis, and Huntington's Disease (D. N. Cooper and M. Krawczak, "Human Genome Mutations," BIOS Scientific Publishers, Oxford (1993)). Also, particular DNA sequences may predispose individuals to a variety of diseases such as obesity, arteriosclerosis, and various types of cancer, including breast, prostate, and colon. In addition, chromosomal abnormalities, such as trisomy 21, which results in Down's Syndrome, trisomy 18, which results in Edward's Syndrome, trisomy 13, which results in Patau Syndrome, monosomy X, which results in Turner's Syndrome, and other sex aneuploidies, account for a significant portion of the genetic defects in liveborn human beings. Knowledge of gene mutations, chromosomal abnormalities, and variations in gene sequences, such as single nucleotide polymorphisms (SNPs), will help to understand, diagnose, prevent, and treat diseases.

Most frequently, sequence variation is seen in differences in the lengths of repeated sequence elements, such as minisatellites and microsatellites, as small insertions or deletions, and as substitutions of the individual bases. Single nucleotide polymorphisms (SNPs) represent the most common form of sequence variation; three million common SNPs with a population frequency of over 5% have been estimated to be present in the human genome. Small deletions or insertions, which usually cause frameshift mutations, occur on average, once in every 12 kilobases of genomic DNA (Wang, D. G. et al., Science 280: 1077–1082 (1998)). A genetic map using these polymorphisms as a guide is being developed (http://research.marshfieldclinic.org/genetics/; internet address as of Jan. 10, 2002).

The nucleic acid sequence of the human genome was published in February, 2001, and provides a genetic map of unprecedented resolution, containing several hundred thousand SNP markers, and a potential wealth of information on human diseases (Venter et al., Science 291:1304–1351 (2001); International Human Genome Sequencing Consortium, Nature 409:860–921 (2001)). However, the length of DNA contained within the human chromosomes totals over 3 billion base pairs so sequencing the genome of every individual is impractical. Thus, it is imperative to develop high throughput methods for rapidly determining the presence of allelic variants of SNPs and point mutations, which predispose to or cause disease phenotypes. Efficient methods to characterize functional polymorphisms that affect an individual's physiology, psychology, audiology, ophthalmology, neurology, response to drugs, drug metabolism, and drug interactions also are needed.

Several techniques are widely used for analyzing and detecting genetic variations, such as DNA sequencing, restriction fragment length polymorphisms (RFLP), DNA hybridization assays, including DNA microarrays and peptide nucleic acid analysis, and the Protein Truncation Test (PTT), all of which have limitations. Although DNA sequencing is the most definitive method, it is also the most time consuming and expensive. Often, the entire coding sequence of a gene is analyzed even though only a small fraction of the coding sequence is of interest. In most instances, a limited number of mutations in any particular gene account for the majority of the disease phenotypes.

For example, the cystic fibrosis transmembrane conductance regulator (CFTR) gene is composed of 24 exons spanning over 250,000 base pairs (Rommens et al., Science 245:1059–1065 (1989); Riordan et al., Science 245:1066–73 (1989)). Currently, there are approximately 200 mutations in the CFTR gene that are associated with a disease state of Cystic Fibrosis. Therefore, only a very small percentage of the reading frame for the CFTR gene needs to be analyzed. Furthermore, a total of 10 mutations make up 75.1% of all known disease cases. The deletion of a single phenylalanine residue, F508, accounts for 66% of all Cystic Fibrosis cases in Caucasians.

Hybridization techniques, including Southern Blots, Slot Blots, Dot Blots, and DNA microarrays, are commonly used to detect genetic variations (Molecular Cloning, A Laboratory Manual, Cold Spring Harbor Laboratory Press, Third Edition (2001). In a typical hybridization assay, an unknown nucleotide sequence ("the target") is analyzed based on its affinity for another fragment with a known nucleotide sequence ("the probe"). If the two fragments hybridize under "stringent conditions," the sequences are thought to be complementary, and the sequence of the target fragment may be inferred from "the probe" sequence.

However, the results from a typical hybridization assay often are difficult to interpret. The absence or presence of a hybridization signal is dependent upon the definition of "stringent conditions." Any number of variables may be used to raise or lower stringency conditions such as salt concentration, the presence or absence of competitor nucleotide fragments, the number of washes performed to remove non-specific binding and the time and temperature at which the hybridizations are performed. Commonly, hybridization conditions must be optimized for each "target" nucleotide fragment, which is time-consuming, and inconsistent with a high throughput method. A high degree of variability is often seen in hybridization assays, as well as a high proportion of false positives. Typically, hybridization assays function as a screen for likely candidates but a positive confirmation requires DNA sequencing analysis.

Several techniques for the detection of mutations have evolved based on the principal of hybridization analysis. For example, in the primer extension assay, the DNA region spanning the nucleotide of interest is amplified by PCR, or any other suitable amplification technique. After amplification, a primer is hybridized to a target nucleic acid sequence, wherein the last nucleotide of the 3' end of the primer anneals immediately 5' to the nucleotide position on the target sequence that is to be analyzed. The annealed primer is extended by a single, labeled nucleotide triphosphate. The incorporated nucleotide is then detected.

There are several limitations to the primer extension assay. First, the region of interest must be amplified prior to primer extension, which increases the time and expense of the assay. Second, PCR primers and dNTPs must be completely removed before primer extension, and residual contaminants can interfere with the proper analysis of the results. Third, and the most restrictive aspect of the assay, is that the primer is hybridized to the DNA template, which requires optimization of conditions for each primer, and for each sequence that is analyzed. Hybridization assays have a low degree of reproducibility, and a high degree of non-specificity.

The Peptide Nucleic Acid (PNA) affinity assay is a derivative of traditional hybridization assays (Nielsen et al., Science 254:1497–1500 (1991); Egholm et al., J. Am. Chem. Soc. 114:1895–1897 (1992); James et al., Protein Science 3:1347–1350 (1994)). PNAs are structural DNA mimics that follow Watson-Crick base pairing rules, and are used in standard DNA hybridization assays. PNAs display greater specificity in hybridization assays because a PNA/DNA mismatch is more destabilizing than a DNA/DNA mismatch and complementary PNA/DNA strands form stronger bonds than complementary DNA/DNA strands. However, genetic analysis using PNAs still requires a laborious hybridization step, and as such, is subject to a high degree of non-specificity and difficulty with reproducibility.

Recently, DNA microarrays have been developed to detect genetic variations and polymorphisms (Taton et al., Science 289:1757–60, 2000; Lockhart et al., Nature 405:827–836 (2000); Gerhold et al., Trends in Biochemical Sciences 24:168–73 (1999); Wallace, R. W., Molecular Medicine Today 3:384–89 (1997); Blanchard and Hood, Nature Biotechnology 149:1649 (1996)). DNA microarrays are fabricated by high-speed robotics, on glass or nylon substrates, and contain DNA fragments with known identities ("the probe"). The microarrays are used for matching known and unknown DNA fragments ("the target") based on traditional base-pairing rules. The advantage of DNA microarrays is that one DNA chip may provide information on thousands of genes simultaneously. However, DNA microarrays are still based on the principle of hybridization, and as such, are subject to the disadvantages discussed above.

The Protein Truncation Test (PTT) is also commonly used to detect genetic polymorphisms (Roest et al., Human Molecular Genetics 2:1719–1721, (1993); Van Der Luit et al., Genomics 20:1–4 (1994); Hogervorst et al., Nature Genetics 10: 208–212 (1995)). Typically, in the PTT, the gene of interest is PCR amplified, subjected to in vitro transcription/translation, purified, and analyzed by polyacrylamide gel electrophoresis. The PTT is useful for screening large portions of coding sequence and detecting mutations that produce stop codons, which significantly diminish the size of the expected protein. However, the PTT is not designed to detect mutations that do not significantly alter the size of the protein.

Thus, a need still exists for a rapid method of analyzing DNA, especially genomic DNA suspected of having one or more single nucleotide polymorphisms or mutations.

BRIEF SUMMARY OF THE INVENTION

The invention is directed to a method for determining a sequence of a locus of interest, the method comprising: (a) amplifying a locus of interest on a template DNA using a first and second primers, wherein the second primer contains a recognition site for a restriction enzyme such that digestion with the restriction enzyme generates a 5' overhang containing the locus of interest; (b) digesting the amplified DNA with the restriction enzyme that recognizes the recognition site on the second primer; (c) incorporating a nucleotide into the digested DNA of (b) by using the 5' overhang containing the locus of interest as a template; and (d) determining the sequence of the locus of interest by determining the sequence of the DNA of (c).

The invention is also directed to a method for determining a sequence of a locus of interest, said method comprising: (a) amplifying a locus of interest on a template DNA using a first and second primers, wherein the second primer contains a portion of a recognition site for a restriction enzyme, wherein a full recognition site for the restriction enzyme is generated upon amplification of the template DNA such that digestion with the restriction enzyme generates a 5' overhang containing the locus of interest; (b) digesting the amplified DNA with the restriction enzyme that recognizes the full recognition site generated by the second primer and the template DNA; (c) incorporating a nucleotide into the digested DNA of (b) by using the 5' overhang containing the locus of interest as a template; and determining the sequence of the locus of interest by determining the sequence of the DNA of (c).

The template DNA can be obtained from any source including synthetic nucleic acid, preferably from a bacterium, fungus, virus, plant, protozoan, animal or human source. In one embodiment, the template DNA is obtained from a human source. In another embodiment, the template DNA is obtained from a cell, tissue, blood sample, serum sample, plasma sample, urine sample, spinal fluid, lymphatic fluid, semen, vaginal secretion, ascitic fluid, saliva, mucosa secretion, peritoneal fluid, fecal sample, or body exudates.

The 3' region of the first and/or second primer can contain a mismatch with the template DNA. The mismatch can occur at but is not limited to the last 1, 2, or 3 bases at the 3' end.

The restriction enzyme used in the invention can cut DNA at the recognition site. The restriction enzyme can be but is not limited to Pf1F I, Sau96 I, ScrF I, BsaJ I, Bssk I, Dde I, EcoN I, Fnu4H I, Hinf I, or Tth111 I. Alternatively, the restriction enzyme used in the invention can cut DNA at a distance from its recognition site.

In another embodiment, the first primer contains a recognition site for a restriction enzyme. In a preferred embodiment, the restriction enzyme recognition site is different from the restriction enzyme recognition site on the second primer. The invention includes digesting the amplified DNA with a restriction enzyme that recognizes the recognition site on the first primer.

Preferably, the recognition site on the second primer is for a restriction enzyme that cuts DNA at a distance from its recognition site and generates a 5' overhang, containing the locus of interest. In a preferred embodiment, the recognition site on the second primer is for a Type IIS restriction enzyme. The Type IIS restriction enzyme, e.g., is selected from the group consisting of: Alw I, Alw26 I, Bbs I, Bbv I, BceA I, Bmr I, Bsa I, Bst71 I, BsmA I, BsmB I, BsmF I, BspM I, Ear I, Fau I, Fok I, Hga I, Ple I, Sap I, SSfaN I, and Sthi32 I, and more preferably BceA I and BsmF I.

In one embodiment, the 5' region of the second primer does not anneal to the template DNA and/or the 5' region of the first primer does not anneal to the template DNA. The annealing length of the 3' region of the first or second primer can be 25–20, 20–15, 15, 14, 13, 12, 11, 10, 9, 8, 7, 6, 5, 4, or less than 4 bases.

In one embodiment, the amplification can comprise polymerase chain reaction (PCR). In a further embodiment, the annealing temperature for cycle 1 of PCR can be at about the melting temperature of the 3' region of the second primer that anneals to the template DNA. In another embodiment, the annealing temperature for cycle 2 of PCR can be about the melting temperature of the 3' region of the first primer that anneals to the template DNA. In another embodiment, the annealing temperature for the remaining cycles can be about the melting temperature of the entire sequence of the second primer.

In one embodiment, the 3' end of the second primer is adjacent to the locus of interest.

The first and/or second primer can contain a tag at the 5' terminus.

Preferably, the first primer contains a tag at the 5' terminus. The tag can be used to separate the amplified DNA from the template DNA. The tag can be used to separate the amplified DNA containing the labeled nucleotide from the amplified DNA that does not contain the labeled nucleotide. The tag can be but is not limited to a radioisotope, fluorescent reporter molecule, chemiluminescent reporter molecule, antibody, antibody fragment, hapten, biotin, derivative of biotin, photobiotin, iminobiotin, digoxigenin, avidin, enzyme, acridinium, sugar, enzyme, apoenzyme, homopolymeric oligonucleotide, hormone, ferromagnetic moiety, paramagnetic moiety, diamagnetic moiety, phosphorescent moiety, luminescent moiety, electrochemiluminescent moiety, chromatic moiety, moiety having a detectable electron spin resonance, electrical capacitance, dielectric constant or electrical conductivity, or combinations thereof. Preferably, the tag is biotin. The biotin tag is used to separate amplified DNA from the template DNA using a streptavidin matrix. The streptavidin matrix is coated on wells of a microtiter plate.

The incorporation of a nucleotide in the method of the invention is by a DNA polymerase including but not limited to E. coli DNA polymerase, Klenow fragment of E. coli DNA polymerase I, T5 DNA polymerase, T7 DNA polymerase, T4 DNA polymerase, Taq polymerase, Pfu DNA polymerase, Vent DNA polymerase and sequenase.

The incorporation of a nucleotide can further comprise using a mixture of labeled and unlabeled nucleotides. One nucleotide, two nucleotides, three nucleotides, four nucleotides, five nucleotides, or more than five nucleotides may be incorporated. A combination of labeled and unlabeled nucleotides can be incorporated. The labeled nucleotide can be but is not limited to a dideoxynucleotide triphosphate and deoxynucleotide triphosphate. The unlabeled nucleotide can be but is not limited to a dideoxynucleotide triphosphate and deoxynucleotide triphosphate. The labeled nucleotide is labeled with a molecule such as but not limited to a radioactive molecule, fluorescent molecule, antibody, antibody fragment, hapten, carbohydrate, biotin, and derivative of biotin, phosphorescent moiety, luminescent moiety, electrochemiluminescent moiety, chromatic moiety, or moiety having a detectable electron spin resonance, electrical capacitance, dielectric constant or electrical conductivity. Preferably, the labeled nucleotide is labeled with a fluorescent molecule. The incorporation of a fluorescent labeled nucleotide further includes using a mixture of fluorescent and unlabeled nucleotides.

In one embodiment, the determination of the sequence of the locus of interest comprises detecting the incorporated nucleotide. In one embodiment, the detection is by a method such as but not limited to gel electrophoresis, capillary electrophoresis, microchannel electrophoresis, polyacrylamide gel electrophoresis, fluorescence detection, sequencing, ELISA, mass spectrometry, time of flight mass spectrometry, quadrupole mass spectrometry, magnetic sector mass spectrometry, electric sector mass spectrometry, fluorometry, infrared spectrometry, ultraviolet spectrometry, palentiostatic amperometry, hybridization, such as Southern Blot, or microarray. In a preferred embodiment, the detection is by fluorescence detection.

In a preferred embodiment, the locus of interest is suspected of containing a single nucleotide polymorphism or mutation. The method can be used for determining sequences of multiple loci of interest concurrently. The template DNA can comprise multiple loci from a single chromosome. The template DNA can comprise multiple loci from different chromosomes. The loci of interest on template DNA can be amplified in one reaction. Alternatively, each of the loci of interest on template DNA can be amplified in a separate reaction. The amplified DNA can be pooled together prior to digestion of the amplified DNA. Each of the labeled DNA containing a locus of interest can be separated prior to determining the sequence of the locus of interest. In one embodiment, at least one of the loci of interest is suspected of containing a single nucleotide polymorphism or a mutation.

In another embodiment, the method of the invention can be used for determining the sequences of multiple loci of interest from a single individual or from multiple individuals. Also, the method of the invention can be used to determine the sequence of a single locus of interest from multiple individuals.

The first primer is shown modified with biotin at the 5' end to aid in purification. The sequence of the 3' end of the primers is such that the primers anneal at a desired distance upstream and downstream of the locus of interest. The second primer anneals close to the locus of interest; the annealing site, which is depicted as region "c," is designed such that the 3' end of the second primer anneals one base away from the locus of interest. The second primer can anneal any distance from the locus of interest provided that digestion with the restriction enzyme, which recognizes the region "d" on this primer, generates a 5' overhang that contains the locus of interest.

The first primer annealing site, which is depicted as region "b," is about 20 bases.

Figure 1A:
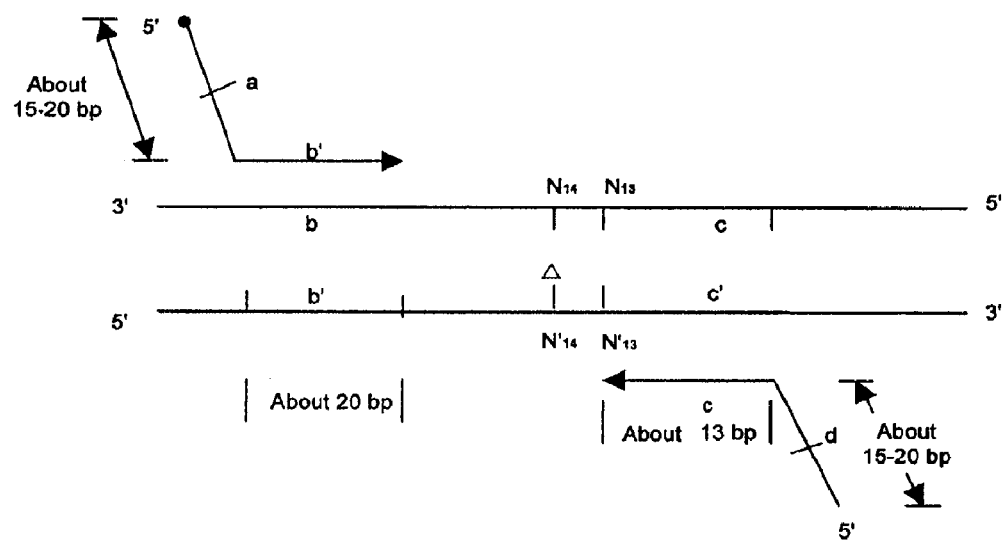
FIG. 1A. A Schematic diagram depicting a double stranded DNA molecule. A pair of primers, depicted as bent arrows, flank the locus of interest, depicted as a triangle symbol at base N14. The locus of interest can be a single nucleotide polymorphism, point mutation, insertion, deletion, translocation, etc. Each primer contains a restriction enzyme recognition site about 10 bp from the 5' terminus depicted as region "a" in the first primer and as region "d" in the second primer. Restriction recognition site "a" can be for any type of restriction enzyme but recognition site "d" is for a restriction enzyme, which cuts "n" nucleotides away from its recognition site and leaves a 5' overhang and a recessed 3' end. Examples of such enzymes include but are not limited to BceA I and BsmF I. The 5' overhang serves as a template for incorporation of a nucleotide into the 3' recessed end.
Figure 1B:
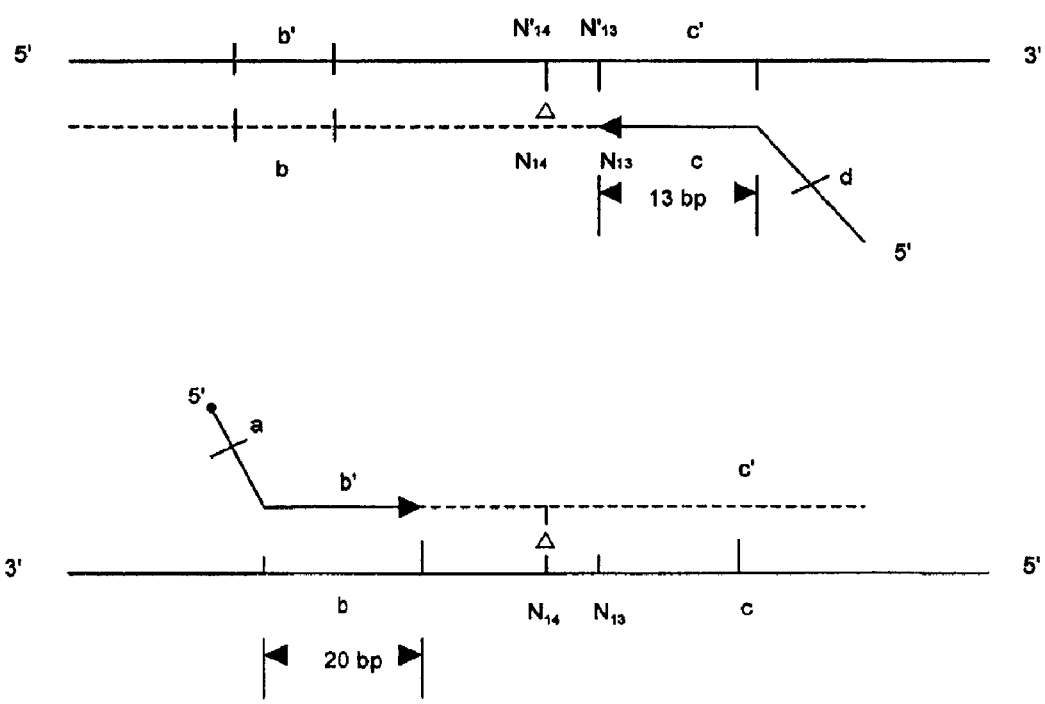

FIG. 1B. A schematic diagram depicting the annealing and extension steps of the first cycle of amplification by PCR. The first cycle of amplification is performed at about the melting temperature of the 3' region, which anneals to the template DNA, of the second primer, depicted as region "c," and is 13 base pairs in this example. At this temperature, both the first and second primers anneal to their respective complementary strands and begin extension, depicted by dotted lines. In this first cycle, the second primer extends and copies the region b where the first primer can anneal in the next cycle.

FIG. 1C. A schematic diagram depicting the annealing and extension steps following denaturation in the second cycle of amplification of PCR. The second cycle of amplification is performed at a higher annealing temperature (TM2), which is about the melting temperature of the 20 bp of the 3' region of the first primer that anneals to the template DNA, depicted as region "b." Therefore at TM2, the first primer, which is complementary to region b, can bind to the DNA that was copied in the first cycle of the reaction. However, at TM2 the second primer cannot anneal to the original template DNA or to DNA that was copied in the first cycle of the reaction because the annealing temperature is too high. The second primer can anneal to 13 bases in the original template DNA but TM2 is calculated at about the melting temperature of 20 bases.

Figure 1D:
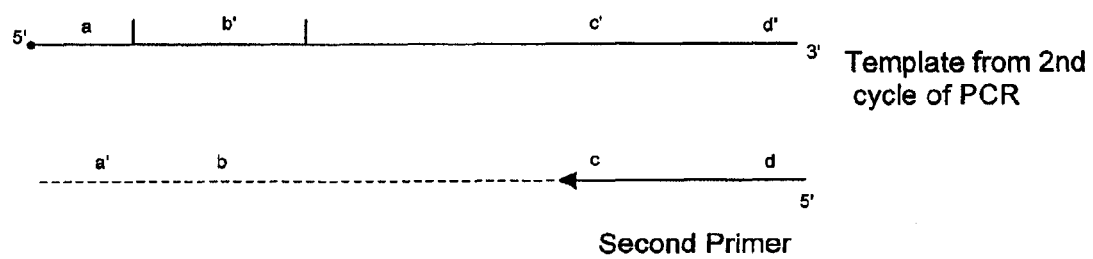

FIG. 1D. A schematic diagram depicting the annealing and extension reactions after denaturation during the third cycle of amplification. In this cycle, the annealing temperature, TM3, is about the melting temperature of the entire second primer, including regions "c" and "d." The length of regions "c"+"d" is about 27–33 bp long, and thus TM3 is significantly higher than TM1 and TM2. At this higher TM the second primer, which contain region c and d, anneals to the copied DNA generated in cycle 2.

Figure 1E:
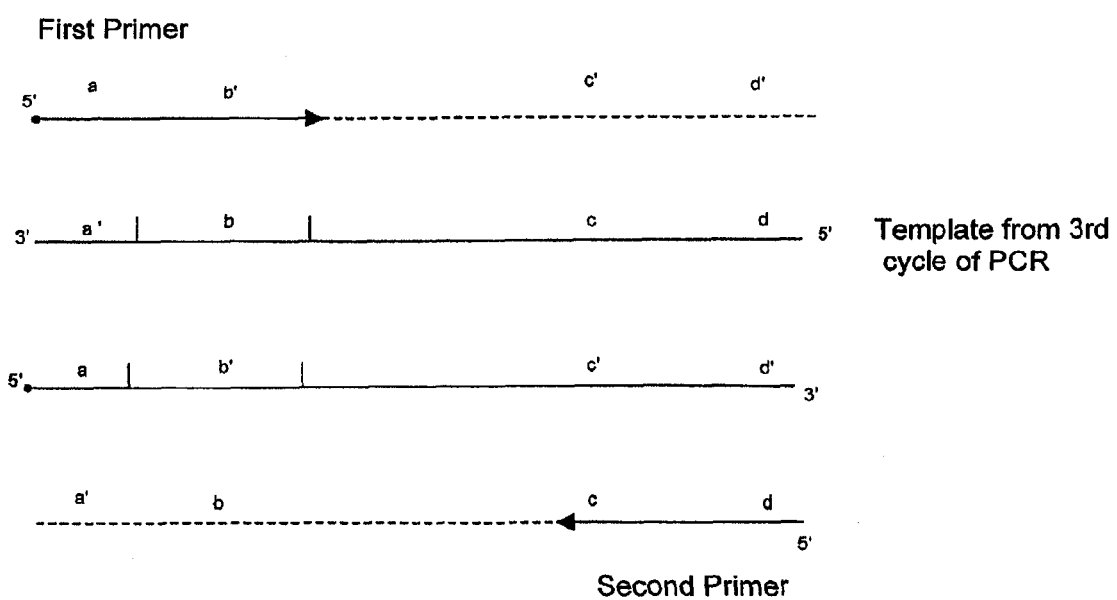

FIG. 1E. A schematic diagram depicting the annealing and extension reactions for the remaining cycles of amplification. The annealing temperature for the remaining cycles is TM3, which is about the melting temperature of the entire second primer. At TM3, the second primer binds to templates that contain regions c' and d' and the first primer binds to templates that contain regions a' and b. By raising the annealing temperature successively in each cycle for the first three cycles, from TM1 to TM2 to TM3, nonspecific amplification is significantly reduced.

Figure 1F:
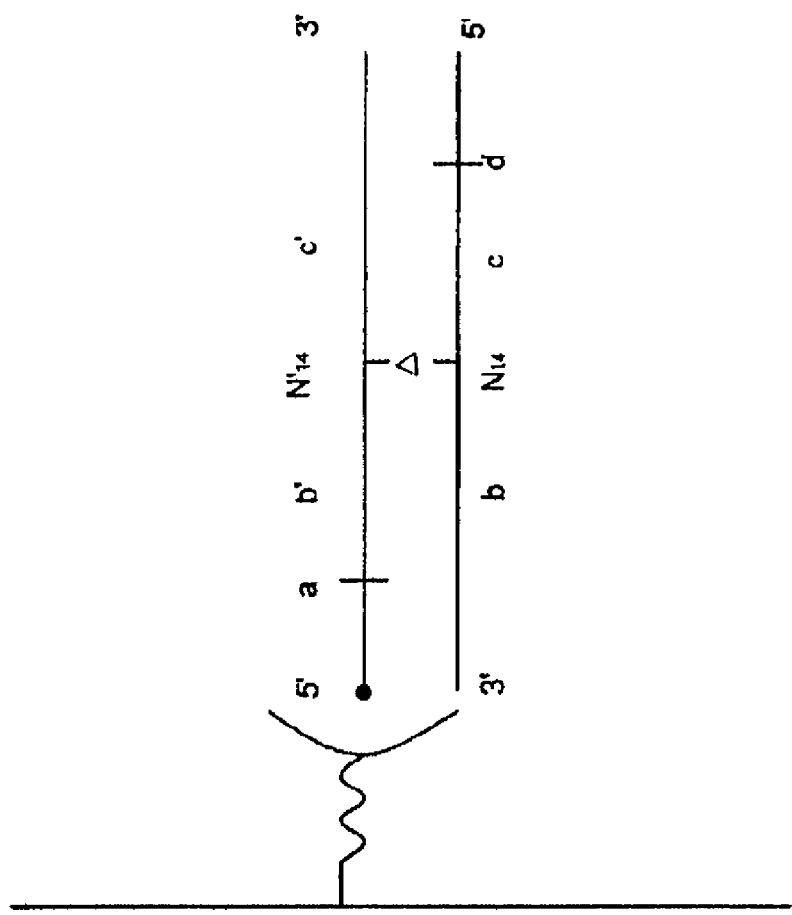

FIG. 1F. A schematic diagram depicting the amplified locus of interest bound to a solid matrix.

Figure 1G:
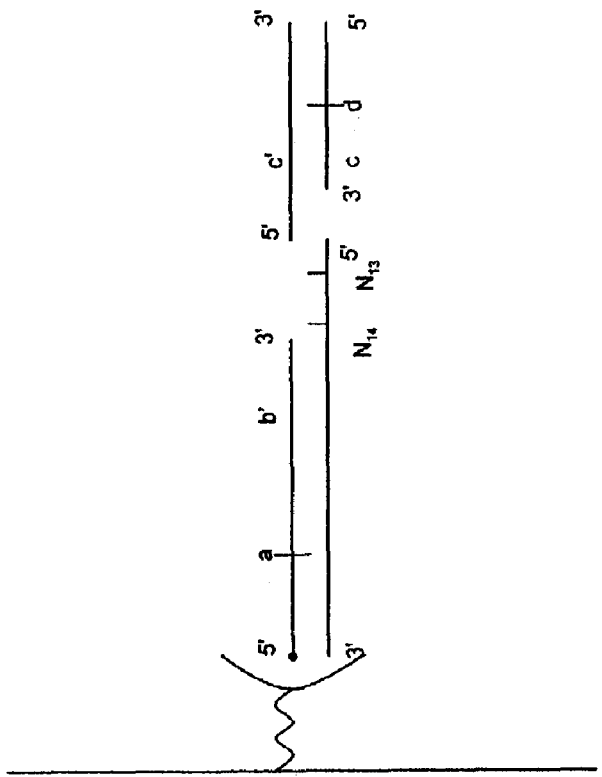

FIG. 1G. A schematic diagram depicting the bound, amplified DNA after digestion with a restriction enzyme that recognizes "d." The "downstream" end is released into the supernatant, and can be removed by washing with any suitable buffer. The upstream end containing the locus of interest remains bound to the solid matrix.

Figure 1H:
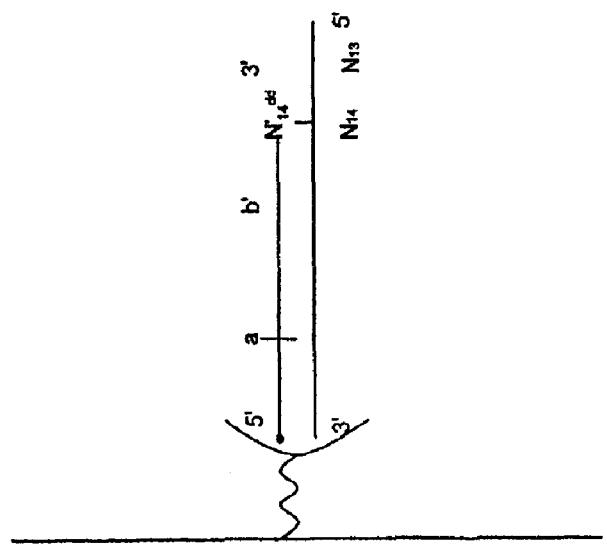

FIG. 1H. A schematic diagram depicting the bound amplified DNA, after "filling in" with a labeled ddNTP. A DNA polymerase is used to "fill in" the base ($N'_{14}$) that is complementary to the locus of interest ($N_{14}$). In this example, only ddNTPs are present in this reaction, such that only the locus of interest or SNP of interest is filled in.

Figure 1I:
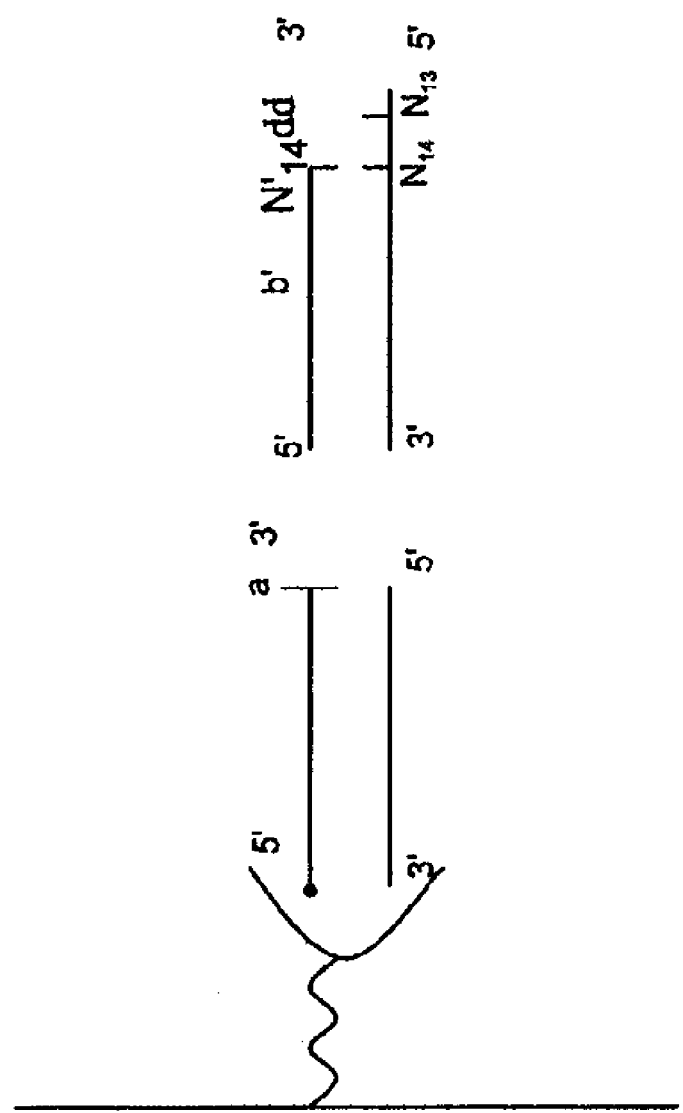

FIG. 1I. A schematic diagram depicting the labeled, bound DNA after digestion with restriction enzyme "a." The labeled DNA is released into the supernatant, which can be collected to identify the base that was incorporated.

Figure 2:
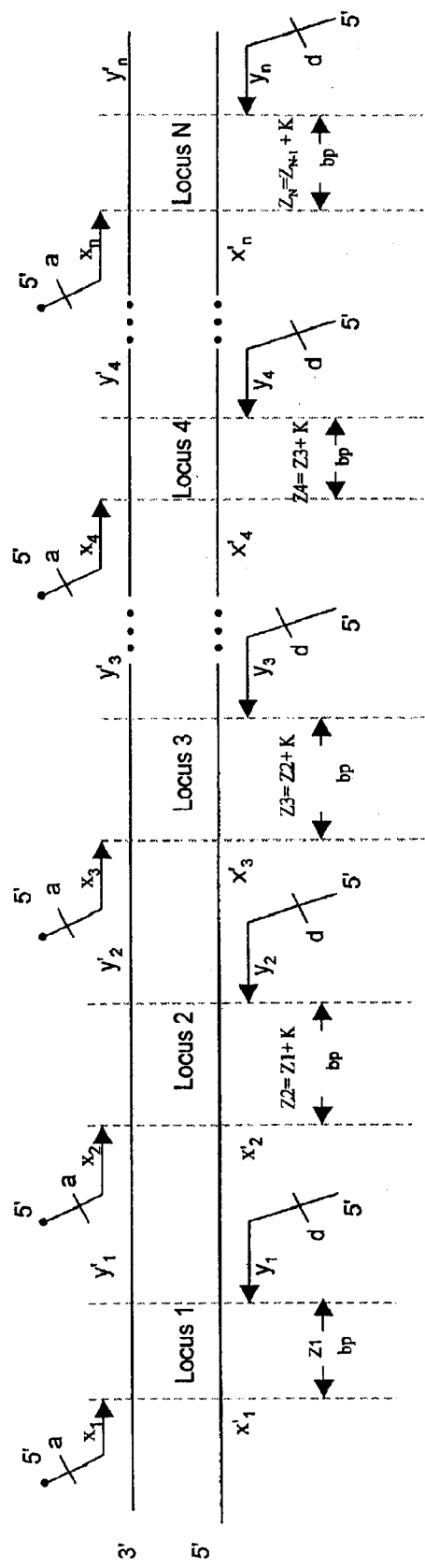
Figure 5A:
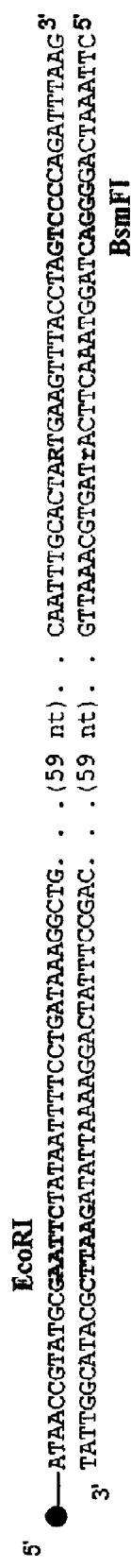
Figure 5B:
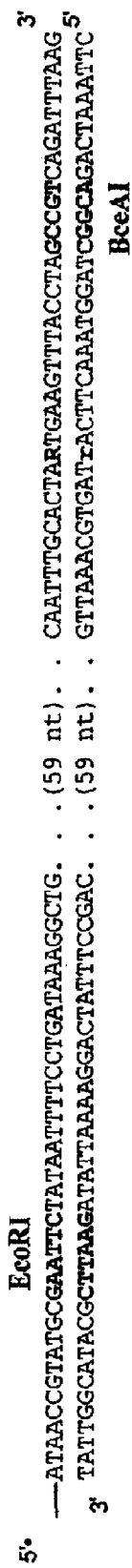
Figure 5C:
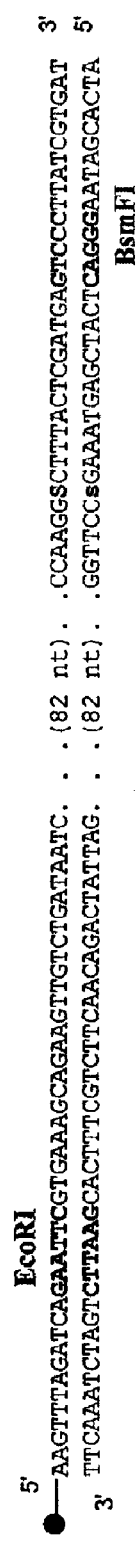
Figure 5D:
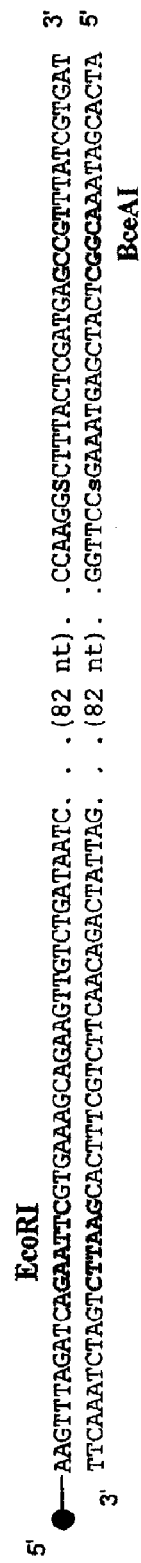

FIG. 2. A schematic diagram depicting double stranded DNA templates with "N" number of loci of interest and "n" number of primer pairs, $x_1$, $y_1$, to $x_n$, $y_n$, specifically annealed such that a primer flanks each locus of interest. The first primers are biotinylated at the 5' end, depicted by ●, and contain a restriction enzyme recognition site, "a", which is recognized by any type of restriction enzyme. The second primers contain a restriction enzyme recognition site, "d," where "d" is a recognition site for a restriction enzyme that cuts DNA at a distance from its recognition site, and generates a 5' overhang containing the locus of interest and a recessed 3' end. The second primers anneal adjacent to the respective loci of interest. The exact position of the restriction enzyme site "d" in the second primers is designed such that digesting the PCR product of each locus of interest with restriction enzyme "d" generates a 5' overhang containing the locus of interest and a 3' recessed end. The annealing sites of the first primers are about 20 bases long and are selected such that each successive first primer is further away from its respective second primer. For example, if at locus 1 the 3' ends of the first and second primers are Z base pairs apart, then at locus 2, the 3' ends of the first and second primers are Z+K base pairs apart, where K=1, 2, 3 or more than three bases. Primers for locus N are $Z_{N-1}$+K base pairs apart. The purpose of making each successive first primer further apart from their respective second primers is such that the "filled in" restriction fragments (generated after amplification, purification, digestion and labeling as described in FIGS. 1B–1I) differ in size and can be resolved, for example by electrophoresis, to allow detection of each individual locus of interest.

FIG. 3. PCR amplification of SNPs using multiple annealing temperatures. A sample containing genomic DNA templates from thirty-six human volunteers was analyzed for the following four SNPs: SNP HC21S00340 (lane 1), identification number as assigned in the Human Chromosome 21 cSNP Database, located on chromosome 21; SNP TSC 0095512 (lane 2), located on chromosome 1; SNP TSC 0214366 (lane 3), located on chromosome 1; and SNP TSC 0087315 (lane 4), located on chromosome 1. Each SNP was amplified by PCR using three different annealing temperature protocols, herein referred to as the low stringency annealing temperature; medium stringency annealing temperature; and high stringency annealing temperature. Regardless of the annealing temperature protocol, each SNP was amplified for 40 cycles of PCR. The denaturation step for each PCR reaction was performed for 30 seconds at 95° C.

FIG. 3A. Photograph of a gel demonstrating PCR amplification of the 4 different SNPs using the low stringency annealing temperature protocol.

FIG. 3B. Photograph of a gel demonstrating PCR amplification of the 4 different SNPs using the medium stringency annealing temperature protocol.

FIG. 3C. Photograph of a gel demonstrating PCR amplification of the 4 different SNPs using the high stringency annealing temperature protocol.

FIG. 4A. A depiction of the DNA sequence of SNP HC21S00027 (SEQ ID NOS:27 & 28), assigned by the Human Chromosome 21 cSNP database, located on chromosome 21. A first primer (SEQ ID NO:17) and a second primer (SEQ ID NO:18) are indicated above and below, respectively, the sequence of HC21S00027. The first primer is biotinylated and contains the restriction enzyme recognition site for EcoRI. The second primer contains the restriction enzyme recognition site for BsmF I and contains 13 bases that anneal to the DNA sequence. The SNP is indicated by R (A/G) and r (T/C; complementary to R).

FIG. 4B. A depiction of the DNA sequence of SNP HC21S00027 (SEQ ID NOS:27 & 28), as assigned by the Human Chromosome 21 cSNP database, located on chromosome 21. A first primer (SEQ ID NO:17) and a second primer (SEQ ID NO:19) are indicated above and below, respectively, the sequence of HC21S00027. The first primer is biotinylated and contains the restriction enzyme recognition site for EcoRI. The second primer contains the restriction enzyme recognition site for BceAI and has 13 bases that anneal to the DNA sequence. The SNP is indicated by R (A/G) and r (T/C; complementary to R).

FIG. 4C. A depiction of the DNA sequence of SNP TSC0095512 (SEQ ID NOS:29 & 30) from chromosome 1. The first primer (SEQ ID NO:11) and the second primer (SEQ ID NO:20) are indicated above and below, respectively, the sequence of TSC0095512. The first primer is biotinylated and contains the restriction enzyme recognition site for EcoRI. The second primer contains the restriction enzyme recognition site for BsmF I and has 13 bases that anneal to the DNA sequence. The SNP is indicated by S (G/C) and s (C/G; complementary to S).

FIG. 4D. A depiction of the DNA sequence of SNP TSC0095512 (SEQ ID NOS:29 & 30) from chromosome 1. The first primer (SEQ ID NO:11) and the second primer (SEQ ID NO:12) are indicated above and below, respectively, the sequence of TSC0095512. The first primer is biotinylated and contains the restriction enzyme recognition site for EcoRI. The second primer contains the restriction enzyme recognition site for BceAI and has 13 bases that anneal to the DNA sequence. The SNP is indicated by S (G/C) and s (C/G; complementary to S).

FIGS. 5A–5D. A schematic diagram depicting the nucleotide sequences of SNP HC21S00027 (FIG. 5A (SEQ ID NOS:31 & 32) and FIG. 5B (SEQ ID NOS:31 & 33)), and SNP TSC0095512 (FIG. 5C (SEQ ID NOS:34 & 35) and FIG. 5D (SEQ ID NOS:34 & 36)) after amplification with the primers described in FIGS. 4A–4D. Restriction sites in the primer sequence are indicated in bold.

Figure 6A:
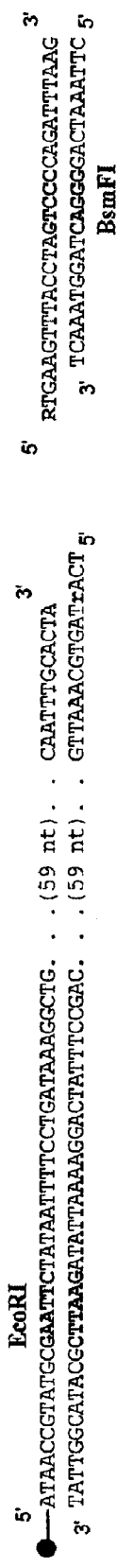

FIGS. 6A–6D. A schematic diagram depicting the nucleotide sequences of each amplified SNP after digestion with the appropriate Type IIS restriction enzyme. FIG. 6A (SEQ ID NOS:31 & 32) and FIG. 6B (SEQ ID NOS:31 & 33) depict fragments of SNP HC21S00027 digested with the Type IIS restriction enzymes BsmF I and BceA I, respectively. FIG. 6C (SEQ ID NOS:34 & 35) and FIG. 6D (SEQ ID NOS:34 & 36) depict fragments of SNP TSC0095512 digested with the Type IIS restriction enzymes BsmF I and BceA I, respectively.

Figure 7C:
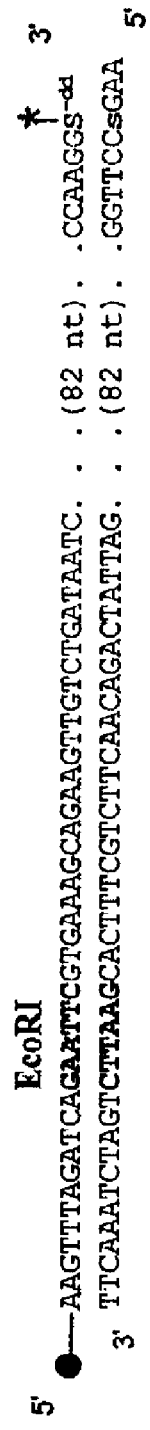
Figure 7D:
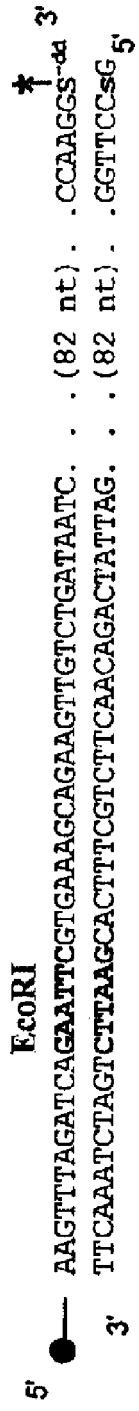

FIGS. 7A–7D. A schematic diagram depicting the incorporation of a fluorescently labeled nucleotide using the 5' overhang of the digested SNP site as a template to "fill in" the 3' recessed end. FIG. 7A (SEQ ID NOS:31, 37 & 41) and FIG. 7B (SEQ ID NOS:31, 37 & 39) depict the digested SNP HC21S00027 locus with an incorporated labeled ddNTP ($*R^{-dd}$=fluorescent dideoxy nucleotide). FIG. 7C (SEQ ID NOS:34 & 38) and FIG. 7D (SEQ ID NO:34) depict the digested SNP TSC0095512 locus with an incorporated labeled ddNTP ($*S^{-dd}$=fluorescent dideoxy nucleotide). The use of ddNTPs ensures that the 3' recessed end is extended by one nucleotide, which is complementary to the nucleotide of interest or SNP site present in the 5' overhang.

Figure 7E:
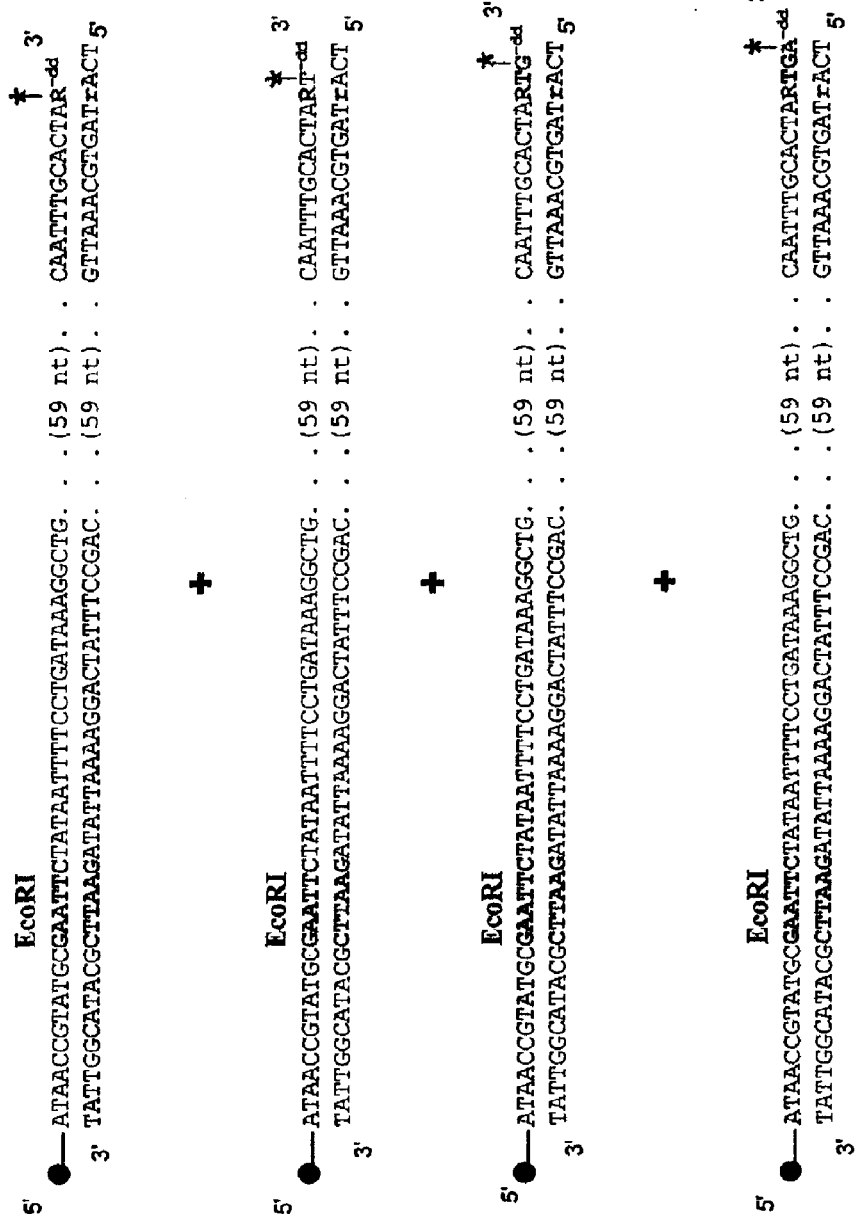

FIG. 7E. A schematic diagram depicting the incorporation of dNTPs and a ddNTP into the 5' overhang containing the SNP site. SNP HC21S00007 was digested with BsmF I, which generates a four base 5' overhang. The use of a mixture of dNTPs and ddNTPs allows the 3' recessed end to be extended one nucleotide (a ddNTP is incorporated first) (SEQ ID NOS:31, 37 & 41); two nucleotides (a dNTP is incorporated followed by a ddNTP) (SEQ ID NOS:31, 39 & 41); three nucleotides (two dNTPs are incorporated, followed by a ddNTP) (SEQ ID NOS:31, 40 & 41); or four nucleotides (three dNTPs are incorporated, followed by a ddNTP) (SEQ ID NOS:31 & 41). All four products can be separated by size, and the incorporated nucleotide detected ($*R^{-dd}$=fluorescent dideoxy nucleotide). Detection of the first nucleotide, which corresponds to the SNP or locus site, and the next three nucleotides provides an additional level of quality assurance. The SNP is indicated by R (A/G) and r (T/C) (complementary to R).

Figure 8C:
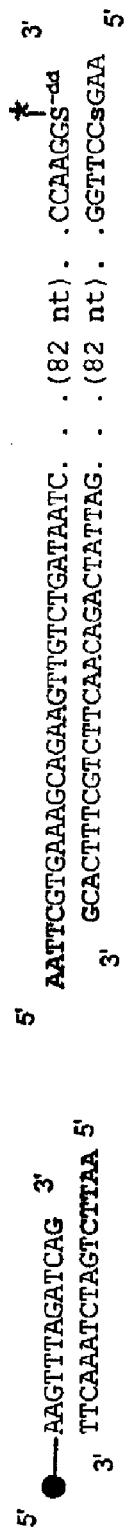
Figure 8D:
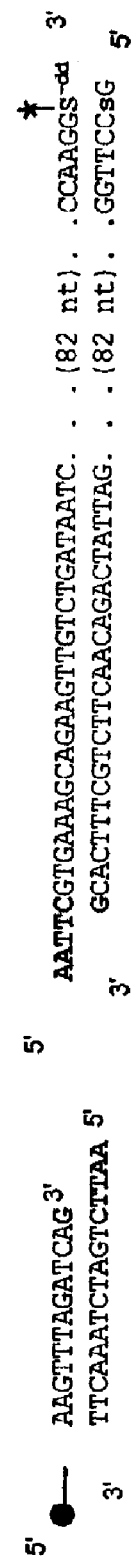

FIGS. 8A–8D. Release of the "filled in" SNP from the solid support matrix, i.e. streptavidin coated well. SNP HC21S00027 is shown in FIG. 8A (SEQ ID NOS:31, 37 & 41) and FIG. 8B (SEQ ID NOS:31, 37 & 39), while SNP TSC0095512 is shown in FIG. 8C (SEQ ID NOS:34 & 38) and FIG. 8D (SEQ ID NO:34). The "filled in" SNP is free in solution, and can be detected.

FIG. 9A. Sequence analysis of SNP HC21S00027 digested with BceAI. Four "fill in" reactions are shown; each reaction contained one fluorescently labeled nucleotide, ddGTP, ddATP, ddTTP, or ddCTP, and unlabeled ddNTPs. The 5' overhang generated by digestion with BceA I and the expected nucleotides at this SNP site are indicated.

FIG. 9B. Sequence analysis of SNP TSC0095512. SNP TSC0095512 was amplified with a second primer that contained the recognition site for BceA I, and in a separate reaction, with a second primer that contained the recognition site for BsmF I. Four fill in reactions are shown for each PCR product; each reaction contained one fluorescently labeled nucleotide, ddGTP, ddATP, ddTTP, or ddCTP, and unlabeled ddNTPs. The 5' overhang generated by digestion with BceA I and with BsmF I and the expected nucleotides are indicated.

FIG. 9C. Sequence analysis of SNP TSC0264580 after amplification with a second primer that contained the recognition site for BsmF I. Four "fill in" reactions are shown; each reaction contained one fluorescently labeled nucleotide, which was ddGTP, ddATP, ddTTP, or ddCTP and unlabeled ddNTPs. Two different 5' overhangs are depicted: one represents the DNA molecules that were cut 11 nucleotides away on the sense strand and 15 nucleotides away on the antisense strand and the other represents the DNA molecules that were cut 10 nucleotides away on the sense strand and 14 nucleotides away on the antisense strand. The expected nucleotides also are indicated.

FIG. 9D. Sequence analysis of SNP HC21S00027 amplified with a second primer that contained the recognition site for BsmF I. A mixture of labeled ddNTPs and unlabeled dNTPs was used to fill in the 5' overhang generated by digestion with BsmF I. Two different 5' overhangs are depicted: one represents the DNA molecules that were cut 11 nucleotides away on the sense strand and 15 nucleotides away on the antisense strand and the other represents the DNA molecules that were cut 10 nucleotides away on the sense strand and 14 nucleotides away on the antisense strand. The nucleotide upstream of the SNP, the nucleotide at the SNP site (the sample contained DNA templates from 36 individuals; both nucleotides would be expected to be represented in the sample), and the three nucleotides downstream of the SNP are indicated.

Figure 10:

FIG. 10. Sequence analysis of multiple SNPs. SNPs HC21S00131, and HC21S00027, which are located on chromosome 21, and SNPs TSC0087315, SNP TSC0214366, SNP TSC0413944, and SNP TSC0095512, which are on chromosome 1, were amplified in separate PCR reactions with second primers that contained a recognition site for BsmF I. The primers were designed so that each amplified locus of interest was of a different size. After amplification, the reactions were pooled into a single sample, and all subsequent steps of the method performed (as described for FIGS. 1F–1I) on that sample. Each SNP and the nucleotide found at each SNP are indicated.

DETAILED DESCRIPTION OF THE INVENTION

The present invention provides a novel method for rapidly determining the sequence of DNA, especially at a locus of interest or multiple loci of interest. The sequences of any number of DNA targets, from one to hundreds or thousands or more of loci of interest in any template DNA or sample of nucleic acid can be determined efficiently, accurately, and economically. The method is especially useful for the rapid sequencing of one to tens of thousands or more of genes, regions of genes, fragments of genes, single nucleotide polymorphisms, and mutations on a single chromosome or on multiple chromosomes.

The invention is directed to a method for determining a sequence of a locus of interest, the method comprising: (a) amplifying a locus of interest on a template DNA using a first and second primers, wherein the second primer contains a recognition site for a restriction enzyme such that digestion with the restriction enzyme generates a 5' overhang containing the locus of interest; (b) digesting the amplified DNA with the restriction enzyme that recognizes the recognition site on the second primer; (c) incorporating a nucleotide into the digested DNA of (b) by using the 5' overhang containing the locus of interest as a template; and (d) determining the sequence of the locus of interest by determining the sequence of the DNA of (c).

The invention is also directed to a method for determining a sequence of a locus of interest, said method comprising: (a) amplifying a locus of interest on a template DNA using a first and second primers, wherein the first and/or second primer contains a portion of a recognition site for a restriction enzyme, wherein a full recognition site for the restriction enzyme is generated upon amplification of the template DNA such that digestion with the restriction enzyme generates a 5' overhang containing the locus of interest; (b) digesting the amplified DNA with the restriction enzyme that recognizes the full recognition site generated by the second primer and the template DNA; (c) incorporating a nucleotide into the digested DNA of (b) by using the 5' overhang containing the locus of interest as a template; and determining the sequence of the locus of interest by determining the sequence of the DNA of (c).

DNA Template

By a "locus of interest" is intended a selected region of nucleic acid that is within a larger region of nucleic acid. A locus of interest can include but is not limited to 1–100, 1–50, 1–20, or 1–10 nucleotides, preferably 1–6, 1–5, 1–4, 1–3, 1–2, or 1 nucleotide(s).

The term "template" refers to any nucleic acid molecule that can be used for amplification in the invention. RNA or DNA that is not naturally double stranded can be made into double stranded DNA so as to be used as template DNA. Any double stranded DNA or preparation containing multiple, different double stranded DNA molecules can be used as template DNA to amplify a locus or loci of interest contained in the template DNA.

The source of the nucleic acid for obtaining the template DNA can be from any appropriate source including but not limited to nucleic acid from any organism, e.g., human or nonhuman, e.g., bacterium, virus, yeast, fungus, plant, protozoan, animal, nucleic acid-containing samples of tissues, bodily fluids (for example, blood, serum, plasma, saliva, urine, tears, semen, vaginal secretions, lymph fluid, cerebrospinal fluid or mucosa secretions), fecal matter, individual cells or extracts of the such sources that contain the nucleic acid of the same, and subcellular structures such as mitochondria or chloroplasts, using protocols well established within the art. Nucleic acid can also be obtained from forensic, food, archaeological, or inorganic samples onto which nucleic acid has been deposited or extracted. In a preferred embodiment, the nucleic acid has been obtained from a human or animal to be screened for the presence of one or more genetic sequences that can be diagnostic for, or predispose the subject to, a medical condition or disease.

The nucleic acid that is to be analyzed can be any nucleic acid, e.g., genomic, plasmid, cosmid, yeast artificial chromosomes, artificial or man-made DNA, including unique DNA sequences, and also DNA that has been reverse transcribed from an RNA sample, such as cDNA. The sequence of RNA can be determined according to the invention if it is capable of being made into a double stranded DNA form to be used as template DNA.

The terms "primer" and "oligonucleotide primer" are interchangeable when used to discuss an oligonucleotide that anneals to a template and can be used to prime the synthesis of a copy of that template.

"Amplified" DNA is DNA that has been "copied" once or multiple times, e.g. by polymerase chain reaction. When a large amount of DNA is available to assay, such that a sufficient number of copies of the locus of interest are already present in the sample to be assayed, it may not be necessary to "amplify" the DNA of the locus of interest into an even larger number of replicate copies. Rather, simply "copying" the template DNA once using a set of appropriate primers, such as those containing hairpin structures that allow the restriction enzyme recognition sites to be double stranded, can suffice.

"Copy" as in "copied DNA" refers to DNA that has been copied once, or DNA that has been amplified into more than one copy.

In one embodiment, the nucleic acid is amplified directly in the original sample containing the source of nucleic acid. It is not essential that the nucleic acid be extracted, purified or isolated; it only needs to be provided in a form that is capable of being amplified. A hybridization step of the nucleic acid with the primers, prior to amplification, is not required. For example, amplification can be performed in a cell or sample lysate using standard protocols well known in the art. DNA that is on a solid support, in a fixed biological preparation, or otherwise in a composition that contains non-DNA substances and that can be amplified without first being extracted from the solid support or fixed preparation or non-DNA substances in the composition can be used directly, without further purification, as long as the DNA can anneal with appropriate primers, and be copied, especially amplified, and the copied or amplified products can be recovered and utilized as described herein.

In a preferred embodiment, the nucleic acid is extracted, purified or isolated from non-nucleic acid materials that are in the original sample using methods known in the art prior to amplification.

In another embodiment, the nucleic acid is extracted, purified or isolated from the original sample containing the source of nucleic acid and prior to amplification, the nucleic acid is fragmented using any number of methods well known in the art including but not limited to enzymatic digestion, manual shearing, and sonication. For example, the DNA can be digested with one or more restriction enzymes that have a recognition site, and especially an eight base or six base pair recognition site, which is not present in the loci of interest. Typically, DNA can be fragmented to any desired length, including 50, 100, 250, 500, 1,000, 5,000, 10,000, 50,000 and 100,000 base pairs long. In another embodiment, the DNA is fragmented to an average length of about 1000 to 2000 base pairs. However, it is not necessary that the DNA be fragmented.

Fragments of DNA that contain the loci of interest can be purified from the fragments of DNA that do not contain the loci of interest before amplification. The purification can be done by using primers that will be used in the amplification (see "Primer Design" section below) as hooks to retrieve the fragments containing the loci of interest, based on the ability of such primers to anneal to the loci of interest. In a preferred embodiment, tag-modified primers are used, such as e.g. biotinylated primers. See also the "Purification of Amplified DNA" section for additional tags.

By purifying the DNA fragments containing the loci of interest, the specificity of the amplification reaction can be improved. This will minimize amplification of nonspecific regions of the template DNA. Purification of the DNA fragments can also allow multiplex PCR (Polymerase Chain Reaction) or amplification of multiple loci of interest with improved specificity.

In one embodiment, the nucleic acid sample is obtained with a desired purpose in mind such as to determine the sequence at a predetermined locus or loci of interest using the method of the invention. For example, the nucleic acid is obtained for the purpose of identifying one or more conditions or diseases to which the subject can be predisposed or is in need of treatment for, or the presence of certain single nucleotide polymorphisms. In an alternative embodiment, the sample is obtained to screen for the presence or absence of one or more DNA sequence markers, the presence of which would identify that DNA as being from a specific bacterial or fungal microorganism, or individual.

The loci of interest that are to be sequenced can be selected based upon sequence alone. In humans, over 1.42 million single nucleotide polymorphisms (SNPs) have been described (Nature 409:928–933 (2001); The SNP Consortium LTD). On the average, there is one SNP every 1.9 kb of human genome. However, the distance between loci of interest need not be considered when selecting the loci of interest to be sequenced according to the invention. If more than one locus of interest on genomic DNA is being analyzed, the selected loci of interest can be on the same chromosome or on different chromosomes.

In a preferred embodiment, the length of sequence that is amplified is preferably different for each locus of interest so that the loci of interest can be separated by size.

In fact, it is an advantage of the invention that primers that copy an entire gene sequence need not be utilized. Rather, the copied locus of interest is preferably only a small part of the total gene. There is no advantage to sequencing the entire gene as this can increase cost and delay results. Sequencing only the desired bases or loci of interest within the gene maximizes the overall efficiency of the method because it allows for the maximum number of loci of interest to be determined in the fastest amount of time and with minimal cost.

Because a large number of sequences can be analyzed together, the method of the invention is especially amenable to the large-scale screening of a number of individual samples.

Any number of loci of interest can be analyzed and processed, especially concurrently, using the method of the invention. The sample(s) can be analyzed to determine the sequence at one locus of interest or at multiple loci of interest concurrently. For example, the 10 or 20 most frequently occurring mutation sites in a disease associated gene can be sequenced to detect the majority of the disease carriers.

Alternatively, 2, 3, 4, 5, 6, 7, 8, 9, 10–20, 20–25, 25–30, 30–35, 35–40, 40–45, 45–50, 50–100, 100–250, 250–500, 500–1,000, 1,000–2,000, 2,000–3,000, 3,000–5,000, 5,000–10,000, 10,000–50,000 or more than 50,000 loci of interest can be analyzed at the same time when a global genetic screening is desired. Such a global genetic screening might be desired when using the method of the invention to provide a genetic fingerprint to identify a certain microorganism or individual or for SNP genotyping.

The multiple loci of interest can be targets from different organisms. For example, a plant, animal or human subject in need of treatment can have symptoms of infection by one or more pathogens. A nucleic acid sample taken from such a plant, animal or human subject can be analyzed for the presence of multiple suspected or possible pathogens at the same time by determining the sequence of loci of interest which, if present, would be diagnostic for that pathogen. Not only would the finding of such a diagnostic sequence in the subject rapidly pinpoint the cause of the condition, but also it would rule out other pathogens that were not detected. Such screening can be used to assess the degree to which a pathogen has spread throughout an organism or environment. In a similar manner, nucleic acid from an individual suspected of having a disease that is the result of a genetic abnormality can be analyzed for some or all of the known mutations that result in the disease, or one or more of the more common mutations.

The method of the invention can be used to monitor the integrity of the genetic nature of an organism. For example, samples of yeast can be taken at various times and from various batches in the brewing process, and their presence or identity compared to that of a desired strain by the rapid analysis of their genomic sequences as provided herein.

The locus of interest that is to be copied can be within a coding sequence or outside of a coding sequence. Preferably, one or more loci of interest that are to be copied are within a gene. In a preferred embodiment, the template DNA that is copied is a locus or loci of interest that is within a genomic coding sequence, either intron or exon. In a highly preferred embodiment, exon DNA sequences are copied. The loci of interest can be sites where mutations are known to cause disease or predispose to a disease state. The loci of interest can be sites of single nucleotide polymorphisms. Alternatively, the loci of interest that are to be copied can be outside of the coding sequence, for example, in a transcriptional regulatory region, and especially a promoter, enhancer, or repressor sequence.

Primer Design

Published sequences, including consensus sequences, can be used to design or select primers for use in amplification of template DNA. The selection of sequences to be used for the construction of primers that flank a locus of interest can be made by examination of the sequence of the loci of interest, or immediately thereto. The recently published sequence of the human genome provides a source of useful consensus sequence information from which to design primers to flank a desired human gene locus of interest.

By "flanking" a locus of interest is meant that the sequences of the primers are such that at least a portion of the 3' region of one primer is complementary to the antisense strand of the template DNA and upstream of the locus of interest (forward primer), and at least a portion of the 3' region of the other primer is complementary to the sense strand of the template DNA and downstream of the locus of interest (reverse primer). A "primer pair" is intended to specify a pair of forward and reverse primers. Both primers of a primer pair anneal in a manner that allows extension of the primers, such that the extension results in amplifying the template DNA in the region of the locus of interest.

Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources such as Operon Technologies, Amersham Pharmacia Biotech, Sigma, and Life Technologies. The primers of a primer pair can have the same length. Alternatively, one of the primers of the primer pair can be longer than the other primer of the primer pair. The primers can have an identical melting temperature. The lengths of the primers can be extended or shortened at the 5' end or the 3' end to produce primers with desired melting temperatures. In a preferred embodiment, the 3' annealing lengths of the primers, within a primer pair, differ. Also, the annealing position of each primer pair can be designed such that the sequence and length of the primer pairs yield the desired melting temperature. The simplest equation for determining the melting temperature of primers smaller than 25 base pairs is the Wallace Rule (Td=2(A+T)+4(G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Net Primer (free web based program at available at world wide web: premierbiosoft.com/netprimer/netprlaunch/netprlaunch.html. (internet address as of Feb. 13, 2002).

In another embodiment, the annealing temperature of the primers can be recalculated and increased after any cycle of amplification, including but not limited to cycle 1, 2, 3, 4, 5, cycles 6–10, cycles 10–15, cycles 15–20, cycles 20–25, cycles 25–30, cycles 30–35, or cycles 35–40. After the initial cycles of amplification, the 5' half of the primers is incorporated into the products from each loci of interest, thus the TM can be recalculated based on both the sequences of the 5' half and the 3' half of each primer.

For example, in FIG. 1B, the first cycle of amplification is performed at about the melting temperature of the 3' region of the second primer (region "c") that anneals to the template DNA, which is 13 bases. After the first cycle, the annealing temperature can be raised to TM2, which is about the melting temperature of the 3' region of the first primer (region "b'") that anneals to the template DNA. The second primer cannot bind to the original template DNA because it only anneals to 13 bases in the original DNA template, and TM2 is about the melting temperature of approximately 20 bases, which is the 3' annealing region of the first primer (FIG. 1C). However, the first primer can bind to the DNA that was copied in the first cycle of the reaction. In the third cycle, the annealing temperature is raised to TM3, which is about the melting temperature of the entire sequence of the second primer ("c" and "d"). The template DNA produced from the second cycle of PCR contains both regions c' and d', and therefore, the second primer can anneal and extend at TM3 (FIG. 1D). The remaining cycles are performed at TM3. The entire sequence of the first primer (a+b') can anneal to the template from the third cycle of PCR, and extend (FIG. 1E). Increasing the annealing temperature will decrease non-specific binding and increase the specificity of the reaction, which is especially useful if amplifying a locus of interest from human genomic DNA, which contains 3×10$^9$ base pairs.

As used herein, the term "about" with regard to annealing temperatures is used to encompass temperatures within 10 degrees Celsius of the stated temperatures.

In one embodiment, one primer pair is used for each locus of interest. However, multiple primer pairs can be used for each locus of interest.

In one embodiment, primers are designed such that one or both primers of the primer pair contain sequence in the 5' region for one or more restriction endonucleases (restriction enzyme).

As used herein, with regard to the position at which restriction enzymes digest DNA, the "sense" strand is the strand reading 5' to 3' in the direction in which the restriction enzyme cuts. For example, BsmF I recognizes the following sequence:

```
5' GGGAC(N)10↓ 3'           (SEQ ID NO:1)
3' CCCTG(N)14↑ 5' or
5'↓ (N)14GTCCC 3'           (SEQ ID NO:2)
3'↑ (N)10CAGGG 5'
```

Thus, the sense strand is the strand containing the "GGGAC" sequence as it reads 5' to 3' in the direction that the restriction enzyme cuts.

As used herein, with regard to the position at which restriction enzymes digest DNA, the "antisense" strand is the strand reading 3' to 5' in the direction in which the restriction enzyme cuts. Thus, the antisense strand is the strand that contains the "ccctg" sequence as it reads 3' to 5'.

In the invention, one of the primers in a primer pair can be designed such that it contains a restriction enzyme recognition site for a restriction enzyme such that digestion with the restriction enzyme produces a recessed 3' end and a 5' overhang that contains the locus of interest (herein referred to as a "second primer"). For example, the second primer of a primer pair can contain a recognition site for a restriction enzyme that does not cut DNA at the recognition site but cuts "n" nucleotides away from the recognition site. "N" is a distance from the recognition site to the site of the cut by the restriction enzyme. If the recognition sequence is for the restriction enzyme BceA I, the enzyme will cut ten (10) nucleotides from the recognition site on the sense strand, and twelve (12) nucleotides away from the recognition site on the antisense strand.

The 3' region and preferably the 3' half of the primers is designed to anneal to a sequence that flanks the loci of interest (FIG. 1A). The second primer may anneal any distance from the locus of interest provided that digestion with the restriction enzyme that recognizes the restriction enzyme recognition site on this primer generates a 5' overhang that contains the locus of interest. The 5' overhang can be of any size, including but not limited to 1, 2, 3, 4, 5, 6, 7, 8, and more than 8 bases.

In a preferred embodiment, the 3' end of the second primer can anneal 1, 2, 3, 4, 5, 6, 7, 8, 9, 10, 11, 12, 13, 14, or more than 14 bases from the locus of interest or at the locus of interest.

In a preferred embodiment, the second primer is designed to anneal closer to the locus of interest than the other primer of a primer pair (the other primer is herein referred to as a "first primer"). The second primer can be a forward or reverse primer and the first primer can be a reverse or forward primer, respectively. Whether the first or second primer should be the forward or reverse primer can be determined by which design will provide better sequencing results.

For example, the primer that anneals closer to the locus of interest can contain a recognition site for the restriction enzyme BsmF I, which cuts ten (10) nucleotides from the recognition site on the sense strand, and fourteen (14) nucleotides from the recognition site on the antisense strand. In this case, the primer can be designed so that the restriction enzyme recognition site is 13 bases, 12 bases, 10 bases or 11 bases from the locus of interest. If the recognition site is 13 bases from the locus of interest, digestion with BsmF I will generate a 5' overhang (RXXX), wherein the locus of interest (R) is the first nucleotide in the overhang (reading 3' to 5'), and X is any nucleotide. If the recognition site is 12 bases from the locus of interest, digestion with BsmF I will generate a 5' overhang (XRXX), wherein the locus of interest (R) is the second nucleotide in the overhang (reading 3' to 5'). If the recognition site is 11 bases from the locus of interest, digestion with BsmF I will generate a 5' overhang (XXRX), wherein the locus of interest (R) is the third nucleotide in the overhang (reading 3' to 5'). The distance between the restriction enzyme recognition site and the locus of interest should be designed so that digestion with the restriction enzyme generates a 5' overhang, which contains the locus of interest. The effective distance between the recognition site and the locus of interest will vary depending on the choice of restriction enzyme.

In another embodiment, the second primer, which can anneal closer to the locus of interest relative to the first primer, can be designed so that the restriction enzyme that generates the 5' overhang, which contains the locus of interest, will see the same sequence at the cut site, independent of the nucleotide at the locus of interest. For example, if the primer that anneals closer to the locus of interest is designed so that the recognition site for the restriction enzyme BsmF I (5' GGGAC 3') is thirteen bases from the locus of interest, the restriction enzyme will cut the antisense strand one base upstream of the locus of interest. The nucleotide at the locus of interest is adjacent to the cut site, and may vary from DNA molecule to DNA molecule. If it is desired that the nucleotides adjacent to the cut site be identical, the primer can be designed so that the restriction enzyme recognition site for BsmF I is twelve bases away from the locus of interest. Digestion with BsmF I will generate a 5' overhang, wherein the locus of interest is in the second position of the overhang (reading 3' to 5') and is no longer adjacent to the cut site. Designing the primer so that the restriction enzyme recognition site is twelve (12) bases from the locus of interest allows the nucleotides adjacent to the cut site to be the same, independent of the nucleotide at the locus of interest. Also, primers that have been designed so that the restriction enzyme recognition site is eleven (11) or ten (10) bases from the locus of interest will allow the nucleotides adjacent to the cut site to be the same, independent of the nucleotide at the locus of interest.

The 3' end of the first primer (either the forward or the reverse) can be designed to anneal at a chosen distance from the locus of interest. Preferably, for example, this distance is between 10–25, 25–50, 50–75, 75–100, 100–150, 150–200, 200–250, 250–300, 300–350, 350–400, 400–450, 450–500, 500–550, 550–600, 600–650, 650–700, 700–750, 750–800, 800–850, 850–900, 900–950, 950–1000 and greater than 1000 bases away from the locus of interest. The annealing sites of the first primers are chosen such that each successive upstream primer is further and further away from its respective downstream primer.

For example, if at locus of interest 1 the 3' ends of the first and second primers are Z bases apart, then at locus of interest 2, the 3' ends of the upstream and downstream primers are Z+K bases apart, where K=1, 2, 3, 4, 5–10, 10–20, 20–30, 30–40, 40–50, 50–60, 60–70, 70–80, 80–90, 90–100, 100–200, 200–300, 300–400, 400–500, 500–600, 600–700, 700–800, 800–900, 900–1000, or greater than 1000 bases (FIG. 2). The purpose of making the upstream primers further and further apart from their respective downstream primers is so that the PCR products of all the loci of interest differ in size and can be separated, e.g., on a sequencing gel. This allows for multiplexing by pooling the PCR products in later steps.

In one embodiment, the 5' region of the first primer can have a recognition site for any type of restriction enzyme. In a preferred embodiment, the first primer has at least one restriction enzyme recognition site that is different from the restriction enzyme recognition site in the second primer. In another preferred embodiment, the first primer anneals further away from the locus of interest than the second primer.

In a preferred embodiment, the second primer contains a restriction enzyme recognition sequence for a Type IIS restriction enzyme including but not limited to BceA I and BsmF I, which produce a two base 5' overhang and a four base 5' overhang, respectively. Restriction enzymes that are Type IIS are preferred because they recognize asymmetric base sequences (not palindromic like the orthodox Type II enzymes). Type IIS restriction enzymes cleave DNA at a specified position that is outside of the recognition site, typically up to 20 base pairs outside of the recognition site. These properties make Type IIS restriction enzymes, and the recognition sites thereof, especially useful in the method of the invention. Preferably, the Type IIS restriction enzymes used in this method leave a 5' overhang and a recessed 3' end.

A wide variety of Type IIS restriction enzymes are known and such enzymes have been isolated from bacteria, phage, archeabacteria and viruses of eukaryotic algae and are commercially available (Promega, Madison Wis.; New England Biolabs, Beverly, Mass.; Szybalski W. et al., *Gene* 100:13–16, (1991)). Examples of Type IIS restriction enzymes that would be useful in the method of the invention include, but are not limited to enzymes such as those listed in Table I.

TABLE I

Type IIS restriction enzymes that generate a 5' overhang and a recessed 3' end.

| Enzyme-Source | Recognition/Cleavage Site | Supplier |
|---|---|---|
| Alw I-*Acinetobacter lwoffii* | GGATC(4/5) | NE Biolabs |
| Alw26 I-*Acinetobacter lwoffi* | GTCTC(1/5) | Promega |
| Bbs I-*Bacillus laterosporus* | GAAGAC(2/6) | NE Biolabs |
| Bbv I-*Bacillus brevis* | GCAGC(8/12) | NE Biolabs |
| BceA I-*Bacillus cereus* 1315 | ACGGC(12/14) | NE Biolabs |
| Bmr I-*Bacillus megaterium* | ACTGGG(5/4) | NE Biolabs |
| Bsa I-*Bacillus stearothermophilus* 6-55 | GGTCTC(1/5) | NE Biolabs |
| Bst71 I-*Bacillus stearothermophilus* 71 | GCAGC(8/12) | Promega |
| BsmA I-*Bacillus stearothermophilus* A664 | GTCTC(1/5) | NE Biolabs |
| BsmB I-*Bacillus stearotherinophilus* B61 | CGTCTC(1/5) | NE Biolabs |
| BsmF I-*Bacillus stearothermophilus* F | GGGAC(10/14) | NE Biolabs |
| BspM I-*Bacillus species* M | ACCTGC(4/8) | NE Biolabs |
| Ear I-*Enterobacter aerogenes* | CTCTTC(1/4) | NE Biolabs |
| Fau I-*Flavobacterium aquatile* | CCCGC(416) | NE Biolabs |
| Fok I-*Flavobacterium okeonokoites* | GGATG(9/13) | NE Biolabs |
| Hga I-*Haemophilus gallinarum* | GACGC(5/10) | NE Biolabs |
| Ple I-*Pseudomonas lemoignei* | GAGTC(4/5) | NE Biolabs |
| Sap I-*Saccharopolyspora species* | GCTCTTC(1/4) | NE Biolabs |
| SfaN I-*Streptococcus faecalis* ND547 | GCATC(5/9) | NE Biolabs |
| Sth 132 I-*Streptococcus thermophilus* ST132 | CCCG(4/8) | No commercial supplier (Gene 195:201-206 (1997)) |

In one embodiment, a primer pair has sequence at the 5' region of each of the primers that provides a restriction enzyme recognition site that is unique for one restriction enzyme.

In another embodiment, a primer pair has sequence at the 5' region of each of the primers that provide a restriction site that is recognized by more than one restriction enzyme, and especially for more than one Type IIS restriction enzyme. For example, certain consensus sequences can be recognized by more than one enzyme. For example, BsgI, Eco57I and BpmI all recognize the consensus 5' (G/C)TgnAG 3' and cleave 16 bp away on the antisense strand and 14 bp away on the sense strand. A primer that provides such a consensus sequence would result in a product that has a site that can be recognized by any of the restriction enzymes BsgI, Eco57I and BpmI.

Other restriction enzymes that cut DNA at a distance from the recognition site, and produce a recessed 3' end and a 5' overhang include Type III restriction enzymes. For example, the restriction enzyme EcoP15I recognizes the sequence 5' CAGCAG 3' and cleaves 25 bases downstream on the sense strand and 27 bases on the antisense strand. It will be further appreciated by a person of ordinary skill in the art that new restriction enzymes are continually being discovered and may readily be adopted for use in the subject invention.

In another embodiment, the second primer can contain a portion of the recognition sequence for a restriction enzyme, wherein the full recognition site for the restriction enzyme is generated upon amplification of the template DNA such that digestion with the restriction enzyme generates a 5' overhang containing the locus of interest. For example, the recognition site for BsmF I is 5' GGGACN$_{10}$↓03'. The 3' region, which anneals to the template DNA, of the second primer can end with the nucleotides "GGG," which do not have to be complementary with the template DNA. If the 3' annealing region is about 10–20 bases, even if the last three bases do not anneal, the primer will extend and, generate a BsmF I site.

Second primer:
5' GGAAATTCCATGATGCGTGGG→           (SEQ ID NO:3)

Template DNA:
3' CCTTTAAGGTACTACGCAN$_1$·N$_2$·N$_3$·TG 5'

5' GGAAATTCCATGATGCGTN$_1$N$_2$N$_3$AC 3'     (SEQ ID NO:4)

The second primer can be designed to anneal to the template DNA, wherein the next two bases of the template DNA are thymidine and guanine, such that an adenosine and cytosine are incorporated into the primer forming a recognition site for BsmF I, 5' GGGACN$_{10}$↓03'. The second primer can be designed to anneal in such a manner that digestion with BsmF I generates a 5' overhang containing the locus of interest.

In another embodiment, the second primer can contain an entire or full recognition site for a restriction enzyme or a portion of a recognition site, which generates a full recognition site upon amplification of the template DNA such that digestion with a restriction enzyme that cuts at the recognition site generates a 5' overhang that contains the locus of interest. For example, the restriction enzyme BsaJ I binds the following recognition site: 5' C↓CN$_1$N$_2$GG 3'. The second primer can be designed such that the 3' region of the primer ends with "CC." The SNP of interest is represented by "N$_1$'", and the template sequence downstream of the SNP is "N$_2$.CC."

```
Second primer
5' GGAAATTCCATGATGCGTACC→ (SEQ ID
NO:5)

Template DNA
3' CCTTTAAGGTACTACGCATGGN₁·N₂·CC 5'

5' GGAAATTCCATGATGCGTACCN₁N₂GG 3' (SEQ
ID NO:6)
```

After digestion with BsaJ I, a 5' overhang of the following sequence would be generated:

```
      5'C          3'

3'GGN₁·N₂·C 5'
```

If the nucleotide guanine is not reported at the locus of interest, the 3' recessed end can be filled in with unlabeled cytosine, which is complementary to the first nucleotide in the overhang. After removing the excess cytosine, labeled ddNTPs can be used to fill in the next nucleotide, N$_1$', which represents the locus of interest. Alternatively if guanine is reported to be a potential nucleotide at the locus of interest, labeled nucleotides can be used to detect a nucleotide 3' of the locus of interest. Unlabeled dCTP can be used to "fill in" followed by a fill in with a labeled nucleotide other that cytosine. Cytosine will be incorporated until it reaches a base that is not complementary. If the locus of interest contained a guanine, it would be filled in with the dCTP, which would allow incorporation of the labeled nucleotide. However, if the locus of interest did not contain a guanine, the labeled nucleotide would not be incorporated. Other restriction enzymes can be used including but not limited to BssK I (5' ↓CCNGG 3'), Dde I (5' C↓TNAG 3'), EcoN I (5' CCTNN↓NNNAGG 3') (SEQ ID NO:7), Fnu4H I (5' GC↓NGC 3'), Hinf I (5' G↓ANTC 3'), Pf1F I (5' GACN↓NNGTC 3'), Sau96 I (5' G↓GNCC 3'), ScrF I (5' CC↓NGG 3'), and Tth111 I (5' GACN↓NNGTC 3').

It is not necessary that the 3' region, which anneals to the template DNA, of the second primer be 100% complementary to the template DNA. For example, the last 1, 2, or 3 nucleotides of the 3' end of the second primer can be mismatches with the template DNA. The region of the primer that anneals to the template DNA will target the primer, and allow the primer to extend. Even if, for example, the last two nucleotides are not complementary to the template DNA, the primer will extend and generate a restriction enzyme recognition site.

```
Second primer:
5' GGAAATTCCATGATGCGTACC→            (SEQ ID NO:5)

Template DNA:
3' CCTTTAAGGTACTACGCATN_a·N_b·N₁·N₂·CC 5'

5' GGAAATTCCATGATGCGTAN_aN_bN₁N₂GG 3'  (SEQ ID NO:8)
```

After digestion with BsaJ I, a 5' overhang of the following sequence would be generated:

```
      5' C          3'

3' GGN₁·N₂·C 5'
```

If the nucleotide cytosine is not reported at the locus of interest, the 5' overhang can be filled in with unlabeled cytosine. The excess cytosine can be rinsed away, and filled in with labeled ddNTPs. The first nucleotide incorporated (N$_1$) corresponds to the locus of interest.

Alternatively, it is possible to create the full restriction enzyme recognition sequence using the first and second primers. The recognition site for any restriction enzyme can be generated, as long as the recognition site contains at least one variable nucleotide. Restriction enzymes that recognize sites that contain at least one variable nucleotide include but are not limited to BssK I (5'↓CCNGG 3'), Dde I (5'C↓TNAG 3'), Econ I (5'CCTNN↓NNNAGG 3') (SEQ ID NO:7), Fnu4H I (5'GC↓NGC 3'), Hinf I (5'G↓ANTC 3') Pf1F I (5' GACN↓NNGTC 3'), Sau96 I (5'G↓GNCC 3'), ScrF I (5' CC↓NGG 3'), and Tth111 I (5' GACN↓NNGTC 3'). In this embodiment, the first or second primer may anneal closer to the locus of interest or the first or second primer may anneal at an equal distance from the locus of interest. The first and second primers can be designed to contain mismatches to the template DNA at the 3' region; these mismatches create the restriction enzyme recognition site. The number of mismatches that can be tolerated at the 3' end depends on the length of the primer, and includes but is not limited to 1, 2, or more than 2 mismatches. For example, if the locus of interest is represented by N$_1$', a first primer can be designed to be complementary to the template DNA, depicted below as region "a." The 3' region of the first primer ends with "CC," which is not complementary to the template DNA. The second primer is designed to be complementary to the template DNA, which is depicted below as region "b'". The 3' region of the second primer ends with "CC," which is not complementary to the template DNA.

```
First primer   5'  _a_CC→

Template DNA   3'  _a'_   AAN₁·N₂·TT_b'_   5'

5'  _a_  TTN₁N₂AA_b_  3'

←CC_b'_  5' Second
                                         Primer
```

After one round of amplification the following products would be generated:

```
        5'_a_CCN₁N₂AA_b_3'
        and

5'_b'_CCN₂·N₁·AA_a'_3'.
```

In cycle two, the primers can anneal to the templates that were generated from the first cycle of PCR:

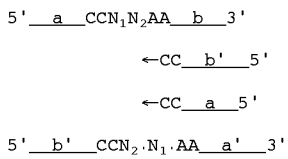

After cycle two of PCR, the following products would be generated:

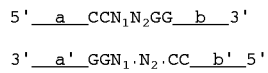

The restriction enzyme recognition site for BsaJ I is generated, and after digestion with BsaJ I, a 5' overhang containing the locus of interest is generated. The locus of interest can be detected as described in detail below. Alternatively, the 3' region of the first and second primers can contain 1, 2, 3, or more than 3 mismatches followed by a nucleotide that is complementary to the template DNA. For example, the first and second primers can be used to create a recognition site for the restriction enzyme EcoN I, which binds the following DNA sequence: 5' CCTNN↓NNNAGG 3'. The last nucleotides of each primer would be "CCTN$_1$ or CCTN$_1$N$_2$." The nucleotides "CCT" may or may not be complementary to the template DNA; however, N$_1$ and N$_2$ are nucleotides complementary to the template DNA. This allows the primers to anneal to the template DNA after the potential mismatches, which are used to create the restriction enzyme recognition site.

In another embodiment, a primer pair has sequence at the 5' region of each of the primers that provides two or more restriction sites that are recognized by two or more restriction enzymes.

In a most preferred embodiment, a primer pair has different restriction enzyme recognition sites at the 5' regions, especially 5' ends, such that a different restriction enzyme is required to cleave away any undesired sequences. For example, the first primer for locus of interest "A" can contain sequence recognized by a restriction enzyme, "X," which can be any type of restriction enzyme, and the second primer for locus of interest "A," which anneals closer to the locus of interest, can contain sequence for a restriction enzyme, "Y," which is a Type IIS restriction enzyme that cuts "n" nucleotides away and leaves a 5' overhang and a recessed 3' end. The 5' overhang contains the locus of interest. After binding the amplified DNA to streptavidin coated wells, one can digest with enzyme "Y," rinse, then fill in with labeled nucleotides and rinse, and then digest with restriction enzyme "X," which will release the DNA fragment containing the locus of interest from the solid matrix. The locus of interest can be analyzed by detecting the labeled nucleotide that was "filled in" at the locus of interest, e.g. SNP site.

In another embodiment, the second primers for the different loci of interest that are being amplified according to the invention contain recognition sequence in the 5' regions for the same restriction enzyme and likewise all the first primers also contain the same restriction enzyme recognition site, which is a different enzyme from the enzyme that recognizes the second primers. The primer (either the forward or reverse primer) that anneals closer to the locus of interest contains a recognition site for, e.g., a Type IIs restriction enzyme.

In another embodiment, the second primers for the multiple loci of interest that are being amplified according to the invention contain restriction enzyme recognition sequences in the 5' regions for different restriction enzymes.

In another embodiment, the first primers for the multiple loci of interest that are being amplified according to the invention contain restriction enzyme recognition sequences in the 5' regions for different restriction enzymes.

Multiple restriction enzyme sequences provide an opportunity to influence the order in which pooled loci of interest are released from the solid support. For example, if 50 loci of interest are amplified, the first primers can have a tag at the extreme 5' end to aid in purification and a restriction enzyme recognition site, and the second primers can contain a recognition site for a type IIS restriction enzyme. For example, several of the first primers can have a restriction enzyme recognition site for EcoR I, other first primers can have a recognition site for Pst I, and still other first primers can have a recognition site for BamH I. After amplification, the loci of interest can be bound to a solid support with the aid of the tag on the first primers. By performing the restriction digests one restriction enzyme at a time, one can serially release the amplified loci of interest. If the first digest is performed with EcoRI, the loci of interest amplified with the first primers containing the recognition site for EcoR I will be released, and collected while the other loci of interest remain bound to the solid support. The amplified loci of interest can be selectively released from the solid support by digesting with one restriction enzyme at a time. The use of different restriction enzyme recognition sites in the first primers allows a larger number of loci of interest to be amplified in a single reaction tube.

In a preferred embodiment, any region 5' of the restriction enzyme digestion site of each primer can be modified with a functional group that provides for fragment manipulation, processing, identification, and/or purification. Examples of such functional groups, or tags, include but are not limited to biotin, derivatives of biotin, carbohydrates, haptens, dyes, radioactive molecules, antibodies, and fragments of antibodies, peptides, and immunogenic molecules.

In another embodiment, the template DNA can be replicated once, without being amplified beyond a single round of replication. This is useful when there is a large amount of the DNA available for analysis such that a large number of copies of the loci of interest are already present in the sample, and further copies are not needed. In this embodiment, the primers are preferably designed to contain a "hairpin" structure in the 5' region, such that the sequence doubles back and anneals to a sequence internal to itself in a complementary manner. When the template DNA is replicated only once, the DNA sequence comprising the recognition site would be single-stranded if not for the "hairpin" structure. However, in the presence of the hairpin structure, that region is effectively double stranded, thus providing a double stranded substrate for activity by restriction enzymes.

To the extent that the reaction conditions are compatible, all the primer pairs to analyze a locus or loci of interest of DNA can be mixed together for use in the method of the invention. In a preferred embodiment, all primer pairs are mixed with the template DNA in a single reaction vessel. Such a reaction vessel can be, for example, a reaction tube, or a well of a microtiter plate.

Alternatively, to avoid competition for nucleotides and to minimize primer dimers and difficulties with annealing temperatures for primers, each locus of interest or small groups of loci of interest can be amplified in separate reaction tubes or wells, and the products later pooled if desired. For example, the separate reactions can be pooled into a single reaction vessel before digestion with the restriction enzyme that generates a 5' overhang, which contains the locus of interest or SNP site, and a 3' recessed end. Preferably, the primers of each primer pair are provided in equimolar amounts. Also, especially preferably, each of the different primer pairs is provided in equimolar amounts relative to the other pairs that are being used.

In another embodiment, combinations of primer pairs that allow efficient amplification of their respective loci of interest can be used (see e.g. FIG. 2). Such combinations can be determined prior to use in the method of the invention. Multi-well plates and PCR machines can be used to select primer pairs that work efficiently with one another. For example, gradient PCR machines, such as the Eppendorf Mastercycler® gradient PCR machine, can be used to select the optimal annealing temperature for each primer pair. Primer pairs that have similar properties can be used together in a single reaction tube.

In another embodiment, a multi-sample container including but not limited to a 96-well or more plate can be used to amplify a single locus of interest with the same primer pairs from multiple template DNA samples with optimal PCR conditions for that locus of interest. Alternatively, a separate multi-sample container can be used for amplification of each locus of interest and the products for each template DNA sample later pooled. For example, gene A from 96 different DNA samples can be amplified in microtiter plate 1, gene B from 96 different DNA samples can be amplified in microtiter plate 2, etc., and then the amplification products can be pooled.

The result of amplifying multiple loci of interest is a preparation that contains representative PCR products having the sequence of each locus of interest. For example, if DNA from only one individual is used as the template DNA and if hundreds of disease-related loci of interest were amplified from the template DNA, the amplified DNA would be a mixture of small, PCR products from each of the loci of interest. Such a preparation could be further analyzed at that time to determine the sequence at each locus of interest or at only some of loci of interest. Additionally, the preparation could be stored in a manner that preserves the DNA and can be analyzed at a later time. Information contained in the amplified DNA can be revealed by any suitable method including but not limited to fluorescence detection, sequencing, gel electrophoresis, and mass spectrometry (see "Detection of Incorporated Nucleotide" section below).

Amplification of Loci of Interest

The template DNA can be amplified using any suitable method known in the art including but not limited to PCR (polymerase chain reaction), 3SR (self-sustained sequence reaction), LCR (ligase chain reaction), RACE-PCR (rapid amplification of cDNA ends), PLCR (a combination of polymerase chain reaction and ligase chain reaction), Q-beta phage amplification (Shah et al., J. Medical Micro. 33: 1435–41 (1995)), SDA (strand displacement amplification), SOE-PCR (splice overlap extension PCR), and the like. These methods can be used to design variations of the releasable primer mediated cyclic amplification reaction explicitly described in this application. In the most preferred embodiment, the template DNA is amplified using PCR (PCR: A Practical Approach, M. J. McPherson, et al., IRL Press (1991); PCR Protocols: A Guide to Methods and Applications, Innis, et al., Academic Press (1990); and PCR Technology: Principals and Applications of DNA Amplification, H. A. Erlich, Stockton Press (1989)). PCR is also described in numerous U.S. patents, including U.S. Pat. Nos. 4,683,195; 4,683,202; 4,800,159; 4,965,188; 4,889,818; 5,075,216; 5,079,352; 5,104,792, 5,023,171; 5,091,310; and 5,066,584.

The components of a typical PCR reaction include but are not limited to a template DNA, primers, a reaction buffer (dependent on choice of polymerase), dNTPs (dATP, dTTP, dGTP, and dCTP) and a DNA polymerase. Suitable PCR primers can be designed and prepared as discussed above (see "Primer Design" section above). Briefly, the reaction is heated to 95° C. for 2 min. to separate the strands of the template DNA, the reaction is cooled to an appropriate temperature (determined by calculating the annealing temperature of designed primers) to allow primers to anneal to the template DNA, and heated to 72° C. for two minutes to allow extension.

In a preferred embodiment, the annealing temperature is increased in each of the first three cycles of amplification to reduce non-specific amplification. See also Example 1, below. The TM1 of the first cycle of PCR is about the melting temperature of the 3' region of the second primer that anneals to the template DNA. The annealing temperature can be raised in cycles 2–10, preferably in cycle 2, to TM2, which is about the melting temperature of the 3' region, which anneals to the template DNA, of the first primer. If the annealing temperature is raised in cycle 2, the annealing temperature remains about the same until the next increase in annealing temperature. Finally, in any cycle subsequent to the cycle in which the annealing temperature was increased to TM2, preferably cycle 3, the annealing temperature is raised to TM3, which is about the melting temperature of the entire second primer. After the third cycle, the annealing temperature for the remaining cycles may be at about TM3 or may be further increased. In this example, the annealing temperature is increased in cycles 2 and 3. However, the annealing temperature can be increased from a low annealing temperature in cycle 1 to a high annealing temperature in cycle 2 without any further increases in temperature or the annealing temperature can progressively change from a low annealing temperature to a high annealing temperature in any number of incremental steps. For example, the annealing temperature can be changed in cycles 2, 3, 4, 5, 6, etc.

After annealing, the temperature in each cycle is increased to an "extension" temperature to allow the primers to "extend" and then following extension the temperature in each cycle is increased to the denaturization temperature. For PCR products less than 500 base pairs in size, one can eliminate the extension step in each cycle and just have denaturization and annealing steps. A typical PCR reaction consists of 25–45 cycles of denaturation, annealing and extension as described above. However, as previously noted, even only one cycle of amplification (one copy) can be sufficient for practicing the invention.

Any DNA polymerase that catalyzes primer extension can be used including but not limited to E. coli DNA polymerase, Klenow fragment of E. coli DNA polymerase I, T7 DNA polymerase, T4 DNA polymerase, Taq polymerase, Pfu DNA polymerase, Vent DNA polymerase, or sequenase. Preferably, a thermostable DNA polymerase is used. A "hot start" PCR can also be performed wherein the reaction is heated to 95° C. for two minutes prior to addition of the polymerase or the polymerase can be kept inactive until the first heating step in cycle 1. "Hot start" PCR can be used to minimize nonspecific amplification. Any number of PCR cycles can be used to amplify the DNA, including but not limited to 2, 5, 10, 15, 20, 25, 30, 35, 40, or 45 cycles. In a most preferred embodiment, the number of PCR cycles performed is such that equimolar amounts of each loci of interest are produced.

Purification of Amplified DNA

Purification of the amplified DNA is not necessary for practicing the invention. However, in one embodiment, if purification is preferred, the 5' end of the primer (first or second primer) can be modified with a tag that facilitates purification of the PCR products. In a preferred embodiment, the first primer is modified with a tag that facilitates purification of the PCR products. The modification is preferably the same for all primers, although different modifications can be used if it is desired to separate the PCR products into different groups.

The tag can be a radioisotope, fluorescent reporter molecule, chemiluminescent reporter molecule, antibody, antibody fragment, hapten, biotin, derivative of biotin, photobiotin, iminobiotin, digoxigenin, avidin, enzyme, acridinium, sugar, enzyme, apoenzyme, homopolymeric oligonucleotide, hormone, ferromagnetic moiety, paramagnetic moiety, diamagnetic moiety, phosphorescent moiety, luminescent moiety, electrochemiluminescent moiety, chromatic moiety, moiety having a detectable electron spin resonance, electrical capacitance, dielectric constant or electrical conductivity, or combinations thereof.

In a preferred embodiment, the 5' ends of the primers can be biotinylated (Kandpal et al., Nucleic Acids Res. 18:1789–1795 (1990); Kaneoka et al., Biotechniques 10:30–34 (1991); Green et al., Nucleic Acids Res. 18:6163–6164 (1990)). The biotin provides an affinity tag that can be used to purify the copied DNA from the genomic DNA or any other DNA molecules that are not of interest. Biotinylated molecules can be purified using a streptavidin coated matrix as shown in FIG. 1F, including but not limited to Streptawell, transparent, High-Bind plates from Roche Molecular Biochemicals (catalog number 1 645 692, as listed in Roche Molecular Biochemicals, 2001 Biochemicals Catalog).

The PCR product of each locus of interest is placed into separate wells of a Streptavidin coated plate. Alternatively, the PCR products of the loci of interest can be pooled and placed into a streptavidin coated matrix, including but not limited to the Streptawell, transparent, High-Bind plates from Roche Molecular Biochemicals (catalog number 1 645 692, as listed in Roche Molecular Biochemicals, 2001 Biochemicals Catalog).

The amplified DNA can also be separated from the template DNA using non-affinity methods known in the art, for example, by polyacrylamide gel electrophoresis using standard protocols.

Digestion of Amplified DNA

The amplified DNA can be digested with a restriction enzyme that recognizes a sequence that had been provided on the first or second primer using standard protocols known within the art (FIGS. 6A–6D). The enzyme used depends on the restriction recognition site generated with the first or second primer. See "Primer Design" section, above, for details on restriction recognition sites generated on primers.

Type IIS restriction enzymes are extremely useful in that they cut approximately 10–20 base pairs outside of the recognition site. Preferably, the Type IIS restriction enzymes used are those that generate a 5' overhang and a recessed 3' end, including but not limited to BceA I and BsmF I (see e.g. Table I). In a most preferred embodiment, the second primer (either forward or reverse), which anneals close to the locus of interest, contains a restriction enzyme recognition sequence for BsmF I or BceA I. The Type IIS restriction enzyme BsmF I recognizes the nucleic acid sequence GGGAC, and cuts 14 nucleotides from the recognition site on the antisense strand and 10 nucleotides from the recognition site on the sense strand. Digestion with BsmF I generates a 5' overhang of four (4) bases.

For example, if the second primer is designed so that after amplification the restriction enzyme recognition site is 13 bases from the locus of interest, then after digestion, the locus of interest is the first base in the 5' overhang (reading 3' to 5'), and the recessed 3' end is one base upstream of the locus of interest. The 3' recessed end can be filled in with a nucleotide that is complementary to the locus of interest. One base of the overhang can be filled in using dideoxynucleotides. However, 1, 2, 3, or all 4 bases of the overhang can be filled in using deoxynucleotides or a mixture of dideoxynucleotides and deoxynucleotides.

The restriction enzyme BsmF I cuts DNA ten (10) nucleotides from the recognition site on the sense strand and fourteen (14) nucleotides from the recognition site on the antisense strand. However, in a sequence dependent manner, the restriction enzyme BsmF I also cuts eleven (11) nucleotides from the recognition site on the sense strand and fifteen (15) nucleotides from the recognition site on the antisense strand. Thus, two populations of DNA molecules exist after digestion: DNA molecules cut at 10/14 and DNA molecules cut at 11/15. If the recognition site for BsmF I is 13 bases from the locus of interest in the amplified product, then DNA molecules cut at the 11/15 position will generate a 5' overhang that contains the locus of interest in the second position of the overhang (reading 3' to 5'). The 3' recessed end of the DNA molecules can be filled in with labeled nucleotides. For example, if labeled dideoxynucleotides are used, the 3' recessed end of the molecules cut at 11/15 would be filled in with one base, which corresponds to the base upstream of the locus of interest, and the 3' recessed end of molecules cut at 10/14 would be filled in with one base, which corresponds to the locus of interest. The DNA molecules that have been cut at the 10/14 position and the DNA molecules that have been cut at the 11/15 position can be separated by size, and the incorporated nucleotides detected. This allows detection of both the nucleotide before the locus of interest, detection of the locus of interest, and potentially the three bases pairs after the locus of interest.

Alternatively, if the base upstream of the locus of interest and the locus of interest are different nucleotides, then the 3' recessed end of the molecules cut at 11/15 can be filled in with deoxynucleotide that is complementary to the upstream base. The remaining deoxynucleotide is washed away, and the locus of interest site can be filled in with either labeled deoxynucleotides, unlabeled deoxynucleotides, labeled dideoxynucleotides, or unlabeled dideoxynucleotides. After the fill in reaction, the nucleotide can be detected by any suitable method. Thus, after the first fill in reaction with dNTP, the 3'recessed end of the molecules cut at 10/14 and 11/15 is upstream of the locus of interest. The 3' recessed end can now be filled in one base, which corresponds to the locus of interest, two bases, three bases or four bases.

Alternatively, if the base upstream of the locus of interest and the base downstream of the locus of interest are reported to be the same, the 3' recessed end of the molecules cut at 11/15 can be "filled in" with unlabeled deoxynucleotide, followed by a "fill in" with labeled dideoxynucleotide. For example, if the nucleotide upstream of the locus of interest is a cytosine, and a cytosine is a potential nucleotide at the locus of interest, and an adenosine is the first nucleotide 3' of the locus of interest, a "fill in" reaction can be performed with unlabeled deoxyguanine triphosphate (dGTP), followed by a fill in with labeled dideoxythymidine triphosphate. If the locus of interest contains a cytosine, the ddTTP will be incorporated and detected. However, if the locus of interest does not contain a cytosine, the dGTP will not be incorporated, which prevents incorporation of the ddTTP.

The restriction enzyme BceA I recognizes the nucleic acid sequence ACGGC and cuts 12 (twelve) nucleotides from the recognition site on the sense strand and 14 (fourteen) nucleotides from the recognition site on the antisense strand. If the distance from the recognition site for BceA I on the second primer is designed to be thirteen (13) bases from the locus of interest (see FIGS. 4A–4D), digestion with BceA I will generate a 5' overhang of two bases, which contains the locus of interest, and a recessed 3' end that is upstream of the locus of interest. The locus of interest is the first nucleotide in the 5' overhang (reading 3' to 5').

Alternative cutting is also seen with the restriction enzyme BceA I, although at a much lower frequency than is seen with BsmF I. The restriction enzyme BceA I can cut thirteen (13) nucleotides from the recognition site on the sense strand and fifteen (15) nucleotides from the recognition site on the antisense strand. Thus, two populations of DNA molecules exist: DNA molecules cut at 12/14 and DNA molecules cut at 13/15. If the restriction enzyme recognition site is 13 bases from the locus of interest in the amplified product, DNA molecules cut at the 13/15 position yield a 5' overhang, which contains the locus of interest in the second position of the overhang (reading 3' to 5'). Labeled dideoxynucleotides can be used to fill in the 3' recessed end of the DNA molecules. The DNA molecules cut at 13/15 will have the base upstream of the locus of interest filled in, and the DNA molecules cut at 12/14 will have the locus of interest site filled in. The DNA molecules cut at 13/15 and those cut at 12/14 can be separated by size, and the incorporated nucleotide detected. Thus, the alternative cutting can be used to obtain additional sequence information.

Alternatively, if the two bases in the 5' overhang are different, the 3' recessed end of the DNA molecules, which were cut at 13/15, can be filled in with the deoxynucleotide complementary to the first base in the overhang, and excess deoxynucleotide washed away. After filling in, the 3' recessed end of the DNA molecules that were cut at 12/14 and the DNA molecules that were cut at 13/15 are upstream of the locus of interest. The 3' recessed ends can be filled with either labeled dideoxynucleotides, unlabeled dideoxynucleotides, labeled deoxynucleotides, or unlabeled deoxynucleotides.

If the primers provide different restriction sites for certain of the loci of interest that were copied, all the necessary restriction enzymes can be added together to digest the copied DNA simultaneously. Alternatively, the different restriction digests can be made in sequence, for example, using one restriction enzyme at a time, so that only the product that is specific for that restriction enzyme is digested.

Incorporation of Labeled Nucleotides

Digestion with the restriction enzyme that recognizes the sequence on the second primer generates a recessed 3' end and a 5' overhang, which contains the locus of interest (FIG. 1G). The recessed 3' end can be filled in using the 5' overhang as a template in the presence of unlabeled or labeled nucleotides or a combination of both unlabeled and labeled nucleotides. The nucleotides can be labeled with any type of chemical group or moiety that allows for detection including but not limited to radioactive molecules, fluorescent molecules, antibodies, antibody fragments, haptens, carbohydrates, biotin, derivatives of biotin, phosphorescent moieties, luminescent moieties, electrochemiluminescent moieties, chromatic moieties, and moieties having a detectable electron spin resonance, electrical capacitance, dielectric constant or electrical conductivity. The nucleotides can be labeled with one or more than one type of chemical group or moiety. Each nucleotide can be labeled with the same chemical group or moiety. Alternatively, each different nucleotide can be labeled with a different chemical group or moiety. The labeled nucleotides can be dNTPs, ddNTPs, or a mixture of both dNTPs and ddNTPs. The unlabeled nucleotides can be dNTPs, ddNTPs or a mixture of both dNTPs and ddNTPs.

Any combination of nucleotides can be used to incorporate nucleotides including but not limited to unlabeled deoxynucleotides, labeled deoxynucleotides, unlabeled dideoxynucleotides, labeled dideoxynucleotides, a mixture of labeled and unlabeled deoxynucleotides, a mixture of labeled and unlabeled dideoxynucleotides, a mixture of labeled deoxynucleotides and labeled dideoxynucleotides, a mixture of labeled deoxynucleotides and unlabeled dideoxynucleotides, a mixture of unlabeled deoxynucleotides and unlabeled dideoxynucleotides, a mixture of unlabeled deoxynucleotides and labeled dideoxynucleotides, dideoxynucleotide analogues, deoxynucleotide analogues, a mixture of dideoxynucleotide analogues and deoxynucleotide analogues, phosphorylated nucleoside analogues, 2-deoxynucleoside-5' triphosphates and modified 2'-deoxynucleoside triphosphates.

For example, as shown in FIG. 1H, in the presence of a polymerase, the 3' recessed end can be filled in with fluorescent ddNTP using the 5' overhang as a template. The incorporated ddNTP can be detected using any suitable method including but not limited to fluorescence detection.

All four nucleotides can be labeled with different fluorescent groups, which will allow one reaction to be performed in the presence of all four labeled nucleotides. Alternatively, five separate "fill in" reactions can be performed for each locus of interest; each of the four reactions will contain a different labeled nucleotide (e.g. ddATP*, ddTTP*, ddUTP*, ddGTP*, or ddCTP*, where * indicates a labeled nucleotide). Each nucleotide can be labeled with different chemical groups or the same chemical groups. The labeled nucleotides can be dideoxynucleotides or deoxynucleotides.

In another embodiment, nucleotides can be labeled with fluorescent dyes including but not limited to fluorescein, pyrene, 7-methoxycoumarin, Cascade Blue.TM., Alexa Flur 350, Alexa Flur 430, Alexa Flur 488, Alexa Flur 532, Alexa Flur 546, Alexa Flur 568, Alexa Flur 594, Alexa Flur 633, Alexa Flur 647, Alexa Flur 660, Alexa Flur 680, AMCA-X, dialkylaminocoumarin, Pacific Blue, Marina Blue, BODIPY 493/503, BODIPY Fl-X, DTAF, Oregon Green 500, Dansyl-X, 6-FAM, Oregon Green 488, Oregon Green 514, Rhodamine Green-X, Rhodol Green, Calcein, Eosin, ethidium bromide, NBD, TET, 2', 4', 5', 7' tetrabromosulfonefluorescien, BODIPY-R6G, BODIPY-Fl BR2, BODIPY 530/550, HEX, BODIPY 558/568, BODIPY-TMR-X., PyMPO, BODIPY 564/570, TAMRA, BODIPY 576/589, Cy3, Rhodamine Red-x, BODIPY 581/591, carboxyXrhodamine, Texas Red-X, BODIPY-TR-X., Cy5, SpectrumAqua, SpectrumGreen #1, SpectrumGreen #2, SpectrumOrange, SpectrumRed, or naphthofluorescein.

In another embodiment, the "fill in" reaction can be performed with fluorescently labeled dNTPs, wherein the nucleotides are labeled with different fluorescent groups. The incorporated nucleotides can be detected by any suitable method including but not limited to Fluorescence Resonance Energy Transfer (FRET).

In another embodiment, a mixture of both labeled ddNTPs and unlabeled dNTPs can be used for filling in the recessed 3' end of the SNP or locus of interest. Preferably, the 5' overhang consists of more than one base, including but not limited to 2, 3, 4, 5, 6 or more than 6 bases. For example, if the 5' overhang consists of the sequence "XGAA," wherein X is the locus of interest, e.g. SNP, then filling in with a mixture of labeled ddNTPs and unlabeled dNTPs will produce several different DNA fragments. If a labeled ddNTP is incorporated at position "X," the reaction will terminate and a single labeled base will be incorporated. If however, an unlabeled dNTP is incorporated, the polymerase continues to incorporate other bases until a labeled ddNTP is incorporated. If the first two nucleotides incorporated are dNTPs, and the third is a ddNTP, the 3' recessed end will be extend by three bases. This DNA fragment can be separated from the other DNA fragments that were extended by 1, 2, or 4 bases by size. A mixture of labeled ddNTPs and unlabeled dNTPs will allow all bases of the overhang to be filled in, and provides additional sequence information about the locus of interest, e.g. SNP (see FIGS. 7E and 9D).

After incorporation of the labeled nucleotide, the amplified DNA can be digested with a restriction enzyme that recognizes the sequence provided by the first primer. For example, in FIG. 1I, the amplified DNA is digested with a restriction enzyme that binds to region "a," which releases the DNA fragment containing the incorporated nucleotide from the streptavidin matrix.

Alternatively, one primer of each primer pair for each locus of interest can be attached to a solid support matrix including but not limited to a well of a microtiter plate. For example, streptavidin-coated microtiter plates can be used for the amplification reaction with a primer pair, wherein one primer is biotinylated. First, biotinylated primers are bound to the streptavidin-coated microtiter plates. Then, the plates are used as the reaction vessel for PCR amplification of the loci of interest. After the amplification reaction is complete, the excess primers, salts, and template DNA can be removed by washing. The amplified DNA remains attached to the microtiter plate. The amplified DNA can be digested with a restriction enzyme that recognizes a sequence on the second primer and generates a 5' overhang, which contains the locus of interest. The digested fragments can be removed by washing. After digestion, the SNP site or locus of interest is exposed in the 5' overhang. The recessed 3' end is filled in with a labeled nucleotide, including but not limited to, fluorescent ddNTP in the presence of a polymerase. The labeled DNA can be released into the supernatant in the microtiter plate by digesting with a restriction enzyme that recognizes a sequence in the 5' region of the first primer.

Analysis of the Locus of Interest

The labeled loci of interest can be analyzed by a variety of methods including but not limited to fluorescence detection, DNA sequencing gel, capillary electrophoresis on an automated DNA sequencing machine, microchannel electrophoresis, and other methods of sequencing, mass spectrometry, time of flight mass spectrometry, quadrupole mass spectrometry, magnetic sector mass spectrometry, electric sector mass spectrometry infrared spectrometry, ultraviolet spectrometry, palentiostatic amperometry or by DNA hybridization techniques including Southern Blots, Slot Blots, Dot Blots, and DNA microarrays, wherein DNA fragments would be useful as both "probes" and "targets," ELISA, fluorimetry, and Fluorescence Resonance Energy Transfer (FRET).

The loci of interest can be analyzed using gel electrophoresis followed by fluorescence detection of the incorporated nucleotide. Another method to analyze or read the loci of interest is to use a fluorescent plate reader or fluorimeter directly on the 96-well streptavidin coated plates. The plate can be placed onto a fluorescent plate reader or scanner such as the Pharmacia 9200 Typhoon to read each locus of interest.

Alternatively, the PCR products of the loci of interest can be pooled and after "filling in," (FIG. 10) the products can be separated by size, using any method appropriate for the same, and then analyzed using a variety of techniques including but not limited to fluorescence detection, DNA sequencing gel, capillary electrophoresis on an automated DNA sequencing machine, microchannel electrophoresis, other methods of sequencing, DNA hybridization techniques including Southern Blots, Slot Blots, Dot Blots, and DNA microarrays, mass spectrometry, time of flight mass spectrometry, quadrupole mass spectrometry, magnetic sector mass spectrometry, electric sector mass spectrometry infrared spectrometry, ultraviolet spectrometry, palentiostatic amperometry. For example, polyacrylamide gel electrophoresis can be used to separate DNA by size and the gel can be scanned to determine the color of fluorescence in each band (using e.g. ABI 377 DNA sequencing machine or a Pharmacia Typhoon 9200).

In another embodiment, the sequence of the locus of interest can be determined by detecting the incorporation of a nucleotide that is 3' to the locus of interest provided it is a different nucleotide from the possible nucleotides at the locus of interest. This embodiment is especially useful for the sequencing and detection of SNPs. The efficiency and rate at which DNA polymerases incorporate nucleotides varies for each nucleotide. However, one labeled nucleotide can be used to detect the nucleotide at the locus of interest.

According to the data from the Human Genome Project, 99% of all SNPs are binary. The sequence of the human genome can be used to determine the nucleotide that is 3' to the SNP of interest. When the nucleotide that is 3' to the SNP site differs from the possible nucleotides at the SNP site, a nucleotide that is one or more than one base 3' to the SNP can be used to determine the sequence of the SNP.

For example, suppose the sequence of SNP X on chromosome 13 is to be determined. The sequence of the human genome indicates that SNP X can either be adenosine or guanine and that the 3' nucleotide is thymidine. A primer that contains a restriction enzyme recognition site for BsmF I, which is designed to be 13 bases from the locus of interest after amplification, is used to amplify SNP X. Digestion with the restriction enzyme BsmF I generates a 5' overhang that contains the locus of interest, which can either be adenosine or guanine. If the nucleotide downstream (3') of the locus of interest is different from the possible nucleotides at the SNP site, the digestion products can be split into two "fill in" reactions: one contains dTTP, and the other reaction contains dCTP. If the locus of interest is homozygous for guanine, only the DNA molecules that were mixed with dCTP will be filled in. If the locus of interest is homozygous for adenosine, only the DNA molecules that were mixed with dTTP will be filled in. If the locus of interest is heterozygous, the DNA molecules that were mixed with dCTP will be filled in as well as the DNA molecules that were mixed with dTTP. After washing to remove the excess dNTP, the samples are filled in with labeled ddATP, which is complimentary to the nucleotide (thymidine) that is 3' to the locus of interest. The DNA molecules that were filled in by the previous reaction will be filled in with labeled ddATP. If the individual is homozygous for adenosine, the DNA molecules that were mixed with dTTP subsequently will be filled in with the labeled ddATP. However, the DNA molecules that were mixed with dCTP, would not have incorporated that nucleotide, and therefore, could not incorporate the ddATP. Detection of labeled ddATP only in the molecules that were mixed with dTTP indicates that the nucleotide at SNP X on chromosome 13 is adenosine. Thus, one labeled nucleotide can be used to detect heterozygous populations of loci of interest.

In another embodiment, large scale screening for the presence or absence of single nucleotide mutations can be performed. One to tens to hundreds to thousands of loci of interest on a single chromosome or on multiple chromosomes can be amplified with primers as described above in the "Primer Design" section. The primers can be designed so that each amplified loci of interest is of a different size (FIG. 2). The amplified loci of interest that are predicted, based on the published wild type sequences, to have the same nucleotide at the locus of interest can be pooled together, bound to a solid support, including wells of a microtiter plate coated with streptavidin, and digested with the restriction enzyme that will bind the recognition site on the second primer. After digestion, the 3' recessed end can be filled in with a mixture of labeled ddATP, ddTTP, ddGTP, ddCTP, where each nucleotide is labeled with a different group. After washing to remove the excess nucleotide, the fluorescence spectra can be detected using a plate reader or fluorimeter directly on the streptavidin coated plates. If all 50 loci of interest contain the wild type nucleotide, only one fluorescence spectra will be seen. However, if one or more than one of the 50 loci of interest contain a mutation, a different nucleotide will be incorporated and other fluorescence pattern(s) will be seen. The nucleotides can be released from the solid matrix, and analyzed on a sequencing gel to determine the loci of interest that contained the mutations. As each of the 50 loci of interest are of different size, they will separate on a sequencing gel.

The multiple loci of interest can be of a DNA sample from one individual representing multiple loci of interest on a single chromosome, multiple chromosomes, multiple genes, a single gene, or any combination thereof. The multiple loci of interest also can represent the same locus of interest but from multiple individuals. For example, 50 DNA samples from 50 different individuals can be pooled and analyzed to determine a particular nucleotide of interest at gene "X."

When human data is being analyzed, the known sequence can be a specific sequence that has been determined from one individual (including e.g. the individual whose DNA is currently being analyzed), or it can be a consensus sequence such as that published as part of the human genome.

Kits

The methods of the invention are most conveniently practiced by providing the reagents used in the methods in the form of kits. A kit preferably contains one or more of the following components: written instructions for the use of the kit, appropriate buffers, salts, DNA extraction detergents, primers, nucleotides, labeled nucleotides, 5' end modification materials, and if desired, water of the appropriate purity, confined in separate containers or packages, such components allowing the user of the kit to extract the appropriate nucleic acid sample, and analyze the same according to the methods of the invention. The primers that are provided with the kit will vary, depending upon the purpose of the kit and the DNA that is desired to be tested using the kit.

A kit can also be designed to detect a desired or variety of single nucleotide polymorphisms, especially those associated with an undesired condition or disease. For example, one kit can comprise, among other components, a set or sets of primers to amplify one or more loci of interest associated with breast cancer. Another kit can comprise, among other components, a set or sets of primers for genes associated with a predisposition to develop type I or type II diabetes. Still, another kit can comprise, among other components, a set or sets of primers for genes associated with a predisposition to develop heart disease. Details of utilities for such kits are provided in the "Utilities" section below.

Utilities

The methods of the invention can be used whenever it is desired to know the sequence of a certain nucleic acid, locus of interest or loci of interest therein. The method of the invention is especially useful when applied to genomic DNA. When DNA from an organism-specific or species-specific locus or loci of interest is amplified, the method of the invention can be used in genotyping for identification of the source of the DNA, and thus confirm or provide the identity of the organism or species from which the DNA sample was derived. The organism can be any nucleic acid containing organism, for example, virus, bacterium, yeast, plant, animal or human.

Within any population of organisms, the method of the invention is useful to identify differences between the sequence of the sample nucleic acid and that of a known nucleic acid. Such differences can include, for example, allelic variations, mutations, polymorphisms and especially single nucleotide polymorphisms.

In a preferred embodiment, the method of the invention provides a method for identification of single nucleotide polymorphisms.

In a preferred embodiment, the method of the invention provides a method for identification of the presence of a disease, especially a genetic disease that arises as a result of the presence of a genomic sequence, or other biological condition that it is desired to identify in an individual for which it is desired to know the same. The identification of such sequence in the subject based on the presence of such genomic sequence can be used, for example, to determine if the subject is a carrier or to assess if the subject is predisposed to developing a certain genetic trait, condition or disease. The method of the invention is especially useful in prenatal genetic testing of parents and child. Examples of some of the diseases that can be diagnosed by this invention are listed in Table II.

TABLE II

Achondroplasia
Adrenoleukodysrophy, X-Linked
Agammaglobulinemia, X-Linked
Alagille Syndrome
Alpha-Thalassemia X-Linked Mental Retardation Syndrome
Alzheimer Disease
Alzheimer Disease, Early-Onset Familial
Amyotrophic Lateral Schlerosis Overview
Androgen Insensitivity Syndrome
Angelman Syndrome
Ataxia Overview, Hereditary
Ataxia-Telangiectasia
Becker Muscular Dystrophy (also The Dystrophinopathies)
Beckwith-Wiedemann Syndrome
Beta-Thalassern ia
Biotinidase Deficiency
Branchiootorenal Syndrome
BRCA1 and BRCA2 Hereditary Breast/Ovarian Cancer
Breast Cancer
CADASIL
Canavan Disease
Cancer
Charcot-Marie-Tooth Hereditary Neuropathy
Charcot-Marie-Tooth Neuropathy Type 1

TABLE II-continued

Charcot-Marie-Tooth Neuropathy Type 2
Charcot-Marie-Tooth Neuropathy Type 4
Charcot-Marie-Tooth Neuropathy Type X
Cockayne Syndrome
Colon Cancer
Contractural Arachnodactyly, Congenital
Craniosynostosis Syndromes (FGFR-Related)
Cystic Fibrosis
Cystinosis
Deafness and Hereditary Hearing Loss
DRPLA (Dentatorubral-Pallidoluysian Atrophy)
DiGeorge Syndrome (also 22q11 Deletion Syndrome)
Dilated Cardiomyopathy, X-Linked
Down Syndrome (Trisomy 21)
Duchenne Muscular Dystrophy (also The Dystrophinopathies)
Dystonia, Early-Onset Primary (DYT1)
Dystrophinopathies, The
Ehlers-Danlos Syndrome, Kyphoscoliotic Form
Ehlers-Danlos Syndrome, Vascular Type
Epidermolysis Bullosa Simplex
Exostoses, Hereditary Multiple
Facioscapulohumeral Muscular Dystrophy
Factor V Leiden Thrombophilia
Familial Adenomatous Polyposis (FAP)
Familial Mediterranean Fever
Fragile X Syndrome
Friedreich Ataxia
Frontotemporal Demetia with Parkinsonism-17
Galactosemia
Gaucher Disease
Hemochromatosis, Hereditary
Hemophilia A
Hemophilia B
Hemorrhagic Telangiectasia, Hereditary
Hearing Loss and Deafness, Nonsyndromic, DFNA3 (Connexin 26)
Hearing Loss and Deafness, Nonsyndromic, DFNB1 (Connexin 26)
Hereditary Spastic Paraplegia
Herrnansky-Pudlak Syndrome
Hexosarn in idase A Deficiency (also Tay-Sachs)
Huntington Disease
Hypochondroplasia
Ichthyosis, Congenital, Autosomal Recessive
Incontinentia Pigmenti
Kennedy Disease (also Spinal and Bulbar Muscular Atrophy)
Krabbe Disease
Leber Hereditary Optic Neuropathy
Lesch-Nyhan Syndrome
Leukemias
Li-Fraumeni Syndrome
Limb-Girdle Muscular Dystrophy
Lipoprotein Lipase Deficiency, Familial
Lissencephaly
Marfan Syndrome
MELAS (Mitochondrial Encephalomyopathy, Lactic Acidosis, and Stroke-Like Episodes)
Monosomies
Multiple Endocrine Neoplasia Type 2
Multiple Exostoses, Hereditary
Muscular Dystrophy, Congenital
Myotonic Dystrophy
Nephrogenic Diabetes Insipidus
Neurofibromatosis 1
Neurofibromatosis 2
Neuropathy with Liability to Pressure Palsies, Hereditary
Niemann-Pick Disease Type C
Nijmegen Breakage Syndrome
Norrie Disease
Oculocutaneous Albinism Type I
Oculopharyngeal Muscular Dystrophy
Ovarian Cancer
Pallister-Hall Syndrome
Parkin Type of Juvenile Parkinson Disease
Pelizaeus-Merzbacher Disease
Pendred Syndrome
Peutz-Jeghers Syndrome
Phenylalanine Hydroxylase Deficiency
Prader-Willi Syndrome
PROP1-Related Combined Pituitary Hormone Deficiency (CPHD)
Prostate Cancer

TABLE II-continued

Retinitis Pigmentosa
Retinoblastoma
Rothmund-Thomson Syndrome
Smith-Lemli-Opitz Syndrome
Spastic Paraplegia, Hereditary
Spinal and Bulbar Muscular Atrophy (also Kennedy Disease)
Spinal Muscular Atrophy
Spinocerebellar Ataxia Type 1
Spinocerebellar Ataxia Type 2
Spinocerebellar Ataxia Type 3
Spinocerebellar Ataxia Type 6
Spinocerebellar Ataxia Type 7
Stickler Syndrome (Hereditary Arthroophthalmopathy)
Tay-Sachs (also GM2 Gangliosidoses)
Trisomies
Tuberous Sclerosis Complex
Usher Syndrome Type I
Usher Syndrome Type II
Velocardiofacial Syndrome (also 22q11 Deletion Syndrome)
Von Hippel-Lindau Syndrome
Williams Syndrome
Wilson Disease
X-Linked Adrenoleukodystrophy
X-Linked Agammaglobulinemia
X-Linked Dilated Cardiomyopathy (also The Dystrophinopathies)
X-Linked Hypotonic Facies Mental Retardation Syndrome The method of the invention is useful for screening an individual at multiple loci of interest, such as tens, hundreds, or even thousands of loci of interest associated with a genetic trait or genetic disease by sequencing the loci of interest that are associated with the trait or disease state, especially those most frequently associated with such trait or condition. The invention is useful for analyzing a particular set of diseases including but not limited to heart disease, cancer, endocrine disorders, immune disorders, neurological disorders, musculoskeletal disorders, ophthalmologic disorders, genetic abnormalities, trisomies, monosomies, transversions, translocations, skin disorders, and familial diseases.

The method of the invention can be used to genotype microorganisms so as to rapidly identify the presence of a specific microorganism in a substance, for example, a food substance. In that regard, the method of the invention provides a rapid way to analyze food, liquids or air samples for the presence of an undesired biological contamination, for example, microbiological, fungal or animal waste material. The invention is useful for detecting a variety of organisms, including but not limited to bacteria, viruses, fungi, protozoa, molds, yeasts, plants, animals, and archeabacteria. The invention is useful for detecting organisms collected from a variety of sources including but not limited to water, air, hotels, conference rooms, swimming pools, bathrooms, aircraft, spacecraft, trains, buses, cars, offices, homes, businesses, churches, parks, beaches, athletic facilities, amusement parks, theaters, and any other facility that is a meeting place for the public.

The method of the invention can be used to test for the presence of many types of bacteria or viruses in blood cultures from human or animal blood samples.

The method of the invention can also be used to confirm or identify the presence of a desired or undesired yeast strain, or certain traits thereof, in fermentation products, e.g. wine, beer, and other alcohols or to identify the absence thereof.

The method of the invention can also be used to confirm or identify the relationship of a DNA of unknown sequence to a DNA of known origin or sequence, for example, for use in criminology, forensic science, maternity or paternity testing, archaeological analysis, and the like.

The method the invention can also be used to determine the genotypes of plants, trees and bushes, and hybrid plants, trees and bushes, including plants, trees and bushes that produce fruits and vegetables and other crops, including but not limited to wheat, barley, corn, tobacco, alfalfa, apples, apricots, bananas, oranges, pears, nectarines, figs, dates, raisins, plums, peaches, apricots, blueberries, strawberries, cranberries, berries, cherries, kiwis, limes, lemons, melons, pineapples, plantains, guavas, prunes, passion fruit, tangerines, grapefruit, grapes, watermelon, cantelope, honeydew melons, pomegranates, persimmons, nuts, artichokes, bean sprouts, beets, cardoon, chayote, endive, leeks, okra, green onions, scallions, shallots, parsnips, sweet potatoes, yams, asparagus, avocados, kohlrabi, rutabaga, eggplant, squash, turnips, pumpkins, tomatoes, potatoes, cucumbers, carrots, cabbage, celery, broccoli, cauliflower, radishes, peppers, spinach, mushrooms, zucchini, onions, peas, beans, and other legumes.

Especially, the method of the invention is useful to screen a mixture of nucleic acid samples that contain many different loci of interest and/or a mixture of nucleic acid samples from different sources that are to be analyzed for a locus of interest. Examples of large scale screening include taking samples of nucleic acid from herds of farm animals, or crops of food plants such as, for example, corn or wheat, pooling the same, and then later analyzing the pooled samples for the presence of an undesired genetic marker, with individual samples only being analyzed at a later date if the pooled sample indicates the presence of such undesired genetic sequence. An example of an undesired genetic sequence would be the detection of viral or bacterial nucleic acid sequence in the nucleic acid samples taken from the farm animals, for example, mycobacterium or hoof and mouth disease virus sequences or fungal or bacterial pathogen of plants.

Another example where pools of nucleic acid can be used is to test for the presence of a pathogen or gene mutation in samples from one or more tissues from an animal or human subject, living or dead, especially a subject who can be in need of treatment if the pathogen or mutation is detected. For example, numerous samples can be taken from an animal or human subject to be screened for the presence of a pathogen or otherwise undesired genetic mutation, the loci of interest from each biological sample amplified individually, and then samples of the amplified DNA combined for the restriction digestion, "filling in," and detection. This would be useful as an initial screening for the assay of the presence or absence of nucleic acid sequences that would be diagnostic of the presence of a pathogen or mutation. Then, if the undesired nucleic acid sequence of the pathogen or mutation was detected, the individual samples could be separately analyzed to determine the distribution of the undesired sequence. Such an analysis is especially cost effective when there are large numbers of samples to be assayed. Samples of pathogens include the mycobacteria, especially those that cause tuberculosis or paratuberculosis, bacteria, especially bacterial pathogens used in biological warfare, including *Bacillus anthracis*, and virulent bacteria capable of causing food poisoning, viruses, especially the influenza and AIDS virus, and mutations known to be associated with malignant cells. Such an analysis would also be advantageous for the large scale screening of food products for pathogenic bacteria.

Conversely, the method of the invention can be used to detect the presence and distribution of a desired genetic sequence at various locations in a plant, animal or human subject, or in a population of subjects, e.g. by screening of a combined sample followed by screening of individual samples, as necessary.

The method of the invention is useful for analyzing genetic variations of an individual that have an effect on drug metabolism, drug interactions, and the responsiveness to a drug or to multiple drugs. The method of the invention is especially useful in pharmacogenomics.

Having now generally described the invention, the same will become better understood by reference to certain specific examples which are included herein for purposes of illustration only and are not intended to be limiting unless other wise specified.

EXAMPLES

The following examples are illustrative only and are not intended to limit the scope of the invention as defined by the claims.

Example 1

DNA sequences were amplified by PCR, wherein the annealing step in cycle 1 was performed at a specified temperature, and then increased in cycle 2, and further increased in cycle 3 for the purpose of reducing non-specific amplification. The TM1 of cycle 1 of PCR was determined by calculating the melting temperature of the 3' region, which anneals to the template DNA, of the second primer. For example, in FIG. 1B, the TM1 can be about the melting temperature of region "c." The annealing temperature was raised in cycle 2, to TM2, which was about the melting temperature of the 3' region, which anneals to the template DNA, of the first primer. For example, in FIG. 1C, the annealing temperature (TM2) corresponds to the melting temperature of region "b'". In cycle 3, the annealing temperature was raised to TM3, which was about the melting temperature of the entire sequence of the second primer For example, in FIG. 1D, the annealing temperature (TM3) corresponds to the melting temperature of region "c"+region "d". The remaining cycles of amplification were performed at TM3.

Preparation of Template DNA

The template DNA was prepared from a 5 ml sample of blood obtained by venipuncture from a human volunteer with informed consent. Blood was collected from 36 volunteers. Template DNA was isolated from each blood sample using QIAamp DNA Blood Midi Kit supplied by QIAGEN (Catalog number 51183). Following isolation, the template DNA from each of the 36 volunteers was pooled for further analysis.

Design of Primers

The following four single nucleotide polymorphisms were analyzed: SNP HC21S00340, identification number as assigned by Human Chromosome 21 cSNP Database, (FIG. 3, lane 1) located on chromosome 21; SNP TSC 0095512 (FIG. 3, lane 2) located on chromosome 1, SNP TSC 0214366 (FIG. 3, lane 3) located on chromosome 1; and SNP TSC 0087315 (FIG. 3, lane 4) located on chromosome 1. The SNP Consortium Ltd database can be accessed at http://snp.cshl.org/, website address effective as of Feb. 14, 2002.

SNP HC21S00340 was amplified using the following primers:

```
First primer:  5' TAGAATAGCACTGAATTCAGGAATACAATCATTGTCAC 3'  (SEQ ID NO:9)

Second primer: 5' ATCACGATAAACGGCCAAACTCAGGTTA 3'             (SEQ ID NO:10)
```

SNP TSC0095512 was amplified using the following primers:

```
First primer:  5' AAGTTTAGATCAGAATTCGTGAAAGCAGAAGTTGTCTG 3'  (SEQ ID NO:11)

Second primer: 5' TCTCCAACTAACGGCTCATCGAGTAAAG 3'             (SEQ ID NO:12)
```

SNP TSC0214366 was amplified using the following primers:

```
First primer:  5' ATGACTAGCTATGAATTCGTTCAAGGTAGAAAATGGAA 3'  (SEQ ID NO:13)

Second primer: 5' GAGAATTAGAACGGCCCAAATCCCACTC 3'             (SEQ ID NO:16)
```

SNP TSC 0087315 was amplified using the following primers:

```
First primer:  5' TTACAATGCATGAATTCATCTTGGTCTCTCAAAGTGC 3'   (SEQ ID NO:15)

Second primer: 5' TGGACCATAAACGGCCAAAAACTGTAAG 3'             (SEQ ID NO:16)
```

All primers were designed such that the 3' region was complementary to either the upstream or downstream sequence flanking each locus of interest and the 5' region contained a restriction enzyme recognition site. The first primer contained a biotin tag at the 5' end and a recognition site for the restriction enzyme EcoRI. The second primer contained the recognition site for the restriction enzyme BceA I.

PCR Reaction

All four loci of interest were amplified from the template genomic DNA using PCR (U.S. Pat. Nos. 4,683,195 and 4,683,202). The components of the PCR reaction were as follows: 40 ng of template DNA, 5 µM first primer, 5 µM second primer, 1× HotStarTaq Master Mix as obtained from Qiagen (Catalog No. 203443). The HotStarTaq Master Mix contained DNA polymerase, PCR buffer, 200 µM of each dNTP, and 1.5 mM MgCl$_2$.

Amplification of each template DNA that contained the SNP of interest was performed using three different series of annealing temperatures, herein referred to as low stringency annealing temperature, medium stringency annealing temperature, and high stringency annealing temperature. Regardless of the annealing temperature protocol, each PCR reaction consisted of 40 cycles of amplification. PCR reactions were performed using the HotStarTaq Master Mix Kit supplied by QIAGEN. As instructed by the manufacturer, the reactions were incubated at 95° C. for 15 min. prior to the first cycle of PCR. The denaturation step after each extension step was performed at 95° C. for 30 sec. The annealing reaction was performed at a temperature that permitted efficient extension without any increase in temperature.

The low stringency annealing reaction comprised three different annealing temperatures in each of the first three cycles. The annealing temperature for the first cycle was 37° C. for 30 sec.; the annealing temperature for the second cycle was 57° C. for 30 sec.; the annealing temperature for the third cycle was 64° C. for 30 sec. Annealing was performed at 64° C. for subsequent cycles until completion.

As shown in the photograph of the gel (FIG. 3A), multiple bands were observed after amplification of SNP TSC 0087315 (lane 4). Amplification of SNP HC21S00340 (lane 1), SNP TSC0095512 (lane 2), and SNP TSC0214366 (lane 3) generated a single band of high intensity and one band of faint intensity, which was of higher molecular weight. When the low annealing temperature conditions were used, the correct size product was generated and this was the predominant product in each reaction.

The medium stringency annealing reaction comprised three different annealing temperatures in each of the first three cycles. The annealing temperature for the first cycle was 40° C. for 30 seconds; the annealing temperature for the second cycle was 60° C. for 30 seconds; and the annealing temperature for the third cycle was 67° C. for 30 seconds. Annealing was performed at 67° C. for subsequent cycles until completion. Similar to what was observed under low stringency annealing conditions, amplification of SNP TSC0087315 (FIG. 3B, lane 4) generated multiple bands under conditions of medium stringency. Amplification of the other three SNPs (lanes 1–3) produced a single band. These results demonstrate that variable annealing temperatures can be used to cleanly amplify loci of interest from genomic DNA with a primer that has an annealing length of 13 bases.

The high stringency annealing reaction was comprised of three different annealing temperatures in each of the first three cycles. The annealing temperature of the first cycle was 46° C. for 30 seconds; the annealing temperature of the second cycle was 65° C. for 30 seconds; and the annealing temperature for the third cycle was 72° C. for 30 seconds.

Annealing was performed at 72° C. for subsequent cycles until completion. As shown in the photograph of the gel (FIG. 3C), amplification of SNP TSC0087315 (lane 4) using the high stringency annealing temperatures generated a single band of the correct molecular weight. By raising the annealing temperatures for each of the first three cycles, non-specific amplification was eliminated. Amplification of SNP TSC0095512 (lane 2) generated a single band. SNPs HC21S00340 (lane 1), and TSC0214366 (lane 3) failed to amplify at the high stringency annealing temperatures, however, at the medium stringency annealing temperatures, these SNPs amplified as a single band. These results demonstrate that variable annealing temperatures can be used to reduce non-specific PCR products, as demonstrated for SNP TSC0087315 (FIG. 3, lane 4).

Example 2

SNPs on chromosomes 1 (TSC0095512), 13 (TSC0264580), and 21 (HC21S00027) were analyzed. SNP TSC0095512 was analyzed using two different sets of primers, and SNP HC21S00027 was analyzed using two types of reactions for the incorporation of nucleotides.

Preparation of Template DNA

The template DNA was prepared from a 5 ml sample of blood obtained by venipuncture from a human volunteer with informed consent. Template DNA was isolated using the QIAmp DNA Blood Midi Kit supplied by QIAGEN (Catalog number 51183). The template DNA was isolated as per instructions included in the kit. Following isolation, template DNA from thirty-six human volunteers were pooled together and cut with the restriction enzyme EcoRI. The restriction enzyme digestion was performed as per manufacturer's instructions.

Design of Primers

SNP HC21S00027 was amplified by PCR using the following primer set:

```
First primer:  5' ATAACCGTATGCGAATTCTATAATTTTCCTGATAAAGG 3' (SEQ ID NO:17)
Second primer: 5' CTTAAATCAGGGGACTAGGTAAACTTCA 3'            (SEQ ID NO:18)
```

The first primer contained a biotin tag at the extreme 5' end, and the nucleotide sequence for the restriction enzyme EcoRI. The second primer contained the nucleotide sequence for the restriction enzyme BsmF I (FIG. 4A).

Also, SNP HC21S00027 was amplified by PCR using the same first primer but a different second primer with the following sequence:

```
Second primer:
5' CTTAAATCAGACGGCTAGGTAAACTTCA 3'   (SEQ ID NO:19)
```

This second primer contained the recognition site for the restriction enzyme BceA I (FIG. 4B).

SNP TSC0095512 was amplified by PCR using the following primers:

```
First primer:  5' AAGTTTAGATCAGAATTCGTGAAAGCAGAAGTTGTCTG 3' (SEQ ID NO:11)
Second primer: 5' TCTCCAACTAGGGACTCATCGAGTAAAG 3'           (SEQ ID NO:20)
```

The first primer had a biotin tag at the 5' end and contained a restriction enzyme recognition site for EcoRI. The second primer contained a restriction enzyme recognition site for BsmF I (FIG. 4C).

Also, SNP TSC0095512 was amplified using the same first primer and a different second primer with the following sequence:

```
Second primer:
5' TCTCCAACTAACGGCTCATCGAGTAAAG 3'   (SEQ ID NO:12)
```

This second primer contained the recognition site for the restriction enzyme BceA I (FIG. 4D).

SNP TSC0264580, which is located on chromosome 13, was amplified with the following primers:

```
First primer: 5' AACGCCGGGCGAGAATTCAGTTTTTCAACTTGCAAGG 3' (SEQ ID NO:21)

Second primer:
5' CTACACATATCTGGGACGTTGGCCATCC 3'    (SEQ ID NO:22)
```

The first primer contained a biotin tag at the extreme 5' end and had a restriction enzyme recognition site for EcoRI. The second primer contained a restriction enzyme recognition site for BsmF I.

PCR Reaction

All loci of interest were amplified from the template genomic DNA using the polymerase chain reaction (PCR, U.S. Pat. Nos. 4,683,195 and 4,683,202, incorporated herein by reference). In this example, the loci of interest were amplified in separate reaction tubes but they could also be amplified together in a single PCR reaction. For increased specificity, a "hot-start" PCR was used. PCR reactions were performed using the HotStarTaq Master Mix Kit supplied by QIAGEN (catalog number 203443). The amount of template DNA and primer per reaction can be optimized for each locus of interest but in this example, 40 ng of template human genomic DNA and 5 μM of each primer were used. Forty cycles of PCR were performed. The following PCR conditions were used:

(1) 95° C. for 15 minutes and 15 seconds;
(2) 37° C. for 30 seconds;
(3) 95° C. for 30 seconds;
(4) 57° C. for 30 seconds;

(5) 95° C. for 30 seconds;
(6) 64° C. for 30 seconds;
(7) 95° C. for 30 seconds;
(8) Repeat steps 6 and 7 thirty nine (39) times;
(9) 72° C. for 5 minutes.

In the first cycle of PCR, the annealing temperature was about the melting temperature of the 3' annealing region of the second primers, which was 37° C. The annealing temperature in the second cycle of PCR was about the melting temperature of the 3' region, which anneals to the template DNA, of the first primer, which was 57° C. The annealing temperature in the third cycle of PCR was about the melting temperature of the entire sequence of the second primer, which was 64° C. The annealing temperature for the remaining cycles was 64° C. Escalating the annealing temperature from TM1 to TM2 to TM3 in the first three cycles of PCR greatly improves specificity. These annealing temperatures are representative, and the skilled artisan will understand the annealing temperatures for each cycle are dependent on the specific primers used.

The temperatures and times for denaturing, annealing, and extension, can be optimized by trying various settings and using the parameters that yield the best results. Schematics of the PCR products for SNP HC21S00027 and SNP TSC0095512 are shown in FIGS. 5A–5D.

Purification of Fragment of Interest

The PCR products were separated from the genomic template DNA. Each PCR product was divided into four separate reaction wells of a Streptawell, transparent, High-Bind plate from Roche Diagnostics GmbH (catalog number 1 645 692, as listed in Roche Molecular Biochemicals, 2001 Biochemicals Catalog). The first primers contained a 5' biotin tag so the PCR products bound to the Streptavidin coated wells while the genomic template DNA did not. The streptavidin binding reaction was performed using a Thermomixer (Eppendorf) at 1000 rpm for 20 min. at 37° C. Each well was aspirated to remove unbound material, and washed three times with 1×PBS, with gentle mixing (Kandpal et al., Nucl. Acids Res. 18:1789–1795 (1990); Kaneoka et al., Biotechniques 10:30–34 (1991); Green et al., Nucl. Acids Res. 18:6163–6164 (1990)).

Restriction Enzyme Digestion of Isolated Fragments

Figure 6B:
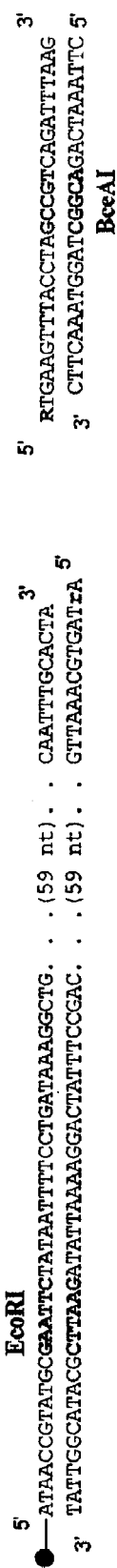

The purified PCR products were digested with the restriction enzyme that bound the recognition site incorporated into the PCR products from the second primer. SNP HC21S00027 (FIGS. 6A and 6B) and SNP TSC0095512 (FIGS. 6C and 6D) were amplified in separate reactions using two different second primers. FIG. 6A (SNP HC21S00027) and FIG. 6C (SNP TSC0095512) depict the PCR products after digestion with the restriction enzyme BsmF I (New England Biolabs catalog number R0572S). FIG. 6B (SNP HC21S00027) and FIG. 6D (SNP TSC0095512) depict the PCR products after digestion with the restriction enzyme BceA I (New England Biolabs, catalog number R0623S). The digests were performed in the Streptawells following the instructions supplied with the restriction enzyme. SNP TSC0264580 was digested with BsmF I. After digestion with the appropriate restriction enzyme, the wells were washed three times with PBS to remove the cleaved fragments.

Incorporation of Labeled Nucleotide

The restriction enzyme digest described above yielded a DNA fragment with a 5' overhang, which contained the SNP site or locus of interest and a 3' recessed end. The 5' overhang functioned as a template allowing incorporation of a nucleotide or nucleotides in the presence of a DNA polymerase.

For each SNP, four separate fill in reactions were performed; each of the four reactions contained a different fluorescently labeled ddNTP (ddATP, ddTTP, ddGTP, or ddCTP). The following components were added to each fill in reaction: 1 µl of a fluorescently labeled ddNTP, 0.5 µl of unlabeled ddNTPs (40 µM), which contained all nucleotides except the nucleotide that was fluorescently labeled, 2 µl of 10× sequenase buffer, 0.25 µl of Sequenase, and water as needed for a 20 µl reaction. All of the fill in reactions were performed at 40° C. for 10 min. Non-fluorescently labeled ddNTP was purchased from Fermentas Inc. (Hanover, Md.). All other labeling reagents were obtained from Amersham (Thermo Sequenase Dye Terminator Cycle Sequencing Core Kit, US 79565). In the presence of fluorescently labeled ddNTPs, the 3' recessed end was extended by one base, which corresponds to the SNP or locus of interest (FIGS. 7A–7D).

A mixture of labeled ddNTPs and unlabeled dNTPs also was used for the "fill in" reaction for SNP HC21S00027. The "fill in" conditions were as described above except that a mixture containing 40 µM unlabeled dNTPs, 1 µl fluorescently labeled ddATP, 1 µl fluorescently labeled ddTTP, 1 µl fluorescently labeled ddCTP, and 1 µl ddGTP was used. The fluorescent ddNTPs were obtained from Amersham (Thermo Sequenase Dye Terminator Cycle Sequencing Core Kit, US 79565; Amersham did not publish the concentrations of the fluorescent nucleotides). SNP HC21S00027 was digested with the restriction enzyme BsmF I, which generated a 5' overhang of four bases. As shown in FIG. 7E, if the first nucleotide incorporated is a labeled ddNTP, the 3' recessed end is filled in by one base, allowing detection of the SNP or locus of interest. However, if the first nucleotide incorporated is a dNTP, the polymerase continues to incorporate nucleotides until a ddNTP is filled in. For example, the first two nucleotides may be filled in with dNTPs, and the third nucleotide with a ddNTP, allowing detection of the third nucleotide in the overhang. Thus, the sequence of the entire 5' overhang may be determined, which increases the information obtained from each SNP or locus of interest.

After labeling, each Streptawell was rinsed with 1×PBS (100 µl) three times. The "filled in" DNA fragments were then released from the Streptawells by digestion with the restriction enzyme EcoRI, according to the manufacturer's instructions that were supplied with the enzyme (FIGS. 8A–8D). Digestion was performed for 1 hour at 37° C. with shaking at 120 rpm.

Detection of the Locus of Interest

After release from the streptavidin matrix, 2–3 µl of the 10 µl sample was loaded in a 48 well membrane tray (The Gel Company, catalog number TAM48-01). The sample in the tray was absorbed with a 48 Flow Membrane Comb (The Gel Company, catalog number AM48), and inserted into a 36 cm 5% acrylamide (urea) gel (BioWhittaker Molecular Applications, Long Ranger Run Gel Packs, catalog number 50691).

The sample was electrophoresed into the gel at 3000 volts for 3 min. The membrane comb was removed, and the gel was run for 3 hours on an ABI 377 Automated Sequencing Machine. The incorporated labeled nucleotide was detected by fluorescence.

As shown in FIG. 9A, from a sample of thirty six (36) individuals, one of two nucleotides, either adenosine or guanine, was detected at SNP HC21S00027. These are the two nucleotides reported to exist at SNP HC21S00027 (http://snp.cshl.org/snpsearch.shtml).

One of two nucleotides, either guanine or cytosine, was detected at SNP TSC0095512 (FIG. 9B). The same results were obtained whether the locus of interest was amplified with a second primer that contained a recognition site for BceA I or the second primer contained a recognition site for BsmF I.

As shown in FIG. 9C, one of two nucleotides was detected at SNP TSC0264580, which was either adenosine or cytosine. These are the two nucleotides reported for this SNP site (http://snp.cshl.org/snpsearch.shtml). In addition, a thymidine was detected one base upstream of the locus of interest. In a sequence dependent manner, BsmF I cuts some DNA molecules at the 10/14 position and other DNA molecules, which have the same sequence, at the 11/15 position. When the restriction enzyme BsmF I cuts 11 nucleotides away on the sense strand and 15 nucleotides away on the antisense strand, the 3' recessed end is one base upstream of the SNP site. The sequence of SNP TSC0264580 indicated that the base immediately preceding the SNP site was a thymidine. The incorporation of a labeled ddNTP into this position generated a fragment one base smaller than the fragment that was cut at the 10/14 position. Thus, the DNA molecules cut at the 11/15 position provided sequence information about the base immediately preceding the SNP site, and the DNA molecules cut at the 10/14 position provided sequence information about the SNP site.

SNP HC21S00027 was amplified using a second primer that contained the recognition site for BsmF I. A mixture of labeled ddNTPs and unlabeled dNTPs was used to fill in the 5' overhang generated by digestion with BsmF I. If a dNTP was incorporated, the polymerase continued to incorporate nucleotides until a ddNTP was incorporated. A population of DNA fragments, each differing by one base, was generated, which allowed the full sequence of the overhang to be determined.

As seen in FIG. 9D, an adenosine was detected, which was complementary to the nucleotide (a thymidine) immediately preceding the SNP or locus of interest. This nucleotide was detected because of the 11/15 cutting property of BsmF I, which is described in detail above. A guanine and an adenosine were detected at the SNP site, which are the two nucleotides reported for this SNP site (FIG. 9A). The two nucleotides were detected at the SNP site because the molecular weights of the dyes differ, which allowed separation of the two nucleotides. The next nucleotide detected was a thymidine, which is complementary to the nucleotide immediately downstream of the SNP site. The next nucleotide detected was a guanine, which was complementary to the nucleotide two bases downstream of the SNP site. Finally, an adenosine was detected, which was complementary to the third nucleotide downstream of the SNP site. Sequence information was obtained not only for the SNP site but for the nucleotide immediately preceding the SNP site and the next three nucleotides.

None of the loci of interest contained a mutation. However, if one of the loci of interest harbored a mutation including but not limited to a point mutation, insertion, deletion, translocation or any combination of said mutations, it could be identified by comparison to the consensus or published sequence. Comparison of the sequences attributed to each of the loci of interest to the native, non-disease related sequence of the gene at each locus of interest determines the presence or absence of a mutation in that sequence. The finding of a mutation in the sequence is then interpreted as the presence of the indicated disease, or a predisposition to develop the same, as appropriate, in that individual. The relative amounts of the mutated vs. normal or non-mutated sequence can be assessed to determine if the subject has one or two alleles of the mutated sequence, and thus whether the subject is a carrier, or whether the indicated mutation results in a dominant or recessive condition.

Example 3

Four loci of interest from chromosome 1 and two loci of interest from chromosome 21 were amplified in separate PCR reactions, pooled together, and analyzed. The primers were designed so that each amplified locus of interest was a different size, which allowed detection of the loci of interest.

Preparation of Template DNA

The template DNA was prepared from a 5 ml sample of blood obtained by venipuncture from a human volunteer with informed consent. Template DNA was isolated using the QIAmp DNA Blood Midi Kit supplied by QIAGEN (Catalog number 51183). The template DNA was isolated as per instructions included in the kit. Template DNA was isolated from thirty-six human volunteers, and then pooled into a single sample for further analysis.

Design of Primers

SNP TSC 0087315 was amplified using the following primers:

```
First primer:  5' TTACAATGCATGAATTCATCTTGGTCTCTCAAAGTGC 3'  (SEQ ID NO:15)

Second primer: 5' TGGACCATAAACGGCCAAAAACTGTAAG 3'              (SEQ ID NO:16)
```

SNP TSC0214366 was amplified using the following primers:

```
First primer:  5' ATGACTAGCTATGAATTCGTTCAAGGTAGAAAATGGAA 3'  (SEQ ID NO:13)

Second primer: 5' GAGAATTAGAACGGCCCAAATCCCACTC 3'              (SEQ ID NO:14)
```

SNP TSC 0413944 was amplified with the following primers:

```
First primer:  5' TACCTTTTGATCGAATTCAAGGCCAAAAATATTAAGTT 3'  (SEQ ID NO:23)

Second primer: 5' TCGAACTTTAACGGCCTTAGAGTAGAGA 3'              (SEQ ID NO:24)
```

SNP TSC0095512 was amplified using the following primers:

```
First primer:  5' AAGTTTAGATCAGAATTCGTGAAAGCAGAAGTTGTCTG 3' (SEQ ID NO:11)

Second primer: 5' TCTCCAACTAACGGCTCATCGAGTAAAG 3'          (SEQ ID NO:12)
```

SNP HC21S00131 was amplified with the following primers:

```
First primer:  5' CGATTTCGATAAGAATTCAAAAGCAGTTCTTAGTTCAG 3' (SEQ ID NO:25)

Second primer: 5' TGCGAATCTTACGGCTGCATCACATTCA 3'           (SEQ ID NO:26)
```

SNP HC21S00027 was amplified with the following primers:

```
First primer:  5' ATAACCGTATGCGAATTCTATAATTTTCCTGATAAAGG 3' (SEQ ID NO:17)

Second primer: 5' CTTAAATCAGACGGCTAGGTAAACTTCA 3'           (SEQ ID NO:19)
```

For each SNP, the first primer contained a recognition site for the restriction enzyme EcoRI and had a biotin tag at the extreme 5' end. The second primer used to amplify each SNP contained a recognition site for the restriction enzyme BceA I.

PCR Reaction

The PCR reactions were performed as described in Example 2 except that the following annealing temperatures were used: the annealing temperature for the first cycle of PCR was 37° C. for 30 seconds, the annealing temperature for the second cycle of PCR was 57° C. for 30 seconds, and the annealing temperature for the third cycle of PCR was 64° C. for 30 seconds. All subsequent cycles had an annealing temperature of 64° C. for 30 seconds. Thirty seven (37) cycles of PCR were performed. After PCR, ¼ of the volume was removed from each reaction, and combined into a single tube.

Purification of Fragment of Interest

The PCR products (now combined into one sample, and referred to as "the sample") were separated from the genomic template DNA as described in Example 2 except that the sample was bound to a single well of a Streptawell microtiter plate.

Restriction Enzyme Digestion of Isolated Fragments

The sample was digested with the restriction enzyme BceA I, which bound the recognition site in the second primer. The restriction enzyme digestions were performed following the instructions supplied with the enzyme. After the restriction enzyme digest, the wells were washed three times with 1×PBS.

Incorporation of Nucleotides

The restriction enzyme digest described above yielded DNA molecules with a 5' overhang, which contained the SNP site or locus of interest and a 3' recessed end. The 5' overhang functioned as a template allowing incorporation of a nucleotide in the presence of a DNA polymerase.

The following components were used for the fill in reaction: 1 µl of fluorescently labeled ddATP; 1 µl of fluorescently labeled ddTTP; 1 µl of fluorescently labeled ddGTP; 1 µl of fluorescently labeled ddCTP; 2 µl of 10× sequenase buffer, 0.25 µl of Sequenase, and water as needed for a 20 µl reaction. The fill in reaction was performed at 40° C. for 10 min. All labeling reagents were obtained from Amersham (Thermo Sequenase Dye Terminator Cycle Sequencing Core Kit (US 79565); the concentration of the ddNTPS provided in the kit is proprietary and not published by Amersham). In the presence of fluorescently labeled ddNTPs, the 3' recessed end was filled in by one base, which corresponds to the SNP or locus of interest.

After the incorporation of nucleotide, the Streptawell was rinsed with 1×PBS (100 µl) three times. The "filled in" DNA fragments were then released from the Streptawell by digestion with the restriction enzyme EcoRI following the manufacturer's instructions. Digestion was performed for 1 hour at 37° C. with shaking at 120 rpm.

Detection of the Locus of Interest

After release from the streptavidin matrix, 2–3 µl of the 10 µl sample was loaded in a 48 well membrane tray (The Gel Company, catalog number TAM48-01). The sample in the tray was absorbed with a 48 Flow Membrane Comb (The Gel Company, catalog number AM48), and inserted into a 36 cm 5% acrylamide (urea) gel (BioWhittaker Molecular Applications, Long Ranger Run Gel Packs, catalog number 50691).

The sample was electrophoresed into the gel at 3000 volts for 3 min. The membrane comb was removed, and the gel was run for 3 hours on an ABI 377 Automated Sequencing Machine. The incorporated nucleotide was detected by fluorescence.

The primers were designed so that each amplified locus of interest differed in size. As shown in FIG. 10, each amplified loci of interest differed by about 5–10 nucleotides, which allowed the loci of interest to be separated from one another by gel electrophoresis. Two nucleotides were detected for SNP TSC0087315, which were guanine and cytosine. These are the two nucleotides reported to exist at SNP TSC0087315 (http://snp.cshl.org/snpsearch.shtml). The sample comprised template DNA from 36 individuals and because the DNA molecules that incorporated a guanine differed in molecular weight from those that incorporated a cytosine, distinct bands were seen for each nucleotide.

Two nucleotides were detected at SNP HC21S00027, which were guanine and adenosine (FIG. 10). The two nucleotides reported for this SNP site are guanine and adenosine (http://snp.cshl.org/snpsearch.shtml). As discussed above, the sample contained template DNA from thirty-six individuals, and one would expect both nucleotides to be represented in the sample. The molecular weight of the DNA fragments that incorporated a guanine was distinct from the DNA fragments that incorporated an adenosine, which allowed both nucleotides to be detected.

The nucleotide cytosine was detected at SNP TSC0214366 (FIG. 10). The two nucleotides reported to exist at this SNP position are thymidine and cytosine.

The nucleotide guanine was detected at SNP TSC0413944 (FIG. 10). The two nucleotides reported for this SNP are guanine and cytosine (http://snp.cshl.org/snpsearch.shtml).

The nucleotide cytosine was detected at SNP TSC0095512 (FIG. 10). The two nucleotides reported for this SNP site are guanine and cytosine (http://snp.cshl.org/snpsearch.shtml).

The nucleotide detected at SNP HC21S00131 was guanine. The two nucleotides reported for this SNP site are guanine and adenosine (http://snp.cshl.org/snpsearch.shtml).

As discussed above, the sample was comprised of DNA templates from thirty-six individuals and one would expect both nucleotides at the SNP sites to be represented. For SNP TSC0413944, TSC0095512, TSC0214366 and HC21S00131, one of the two nucleotides was detected. It is likely that both nucleotides reported for these SNP sites are present in the sample but that one fluorescent dye overwhelms the other. The molecular weight of the DNA molecules that incorporated one nucleotide did not allow efficient separation of the DNA molecules that incorporated the other nucleotide. However, the SNPs were readily separated from one another, and for each SNP, a proper nucleotide was incorporated. The sequences of multiple loci of interest from multiple chromosomes, which were treated as a single sample after PCR, were determined.

A single reaction containing fluorescently labeled ddNTPs was performed with the sample that contained multiple loci of interest. Alternatively, four separate fill in reactions can be performed where each reaction contains one fluorescently labeled nucleotide (ddATP, ddTTP, ddGTP, or ddCTP) and unlabeled ddNTPs (see Example 2, FIGS. 7A–7D and FIGS. 9A–C). Four separate "fill in" reactions will allow detection of any nucleotide that is present at the loci of interest. For example, if analyzing a sample that contains multiple loci of interest from a single individual, and said individual is heterozygous at one or more than one loci of interest, four separate "fill in" reactions can be used to determine the nucleotides at the heterozygous loci of interest.

Also, when analyzing a sample that contains templates from multiple individuals, four separate "fill in" reactions will allow detection of nucleotides present in the sample, independent of how frequent the nucleotide is found at the locus of interest. For example, if a sample contains DNA templates from 50 individuals, and 49 of the individuals have a thymidine at the locus of interest, and one individual has a guanine, the performance of four separate "fill in" reactions, wherein each "fill in" reaction is run in a separate lane of a gel, such as in FIGS. 9A–9C, will allow detection of the guanine. When analyzing a sample comprised of multiple DNA templates, multiple "fill in" reactions will alleviate the need to distinguish multiple nucleotides at a single site of interest by differences in mass.

In this example, multiple single nucleotide polymorphisms were analyzed. It is also possible to determine the presence or absence of mutations, including point mutations, transitions, transversions, translocations, insertions, and deletions from multiple loci of interest. The multiple loci of interest can be from a single chromosome or from multiple chromosomes. The multiple loci of interest can be from a single gene or from multiple genes.

The sequence of multiple loci of interest that cause or predispose to a disease phenotype can be determined For example, one could amplify one to tens to hundreds to thousands of genes implicated in cancer or any other disease. The primers can be designed so that each amplified loci of interest differs in size. After PCR, the amplified loci of interest can be combined and treated as a single sample. Alternatively, the multiple loci of interest can be amplified in one PCR reaction or the total number of loci of interest, for example 100, can be divided into samples, for example 10 loci of interest per PCR reaction, and then later pooled. As demonstrated herein, the sequence of multiple loci of interest can be determined. Thus, in one reaction, the sequence of one to ten to hundreds to thousands of genes that predispose or cause a disease phenotype can be determined.

Having now fully described the invention, the same will be understood by those with skill in the art that the scope can be performed with a wide and equivalent range of conditions, parameters, and the like, without affecting the spirit or scope of the invention or any embodiment thereof.

All documents, e.g., scientific publications, patents and patent publications recited herein are hereby incorporated by reference in their entirety to the same extent as if each individual document was specifically and individually indicated to be incorporated by reference in its entirety. Where the document cited only provides the first page of the document, the entire document is intended, including the remaining pages of the document.

What is claimed is:

1. A method for determining a sequence of a locus of interest, said method comprising:
   (a) amplifying a locus of interest on a template DNA using a first and second primers, each of the first and second primers comprising a 3' annealing region that anneals to the template DNA, wherein the second primer contains a recognition site for a restriction enzyme such that digestion with the restriction enzyme generates a 5' overhang containing the locus of interest, and wherein the melting temperature of the 3' annealing region of the first primer is greater than the melting temperature of the 3' annealing region of the second primer, and further wherein the annealing temperature for cycle 1 of the amplification is at about the melting temperature of the 3' annealing region of the second primer, the annealing temperature for cycle 2 of the amplification is at about the melting temperature of the 3' annealing region of the first primer, and the annealing temperature for cycle 3 is at about the melting temperature of the entire second primer, and wherein the annealing temperatures for cycle 2 and cycle 3 are greater than the annealing temperature for cycle 1;
   (b) digesting the amplified DNA with the restriction enzyme that recognizes the recognition site on the second primer;
   (c) incorporating a nucleotide into the digested DNA of (b) by using the 5' overhang containing the locus of interest as a template; and
   (d) determining the sequence of the locus of interest by determining the sequence of the DNA of (c) containing the incorporated nucleotide.

2. The method of claim 1, wherein the amplification of step (a) comprises cycles of amplification subsequent to cycle 3, wherein the annealing temperature of the cycles of amplification subsequent to cycle 3 is at about the melting temperature of the entire second primer.

3. The method of claim 1, wherein the template DNA is obtained from a source selected from the group consisting of a bacterium, fungus, virus, protozoan, plant, animal and human.

4. The method of claim 1, wherein the template DNA is obtained from a human source.

5. The method of claim 1, wherein the template DNA is obtained from a sample selected from the group consisting of a cell, tissue, blood, serum, plasma, urine, spinal fluid, lymphatic fluid, semen, vaginal secretion, ascitic fluid, saliva, mucosa secretion, peritoneal fluid, fecal matter, and body exudates.

6. The method of claim 1, wherein the amplification in (a) comprises polymerase chain reaction (PCR).

7. The method of claim 1, wherein the restriction enzyme cuts DNA at the recognition site.

8. The method of claim 7, wherein a 5' region of the second primer does not anneal to the template DNA.

9. The method of claim 7, wherein a 5' region of the first primer does not anneal to the template DNA.

10. The method of claim 7, wherein the restriction enzyme is selected from the group consisting of BsaJ I, Bssk I, Dde I, EcoN I, Fnu4H I, and Hinf I.

11. The method of claim 1, wherein the restriction enzyme cuts DNA at a distance from the recognition site.

12. The method of claim 11, wherein a 5' region of the second primer does not anneal to the template DNA.

13. The method of claim 11, wherein a 5' region of the first primer does not anneal to the template DNA.

14. The method of claim 11, wherein an annealing length of the 3' region of the second primer is selected from the group consisting of 25–20, 20–15, 15, 14, 13, 12, 11, 10, 9, 8, 7, 6, 5, 4, and less than 4 bases.

15. The method of claim 11, wherein the recognition site is for a Type IIS restriction enzyme.

16. The method of claim 15, wherein the Type IIS restriction enzyme is selected from the group consisting of: Alw I, Alw26 I, Bbs I, Bbv I, BceA I, Bmr I, Bsa I, Bst71 I, BsmA I, BsmB I, BsmF I, BspM I, Ear I, Fau I, Fok I, Hga I, Ple I, Sap I, SSfaN I, and Sthi32 I.

17. The method of claim 15, wherein the Type IIS restriction enzyme is BceA I or BsmF I.

18. The method of claim 1, wherein the 3' end of the second primer is adjacent to the locus of interest.

19. The method of claim 1, wherein the first primer contains a recognition site for a restriction enzyme that is different from the recognition site for the restriction enzyme on the second primer.

20. The method of claim 19, further comprising digesting the DNA of (c) with a restriction enzyme that recognizes the recognition site on the first primer.

21. The method of claim 1, wherein the first primer, the second primer, or both the first primer and the second primer contain a tag at the 5' terminus.

22. The method of claim 1, wherein the first primer contains a tag at the 5' terminus.

23. The method of claim 22, wherein the tag is used to separate the amplified DNA from the template DNA.

24. The method of claim 23, wherein the tag is used to separate the amplified DNA containing the incorporated nucleotide from the amplified DNA that does not contain the incorporated nucleotide.

25. The method of claim 22, wherein the tag is selected from the group consisting of: radioisotope, fluorescent reporter molecule, chemiluminescent reporter molecule, antibody, antibody fragment, hapten, biotin, derivative of biotin, photobiotin, iminobiotin, digoxigenin, avidin, enzyme, acridinium, sugar, enzyme, apoenzyme, homopolymeric oligonucleotide, hormone, ferromagnetic moiety, paramagnetic moiety, diamagnetic moiety, phosphorescent moiety, luminescent moiety, electrochemiluminescent moiety, chromatic moiety, moiety having a detectable electron spin resonance, electrical capacitance, dielectric constant, electrical conductivity, and combinations thereof.

26. The method of claim 22, wherein the tag is biotin.

27. The method of claim 26, wherein the biotin tag is used to separate amplified DNA from the template DNA using a streptavidin matrix.

28. The method of claim 27, wherein the streptavidin matrix is coated on wells of a microtiter plate.

29. The method of claim 1, wherein the incorporation of a nucleotide in (c) is by a DNA polymerase selected from the group consisting of E. coli DNA polymerase, Klenow fragment of E. coli DNA polymerase I, T7 DNA polymerase, T4 DNA polymerase, Taq polymerase, Pfu DNA polymerase, Vent DNA polymerase and sequenase.

30. The method of claim 1, wherein the incorporation of a nucleotide in (c) comprises incorporation of a labeled nucleotide.

31. The method of claim 30, wherein the labeled nucleotide is selected from the group consisting of a dideoxynucleotide triphosphate and deoxynucleotide triphosphate.

32. The method of claim 30, wherein the labeled nucleotide is labeled with a molecule selected from the group consisting of radioactive molecule, fluorescent molecule, antibody, antibody fragment, hapten, carbohydrate, biotin, derivative of biotin, phosphorescent moiety, luminescent moiety, electrochemiluminescent moiety, chromatic moiety, moiety having a detectable electron spin resonance, moiety having an electrical capacitance, moiety having a dielectric constant, and moiety having a detectable electrical conductivity.

33. The method of claim 30, wherein the labeled nucleotide is labeled with a fluorescent molecule.

34. The method of claim 33, wherein the incorporation of a fluorescent labeled nucleotide further comprises using a mixture of fluorescent and unlabeled nucleotides.

35. The method of claim 30, wherein the determination of the sequence of the locus of interest in (d) comprises detecting labeled nucleotide.

36. The method of claim 35, wherein the detection is by a method selected from the group consisting of gel electrophoresis, polyacrylamide gel electrophoresis, fluorescence detection system, sequencing, ELISA, mass spectrometry, fluorometry, hybridization, microarray, and Southern Blot.

37. The method of claim 35, wherein the detection method is DNA sequencing.

38. The method of claim 35, wherein the detection method is a fluorescence detection system.

39. The method of claim 1, wherein the incorporation of a nucleotide in (c) further comprises using a mixture of labeled and unlabeled nucleotides.

40. The method of claim 1, wherein the determination of the sequence of the locus of interest in (d) comprises detecting the nucleotide.

41. The method of claim 1, wherein the locus of interest is suspected of containing a single nucleotide polymorphism or mutation.

42. The method of claim 1, wherein the method is used for determining sequences of multiple loci of interest concurrently.

43. The method of claim 42, wherein the template DNA comprises multiple loci from a single chromosome.

44. The method of claim 42, wherein the template DNA comprises multiple loci from different chromosomes.

45. The method of claim 42, wherein the loci of interest on template DNA are amplified in one reaction.

46. The method of claim 42, wherein each of the loci of interest on template DNA is amplified in a separate reaction.

47. The method of claim 46, wherein the amplified DNA are pooled together prior to digestion of the amplified DNA.

48. The method of claim 42, wherein each of the DNA of (c) containing the incorporated nucleotide and containing a locus of interest is separated from other loci of interest prior to (d).

49. The method of claim 42, wherein at least one of the loci of interest is suspected of containing a single nucleotide polymorphism or a mutation.

50. A method for determining a sequence of a locus of interest, said method comprising:
(a) amplifying a locus of interest on a template DNA using a first and second primers, each of the first and second primers comprising a 3' annealing region that anneals to the template DNA, wherein the second primer contains a recognition site for a restriction enzyme such that digestion with the restriction enzyme generates a 5' overhang containing the locus of interest, and wherein the melting temperature of the 3' annealing region of the first primer is greater than the melting temperature of the 3' annealing region of the second primer, and further wherein the annealing temperature for cycle 1 of the amplification is at about the melting temperature of the 3' annealing region of the second primer, and the annealing temperature for a cycle of amplification subsequent to the first cycle of amplification is at about the melting temperature of the 3' annealing region of the first primer, and wherein the annealing temperature for said cycle of amplification subsequent to the first cycle of amplification is greater than the annealing temperature for cycle 1;

(b) digesting the amplified DNA with the restriction enzyme that recognizes the recognition site on the second primer;

(c) incorporating a nucleotide into the digested DNA of (b) by using the 5' overhang containing the locus of interest as a template; and (d) determining the sequence of the locus of interest by determining the sequence of the DNA of (c) containing the incorporated nucleotide.

51. The method of claim 50, wherein the 5' region of the second primer does not anneal to the template DNA, and further wherein in a cycle of amplification subsequent to the cycle of amplification for which the annealing temperature is at about the melting temperature of the 3' annealing region of the first primer, the annealing temperature is at about the melting temperature of the entire second primer.

52. A method for determining a sequence of a locus of interest, said method comprising:

(a) amplifying a locus of interest on a template DNA using a first and second primers, each of the first and second primers comprising a 3' annealing region that anneals to the template DNA, wherein the second primer contains a recognition site for a restriction enzyme that cuts DNA at a distance from the recognition site and digestion with the restriction enzyme generates a 5' overhang containing the locus of interest, wherein the first primer contains a recognition site for a restriction enzyme that is different from the recognition site for the restriction enzyme on the second primer, and contains a tag at the 5' end, and wherein the melting temperature of the 3' annealing region of the first primer is greater than the melting temperature of the 3' annealing region of the second primer, and further wherein the annealing temperature for cycle 1 of the amplification is at about the melting temperature of the 3' annealing region of the second primer, the annealing temperature for cycle 2 of the amplification is at about the melting temperature of the 3' annealing region of the first primer, and the annealing temperature for cycle 3 is at about the melting temperature of the entire second primer, and further wherein the annealing temperatures for cycle 2 and cycle 3 are greater than the annealing temperature for cycle 1;

(b) digesting the amplified DNA with the restriction enzyme that recognizes the recognition site on the second primer;

(c) incorporating a labeled nucleotide into the digested DNA of (b) by using the 5' overhang containing the locus of interest as a template;

(d) digesting the DNA of (c) with the restriction enzyme that recognizes the recognition site on the first primer; and (e) determining the sequence of the locus of interest by determining the sequence of the digested DNA of (d) containing the labeled nucleotide.

53. The method of claim 52, wherein the tag is used to separate the amplified DNA from the template DNA.

54. A method for determining a sequence of a locus of interest, said method comprising:

(a) amplifying a locus of interest on a template DNA using a first and second primers, each of the first and second primers comprising a 3' annealing region that anneals to the template DNA, wherein the second primer contains a recognition site for a restriction enzyme such that digestion with the restriction enzyme generates a 5' overhang containing the locus of interest, wherein the 5' region of the second primer does not anneal to the template DNA, and wherein the annealing temperature for cycle 1 of the amplification is at about the melting temperature of the 3' annealing region of the second primer, and the annealing temperature for a cycle of amplification subsequent to the first cycle of amplification is at about the melting temperature of the entire second primer, and wherein the annealing temperature for said cycle of amplification subsequent to the first cycle of amplification is greater than the annealing temperature for cycle 1;

(b) digesting the amplified DNA with the restriction enzyme that recognizes the recognition site on the second primer;

(c) incorporating a nucleotide into the digested DNA of (b) by using the 5' overhang containing the locus of interest as a template; and (d) determining the sequence of the locus of interest by determining the sequence of the DNA of (c) containing the incorporated nucleotide.

* * * * *

SEQUENCE LISTING

<160> NUMBER OF SEQ ID NOS: 41

<210> SEQ ID NO 1
<211> LENGTH: 15
<212> TYPE: DNA
<213> ORGANISM: Artificial Sequence
<220> FEATURE:
<223> OTHER INFORMATION: BsmF I restriction enzyme half site
<221> NAME/KEY: misc_feature
<222> LOCATION: (6)..(15)
<223> OTHER INFORMATION: May be any nucleotide

<400> SEQUENCE: 1

```
gggacnnnnn nnnnn                                              15

<210> SEQ ID NO 2
<211> LENGTH: 19
<212> TYPE: DNA
<213> ORGANISM: Artificial Sequence
<220> FEATURE:
<223> OTHER INFORMATION: BsmF I restriction enzyme half site
<221> NAME/KEY: misc_feature
<222> LOCATION: (1)..(14)
<223> OTHER INFORMATION: May be any nucleotide

<400> SEQUENCE: 2
nnnnnnnnnn nnnngtccc                                          19

<210> SEQ ID NO 3
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 3
ggaaattcca tgatgcgtgg g                                       21

<210> SEQ ID NO 4
<211> LENGTH: 23
<212> TYPE: DNA
<213> ORGANISM: Artificial Sequence
<220> FEATURE:
<223> OTHER INFORMATION: Template DNA for oligonucleotide primer
<221> NAME/KEY: misc_feature
<222> LOCATION: (19)..(21)
<223> OTHER INFORMATION: May be any nucleotide

<400> SEQUENCE: 4
ggaaattcca tgatgcgtnn nac                                     23

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 5
ggaaattcca tgatgcgtac c                                       21

<210> SEQ ID NO 6
<211> LENGTH: 25
<212> TYPE: DNA
<213> ORGANISM: Artificial Sequence
<220> FEATURE:
<223> OTHER INFORMATION: Template DNA for oligonucleotide primer
<221> NAME/KEY: misc_feature
<222> LOCATION: (22)..(23)
<223> OTHER INFORMATION: May be any nucleotide

<400> SEQUENCE: 6
ggaaattcca tgatgcgtac cnngg                                   25

<210> SEQ ID NO 7
<211> LENGTH: 11
<212> TYPE: DNA
<213> ORGANISM: Artificial Sequence
<220> FEATURE:
<223> OTHER INFORMATION: Recognition site for Eco NI restriction enzyme
```

```
<221> NAME/KEY: misc_feature
<222> LOCATION: (4)..(8)
<223> OTHER INFORMATION: May be any nucleotide

<400> SEQUENCE: 7
cctnnnnnag g                                                          11

<210> SEQ ID NO 8
<211> LENGTH: 25
<212> TYPE: DNA
<213> ORGANISM: Artificial Sequence
<220> FEATURE:
<223> OTHER INFORMATION: Template DNA for oligonucleotide primer
<221> NAME/KEY: misc_feature
<222> LOCATION: (20)..(23)
<223> OTHER INFORMATION: May be any nucleotide

<400> SEQUENCE: 8
ggaaattcca tgatgcgtan nnngg                                           25

<210> SEQ ID NO 9
<211> LENGTH: 38
<212> TYPE: DNA
<213> ORGANISM: Artificial Sequence
<220> FEATURE:
<223> OTHER INFORMATION: Oligonucleotide pirmer

<400> SEQUENCE: 9
tagaatagca ctgaattcag gaatacaatc attgtcac                             38

<210> SEQ ID NO 10
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 10
atcacgataa acggccaaac tcaggtta                                        28

<210> SEQ ID NO 11
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 11
aagtttagat cagaattcgt gaaagcagaa gttgtctg                             38

<210> SEQ ID NO 12
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 12
tctccaacta acggctcatc gagtaaag                                        28

<210> SEQ ID NO 13
<211> LENGTH: 38
<212> TYPE: DNA
<213> ORGANISM: Artificial Sequence
<220> FEATURE:
<223> OTHER INFORMATION: Oligonucleotide primer
```

<400> SEQUENCE: 13
atgactagct atgaattcgt tcaaggtaga aaatggaa    38

<210> SEQ ID NO 14
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 14
gagaattaga acggcccaaa tcccactc    28

<210> SEQ ID NO 15
<211> LENGTH: 37
<212> TYPE: DNA
<213> ORGANISM: Artificial Sequence
<220> FEATURE:
<223> OTHER INFORMATION: Oligonucleotide primer

<400> SEQUENCE: 15
ttacaatgca tgaattcatc ttggtctctc aaagtgc    37

<210> SEQ ID NO 16
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 16
tggaccataa acggccaaaa actgtaag    28

<210> SEQ ID NO 17
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 17
ataaccgtat gcgaattcta taattttcct gataaagg    38

<210> SEQ ID NO 18
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 18
cttaaatcag gggactaggt aaacttca    28

<210> SEQ ID NO 19
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 19
cttaaatcag acggctaggt aaacttca    28

<210> SEQ ID NO 20
<211> LENGTH: 28

```
<212> TYPE: DNA
<213> ORGANISM: Artificial Sequence
<220> FEATURE:
<223> OTHER INFORMATION: Oligonucleotide primer

<400> SEQUENCE: 20
tctccaacta gggactcatc gagtaaag                                       28

<210> SEQ ID NO 21
<211> LENGTH: 37
<212> TYPE: DNA
<213> ORGANISM: Artificial Sequence
<220> FEATURE:
<223> OTHER INFORMATION: Oligonucleotide primer

<400> SEQUENCE: 21
aacgccgggc gagaattcag tttttcaact tgcaagg                             37

<210> SEQ ID NO 22
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 22
ctacacatat ctgggacgtt ggccatcc                                       28

<210> SEQ ID NO 23
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 23
taccttttga tcgaattcaa ggccaaaaat attaagtt                            38

<210> SEQ ID NO 24
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 24
tcgaacttta acggccttag agtagaga                                       28

<210> SEQ ID NO 25
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 25
cgatttcgat aagaattcaa aagcagttct tagttcag                            38

<210> SEQ ID NO 26
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 26
```

```
tgcgaatctt acggctgcat cacattca                                              28
```

```
<210> SEQ ID NO 27
<211> LENGTH: 35
<212> TYPE: DNA
<213> ORGANISM: Artificial Sequence
<220> FEATURE:
<223> OTHER INFORMATION: Partial DNA sequence of SNP HC21S00027

<400> SEQUENCE: 27
gccaagtata attttcctga taaaggctgg gctgc                                      35
```

```
<210> SEQ ID NO 28
<211> LENGTH: 31
<212> TYPE: DNA
<213> ORGANISM: Artificial Sequence
<220> FEATURE:
<223> OTHER INFORMATION: Partial DNA sequence of SNP HC21S00027

<400> SEQUENCE: 28
caatttgcac tartgaagtt tacctaacaa t                                          31
```

```
<210> SEQ ID NO 29
<211> LENGTH: 32
<212> TYPE: DNA
<213> ORGANISM: Artificial Sequence
<220> FEATURE:
<223> OTHER INFORMATION: Partial DNA sequence of SNP TSC0095512

<400> SEQUENCE: 29
ctatatgtga aagcagaagt tgtctgataa tc                                         32
```

```
<210> SEQ ID NO 30
<211> LENGTH: 26
<212> TYPE: DNA
<213> ORGANISM: Artificial Sequence
<220> FEATURE:
<223> OTHER INFORMATION: Partial DNA sequence of SNP TSC0095512

<400> SEQUENCE: 30
ccaaggsctt tactcgatga tagctg                                                26
```

```
<210> SEQ ID NO 31
<211> LENGTH: 41
<212> TYPE: DNA
<213> ORGANISM: Artificial Sequence
<220> FEATURE:
<223> OTHER INFORMATION: SNP HC21S00027 after amplification

<400> SEQUENCE: 31
ataaccgtat gcgaattcta taattttcct gataaaggct g                               41
```

```
<210> SEQ ID NO 32
<211> LENGTH: 41
<212> TYPE: DNA
<213> ORGANISM: Artificial Sequence
<220> FEATURE:
<223> OTHER INFORMATION: SNP HC21S00027 after amplification

<400> SEQUENCE: 32
caatttgcac tartgaagtt tacctagtcc ccagatttaa g                               41
```

```
<210> SEQ ID NO 33
<211> LENGTH: 41
<212> TYPE: DNA
<213> ORGANISM: Artificial Sequence
```

```
<220> FEATURE:
<223> OTHER INFORMATION: SNP HC21S00027 after amplification

<400> SEQUENCE: 33
caatttgcac tartgaagtt tacctagccg tcagatttaa g                    41

<210> SEQ ID NO 34
<211> LENGTH: 44
<212> TYPE: DNA
<213> ORGANISM: Artificial Sequence
<220> FEATURE:
<223> OTHER INFORMATION: SNP TSC0095512 after amplification

<400> SEQUENCE: 34
aagtttagat cagaattcgt gaaagcagaa gttgtctgat aatc                 44

<210> SEQ ID NO 35
<211> LENGTH: 35
<212> TYPE: DNA
<213> ORGANISM: Artificial Sequence
<220> FEATURE:
<223> OTHER INFORMATION: SNP TSC0095512 after amplification

<400> SEQUENCE: 35
ccaaggsctt tactcgatga gtcccttatc gtgat                           35

<210> SEQ ID NO 36
<211> LENGTH: 35
<212> TYPE: DNA
<213> ORGANISM: Artificial Sequence
<220> FEATURE:
<223> OTHER INFORMATION: SNP TSC0095512 after amplification

<400> SEQUENCE: 36
ccaaggsctt tactcgatga gccgtttatc gtgat                           35

<210> SEQ ID NO 37
<211> LENGTH: 13
<212> TYPE: DNA
<213> ORGANISM: Artificial Sequence
<220> FEATURE:
<223> OTHER INFORMATION: SNP HC21S00027 locus with an incorporated
      labeled ddNTP
<221> NAME/KEY: misc_feature
<222> LOCATION: (13)..(13)
<223> OTHER INFORMATION: Fluorescently labeled dideoxynucleotide

<400> SEQUENCE: 37
caatttgcac tar                                                   13

<210> SEQ ID NO 38
<211> LENGTH: 10
<212> TYPE: DNA
<213> ORGANISM: Artificial Sequence
<220> FEATURE:
<223> OTHER INFORMATION: TSC0095512 locus

<400> SEQUENCE: 38 aagsccttgg                                                       10

<210> SEQ ID NO 39
<211> LENGTH: 14
<212> TYPE: DNA
<213> ORGANISM: Artificial Sequence
<220> FEATURE:
<223> OTHER INFORMATION: SNP HC21S00027 locus with an incorporated
      labeled ddNTP
```

-continued

```
<221> NAME/KEY: misc_feature
<222> LOCATION: (14)..(14)
<223> OTHER INFORMATION: Fluorescently labeled dideoxynucleotide

<400> SEQUENCE: 39
caatttgcac tart                                                      14

<210> SEQ ID NO 40
<211> LENGTH: 15
<212> TYPE: DNA
<213> ORGANISM: Artificial Sequence
<220> FEATURE:
<223> OTHER INFORMATION: SNP HC21S00027 locus with an incorporated
      labeled ddNTP
<221> NAME/KEY: misc_feature
<222> LOCATION: (15)..(15)
<223> OTHER INFORMATION: Fluorescently labeled dideoxynucleotide

<400> SEQUENCE: 40
caatttgcac tartg                                                     15

<210> SEQ ID NO 41
<211> LENGTH: 16
<212> TYPE: DNA
<213> ORGANISM: Artificial Sequence
<220> FEATURE:
<223> OTHER INFORMATION: SNP HC21S00027 locus with an incorporated
      labeled ddNTP
<221> NAME/KEY: misc_feature
<222> LOCATION: (16)..(16)
<223> OTHER INFORMATION: Fluorescently labeled dideoxynucleotide

<400> SEQUENCE: 41
caatttgcac tartga                                                    16
```